(12) United States Patent
Desai et al.

(10) Patent No.: US 9,394,300 B2
(45) Date of Patent: Jul. 19, 2016

(54) QUINOLONE DERIVATIVES

(71) Applicant: Cadila Healthcare Limited, Ahmedabad (IN)

(72) Inventors: Ranjit C. Desai, Ahmedabad (IN); Vrajesh Pandya, Ahmedabad (IN); Pankaj Ramanbhai Patel, Ahmedabad (IN)

(73) Assignee: Cadila Healthcare Limited (IN)

( * ) Notice: Subject to any disclaimer, the term of this patent is extended or adjusted under 35 U.S.C. 154(b) by 0 days.

(21) Appl. No.: 14/652,024

(22) PCT Filed: Dec. 23, 2013

(86) PCT No.: PCT/IN2013/000796
§ 371 (c)(1),
(2) Date: Jun. 12, 2015

(87) PCT Pub. No.: WO2014/102818
PCT Pub. Date: Jul. 3, 2014

(65) Prior Publication Data
US 2015/0299193 A1  Oct. 22, 2015

(30) Foreign Application Priority Data
Dec. 24, 2012 (IN) .................... 3600/MUM/2012

(51) Int. Cl.
| | | |
|---|---|---|
| *C07D 215/58* | (2006.01) |
| *A61K 31/4704* | (2006.01) |
| *C07D 471/04* | (2006.01) |
| *C07D 215/60* | (2006.01) |
| *C07D 401/04* | (2006.01) |
| *C07D 401/12* | (2006.01) |
| *C07D 413/04* | (2006.01) |
| *C07D 417/12* | (2006.01) |
| *C07D 491/04* | (2006.01) |
| *C07D 495/04* | (2006.01) |
| *C07D 513/04* | (2006.01) |
| *C07D 409/04* | (2006.01) |

(52) U.S. Cl.
CPC ............ *C07D 471/04* (2013.01); *C07D 215/58* (2013.01); *C07D 215/60* (2013.01); *C07D 401/04* (2013.01); *C07D 401/12* (2013.01); *C07D 409/04* (2013.01); *C07D 413/04* (2013.01); *C07D 417/12* (2013.01); *C07D 491/04* (2013.01); *C07D 495/04* (2013.01); *C07D 513/04* (2013.01); *A61K 31/4704* (2013.01)

(58) Field of Classification Search
CPC .. C07D 215/58; C07D 215/60; C07D 471/04; C07D 401/12; C07D 401/04; C07D 413/12; C07D 417/12; C07D 495/04; C07D 409/04; C07D 513/04; C07D 491/04; A61K 31/4704
See application file for complete search history.

(56) References Cited

U.S. PATENT DOCUMENTS

2015/0018546 A1 * 1/2015 Kawai et al. .......... C07D 471/04
544/117

FOREIGN PATENT DOCUMENTS

| WO | WO-2007/038571 A2 | 4/2007 |
| WO | WO-2007/070359 A2 | 6/2007 |
| WO | WO-2007/103905 A2 | 9/2007 |
| WO | 2008/010964 * | 1/2008 |
| WO | WO-2008/138060 A1 | 11/2008 |

OTHER PUBLICATIONS

Rabinowitz, J Med Chem, 56, 9369-9402, 2013.*
International Application No. PCT/IN2013/000796, International Preliminary Report on Patentability, mailed Mar. 31, 2015, 12 pgs.
International Application No. PCT/IN2013/000796, International Search Report and Written Opinion, mailed May 12, 2014, 14 pgs.
International Application No. PCT/IN2013/000796, Written Opinion of the International Preliminary Examining Authority, mailed Nov. 25, 2014, 10 pgs.

* cited by examiner

*Primary Examiner* — D M Seaman
(74) *Attorney, Agent, or Firm* — Schwegman, Lundberg & Woessner, P.A.

(57) ABSTRACT

The present invention relates to novel compounds of the general formula (I), their tautomeric forms, their stereoisomers, their pharmaceutically acceptable salts, pharmaceutical compositions containing them, methods for their preparation, use of these compounds in medicine and the intermediates involved in their preparation.

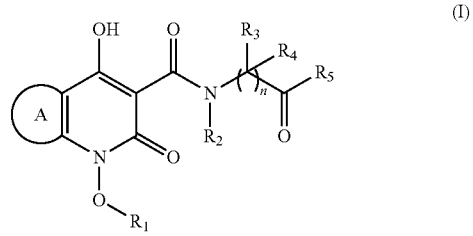

(I)

10 Claims, No Drawings

QUINOLONE DERIVATIVES

This application is a U.S. National Stage Filing under 35 U.S.C. 371 from International Application No. PCT/IN2013/000796, filed on Dec. 23, 2013, and published as WO 2014/102818 A1 on Jul. 3, 2014, and which claims the benefit of priority under 35 U.S.C. §119 to Indian Patent Application No. 3600/MUM/2012, filed on Dec. 24, 2012, which are hereby incorporated by reference herein in their entireties.

FIELD OF INVENTION

The present invention relates to novel compounds of the general formula (I), their tautomeric forms, their stereoisomers, their pharmaceutically acceptable salts, pharmaceutical compositions containing them, methods for their preparation, use of these compounds in medicine and the intermediates involved in their preparation.

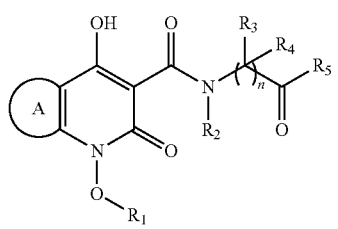

BACKGROUND OF THE INVENTION

Hypoxia-inducible factor (HIF) is a heteroduplex, with α and β subunit. The beta subunit is usually present in excess, while the alpha subunit is the limiting factor in the formation of the functional dimer. The HIF-α subunit binds with the β subunit in the nucleus and, with the cooperation of cofactors, binds to DNA sequences called hypoxia response elements, and hence induces expression of target genes. There are three isoforms of the α subunit, HIF-1α, HIF-2α and HIF-3α. The activity of HIF is regulated via hydroxylation at two proline residues by an oxygen-sensitive family of prolyl hydroxylase enzymes (PHD), known as PHD1, PHD2 and PHD3. Hydroxylation at one or both of these proline residues allows binding of HIF-α first by the von Hippel-Lindau tumor suppressor protein (pVHL) and then by ubiquitin ligase which results in rapid ubiquitination and proteosomal degradation. The HIF-α subunits are also regulated by hydroxylation at a C-terminal asparagine residue by factor inhibiting HIF (FIH), an oxygen-dependent hydroxylase enzyme. Factor inhibiting HIF prevents the recruitment of transcriptional coactivators, thereby blocking the activity of HIF.

Under normoxic (oxygenated) conditions, HIF-1α is rapidly degraded, while under hypoxic conditions, HIF-1α is stabilized due to hypoxia mediated reduction of PHD and FIH activities and is translocated into the nucleus, where it dimerizes with the constitutively expressed HIF-1β, thereby inducing the expression of several genes including glucose transporters, glycolytic enzymes, angiogenic growth factors, and several molecules involved in apoptosis and cell proliferation such as erythropoietin (EPO), transferrin, endothelin-1, iNOS, heme oxygenase 1, VEGF, IGF and IGF-binding proteins.

The oxygen sensitive PHD family is also dependent on the presence of ferrous iron, ascorbate and the citric acid cycle intermediate, 2-oxoglutarate (2OG). HIF activity, therefore, depends on oxygen concentrations, accessible iron and glucose metabolism through its regulation by FIH and PHD.

Inhibition of HIF prolyl hydroxylases and HIF asparagyl hydroxylases thus provides a powerful approach for oxygen-independent activation of HIF. Such HIF activation by pharmacological means results in enhanced expression of genes as described earlier which perform multiple functions to recover from hypoxic/ischemic conditions. Therefore, HIF activation can offer significant therapeutic benefits in various disease conditions such as anemia of various types and tissue injuries caused by hypoxia/ischemia in conditions like acute kidney injury, myocardial infarction, stroke, hepatic ischemia-reperfusion injury, peripheral vascular diseases and transplantation of liver and kidney.

Hb (Hemoglobin) is an iron-containing metalloprotein in red blood cells (RBCs) that delivers oxygen. Decreased Hb levels resulting from anemia can lead to hypoxia in various organs and, therefore, cause patients severe clinical complications, such as severe fatigue, dyspnea, heart problems, nerve damage, impaired mental function and even death. The cause of anemia is multifactorial: blood loss, increased RBC destruction (e.g., hemolytic anemia), and decreased or faulty RBC production (e.g., iron deficiency and sickle cell anemia). 80% of patients with chronic kidney disease (CKD) develop anemia because of decreased production of erythropoietin (EPO) in the kidney. EPO is an essential growth factor that stimulates the erythropoiesis, and maintains their viability. Patients with rheumatoid arthritis, chronic inflammatory and infectious disorders, chronic heart failure, and cancers or who are undergoing chemotherapy often become anemic due to deficiency of EPO production.

The current treatment for anemia in chronic diseases, including anemia of chronic kidney disease, is iron repletion and treatment with EPO or its analogs. In addition to the high cost of EPO and its analogs, there are several shortcomings to this approach. First, these must be injected subcutaneously or intravenously, making administration more difficult. Second, there is a significant proportion of patients resistant to therapy with EPO or its analogs. Treatment of anemia with HIF-hydroxylase inhibitors may bypass EPO resistance, through effects on iron metabolism, and avoid the increased death and cardiovascular events associated with supraphysiologic levels of EPO.

Compounds which provide a means for inhibiting HIF hydroxylases and thereby activating the HIF, leading to enhanced expression of the various genes including EPO, vascular endothelial growth factor (VEGF), adrenomodulin etc. are therefore expected to be useful in treating various disorders including anemia of different types and conditions associated with ischemia/hypoxia.

EP661269 discloses substituted heterocyclic carboxamides of the following general formula and their use as inhibitors of prolyl-4-hydroxylase and as inhibitors of collagen biosynthesis.

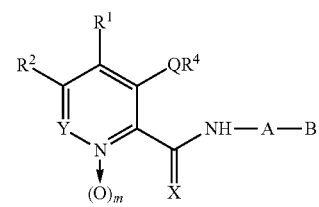

WO2004108681 discloses isoquinoline derivatives and their use in increasing endogeneous erythropoietin.

WO2007070359 discloses quinolone based compounds of the following general formula exhibiting prolyl hydroxylase inhibitory activity and uses thereof.

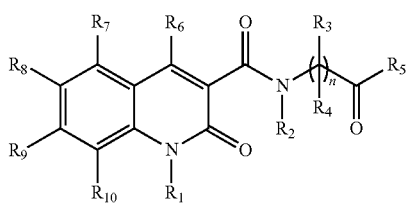

WO2008076425 discloses azaquinolone based compounds of the following general formula exhibiting prolyl hydroxylase inhibitory activity and uses thereof.

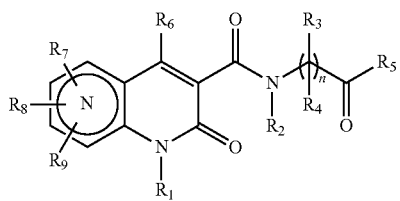

WO2011007856 discloses certain triazolopyridine derivatives of the formula below as prolyl hydroxylase inhibitors and erythropoetin production inducers.

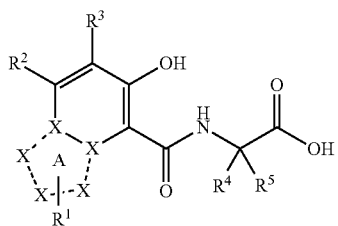

WO2012106472 discloses following napthyridine derivative based compounds as inhibitors of HIF hydroxylase.

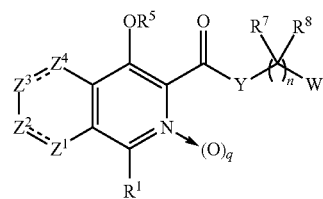

WO2013043621 discloses substituted certain pyrimidines compounds which are useful as HIF prolyl hydroxylase inhibitors to treat anemia and like conditions and having the following general formula.

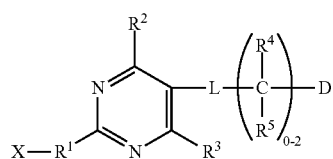

However, none of these compounds have reached the market and looking at the significant unmet medical need for such compounds based on their potential beneficial effects as discussed above, there is a need for identifying further compounds which can act as prolyl hydroxylase inhibitors. We herein disclose novel compounds which are expected to act as such inhibitors.

SUMMARY OF THE INVENTION

The present invention discloses novel compounds as defined by the general formula (I) that inhibits HIF hydroxylases, thereby increasing the stability and/or activity of hypoxia inducible factor (HIF) and thus has utility in any disease state where ischemia, hypoxia and/or anemia plays a role.

EMBODIMENTS OF THE INVENTION

The main objective of the present invention is to provide novel substituted compounds represented by the general formula (I), their tautomeric forms, their stereoisomers, their pharmaceutically acceptable salts, and pharmaceutical compositions containing them or their suitable mixtures.

In an embodiment of the present invention is provided processes for the preparation of novel compounds represented by the general formula (I), their tautomeric forms, their stereoisomers, their pharmaceutically acceptable salts.

In a further embodiment of the present invention is provided pharmaceutical compositions containing compounds of the general formula (I), their tautomeric forms, their stereoisomers, their pharmaceutically acceptable salts, or their mixtures in combination with suitable carriers, solvents, diluents and other media normally employed in preparing such compositions.

In a still further embodiment are provided use of the compounds of the present invention or their suitable pharmaceutically acceptable salts for the use in medicine.

DESCRIPTION OF THE INVENTION

Accordingly, the present invention relates to compounds of the general formula (I),

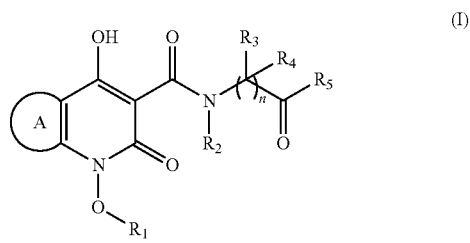

wherein $R_1$ represents hydrogen, optionally substituted $(C_1\text{-}C_{10})$ alkyl, $(C_2\text{-}C_{10})$alkenyl, $(C_2\text{-}C_{10})$alkynyl, $(C_3\text{-}C_8)$cycloalkyl, $(C_5\text{-}C_8)$cycloalkenyl, aryl, heteroaryl, heterocyclyl, aralkyl, cycloalkanylalkyl, heteroaralkyl, heterocyclylalkyl groups;

$R_2$ represents hydrogen, optionally substituted alkyl, cycloalkyl, aryl, heteroaryl, heterocyclyl and acyl groups;

$R_3$ and $R_4$ each independently represents hydrogen, optionally substituted alkyl, cycloalkyl, aryl, heterocyclyl, heteroaryl groups; or $R_3$ and $R_4$ together with the carbon atom to which they are attached forms a cycloalkyl, or heterocyclyl group wherein the heterocyclyl group may further be containing one or more heteroatoms selected from O, N & S;

$R_5$ is selected from the group comprising of —$OR_6$, —$COOR_6$, —$NR_7COR_6$ and $NR_7SO_2R_6$, wherein each of $R_6$ and $R_7$ at each occurrence are independently selected from the group comprising of hydrogen, optionally substituted groups selected from alkyl, cycloalkyl, aryl, heterocyclyl and heteroaryl;

'A' represents a 5-7 membered saturated or unsaturated carbocyclic or heterocyclic ring system wherein the heterocyclic ring may contain one or more heteroatoms selected from N, O or $S(O)_m$;

The said cycle representing 'A' may be further substituted by one or more substituents selected from the group of substituents represented by $R_8$;

$R_8$ at each occurrence independently represents the group comprising of hydrogen, hydroxy, cyano, halo, nitro, oxo, imino, haloalkyl, or optionally substituted groups selected from ($C_1$-$C_{10}$)alkyl, ($C_2$-$C_{10}$)alkenyl, ($C_2$-$C_{10}$)alkynyl, ($C_3$-$C_8$)cycloalkyl, ($C_5$-$C_8$)cycloalkenyl, aryl, heterocyclyl, heteroaryl aralkyl, heterocyclylalkyl, alkylsulfonyloxy, —$COR_9$, —$C(O)COR_9$, —$COOR_9$, —$OR_9$, —$S(O)_mR_9$, —$NR_9R_{10}$, —$CONR_9R_{10}$, —$N(R_9)COR_{10}$, —$N(R_9)COOR_{10}$, —$NR_9NR_{10}COR_9$, —$OCH_2COR_9$, —$N(R_9)CH_2COR_{10}$, —$N(R_9)C(O)COR_{10}$, —$C(O)CONR_9R_{10}$, —$OCONR_9R_{10}$, —$N(R_9)CONR_9R_{10}$, —$P(O)(OR_{10})_2$, —$SO_2NR_9R_{10}$, —$N(R_9)SO_2R_{10}$ derivatives, wherein $R_9$ and $R_{10}$ at each occurrence independently represents hydrogen, hydroxy, alkoxy, haloalkyl, optionally substituted ($C_1$-$C_{10}$) alkyl, ($C_2$-$C_{10}$)alkenyl, ($C_2$-$C_{10}$)alkynyl, ($C_3$-$C_8$)cycloalkyl, ($C_5$-$C_8$)cycloalkenyl, optionally substituted amino, aryl, heteroaryl, heterocyclyl, aralkyl, heterocyclylalkyl groups, provided that any of the substitutions do not form any S—S or O—O bond; or wherever feasible, $R_9$ and $R_{10}$ together with the atom to which they are attached may form a 5-8 membered cyclic ring optionally containing 0-2 additional heteroatoms selected from —O—, —$NR_7$— and $S(O)_m$— wherein $R_7$ is as defined earlier;

When any of $R_1$ or $R_8$ is further substituted the substitutions may be selected from hydrogen, hydroxy, cyano, halo, nitro, oxo, imino, haloalkyl, ($C_1$-$C_{10}$)alkyl, ($C_2$-$C_{10}$)alkenyl, ($C_2$-$C_{10}$)alkynyl, ($C_3$-$C_8$)cycloalkyl, ($C_5$-$C_8$)cycloalkenyl, aryl, heterocyclyl, heteroaryl, aralkyl, heterocyclylalkyl, alkylsulfonyloxy, —$COR_9$, —$C(O)COR_9$, —$COOR_9$, —$OR_9$, —$S(O)_mR_9$, —$NR_9R_{10}$, —$CONR_9R_{10}$, —$N(R_9)COR_{10}$, —$N(R_9)COOR_{10}$, —$NR_9NR_{10}COR_9$, —$OCH_2COR_9$, —$N(R_9)CH_2COR_{10}$, —$N(R_9)C(O)COR_{10}$, —$C(O)CONR_9R_{10}$, —$OCONR_9R_{10}$, —$N(R_9)CONR_9R_{10}$, —$P(O)(OR_{10})_2$, —$SO_2NR_9R_{10}$, —$N(R_9)SO_2R_{10}$ derivatives;

wherein each of $R_9$ & $R_{10}$ are as defined earlier;

'm' represents integers from 0-2 and 'n' represents integers from 1-6.

In an embodiment, the ($C_1$-$C_{10}$) alkyl chain as used herein before, may further optionally contain from 1-4 heteroatoms selected from O, S or N or the groups NRaRb, S(O)m, carbonyl or iminocarbonyl (—C=NH); wherein either of RaRb is independently selected from H, ($C_1$-$C_{10}$)alkyl groups, ($C_3$-$C_{10}$) cycloalkyl groups, provided that the alkyl chain formed does not include an S—S or O—O bond; Further preferred embodiments are those disclosed below.

Preferred $R_1$ may be selected from ($C_1$-$C_{10}$)alkyl, ($C_2$-$C_{10}$) alkenyl, ($C_2$-$C_{10}$)alkynyl, ($C_3$-$C_8$)cycloalkyl, cycloalkanylalkyl, aryl, heteroaryl, heterocyclyl, aralkyl, heterocyclylalkyl groups;

Preferred substituents on $R_1$ may be selected from hydrogen, hydroxy, cyano, halo, nitro, oxo, imino, haloalkyl, ($C_1$-$C_{10}$)alkyl, ($C_2$-$C_{10}$)alkenyl, ($C_2$-$C_{10}$)alkynyl, ($C_3$-$C_8$)cycloalkyl, aryl, heterocyclyl, heteroaryl, aralkyl, heterocyclylalkyl, —$COR_9$, —$C(O)COR_9$, —$COOR_9$, —$OR_9$, —$S(O)_mR_9$, —$NR_9R_{10}$, —$CONR_9R_{10}$, —$N(R_9)COR_{10}$, —$N(R_9)COOR_{10}$, —$NR_9NR_{10}COR_9$, —$OCH_2COR_9$, —$N(R_9)CH_2COR_{10}$, —$N(R_9)CONR_9R_{10}$, —$P(O)(OR_{10})_2$, —$SO_2NR_9R_{10}$, —$N(R_9)SO_2R_{10}$ derivatives;

wherein each of $R_9$ and $R_{10}$ are as defined earlier;

Preferred $R_2$ may be selected from hydrogen, optionally substituted alkyl, cycloalkyl and acyl groups;

Preferred $R_3$ and $R_4$ may be selected from hydrogen, optionally substituted alkyl, cycloalkyl groups or $R_3$ and $R_4$ together with the carbon atom to which they are attached form a cycloalkyl, or heterocyclyl ring;

Preferred $R_5$ may be selected from the group consisting of —$OR_6$, —$NR_7COR_6$ and —$NR_7SO_2R_6$; Preferred $R_6$ and $R_7$ may be independently selected from the group consisting of hydrogen, optionally substituted alkyl, cycloalkyl and heterocyclyl groups;

Preferred $R_8$ may be selected from the group comprising of hydrogen, hydroxy, cyano, halo, haloalkyl, ($C_1$-$C_{10}$)alkyl, ($C_2$-$C_{10}$)alkenyl, ($C_2$-$C_{10}$)alkynyl, ($C_3$-$C_8$)cycloalkyl, aryl, heterocyclyl, heteroaryl aralkyl, heterocyclylalkyl, —$COR_9$, —$COOR_9$, —$OR_9$, —$S(O)_mR_9$, —$NR_9R_{10}$, —$CONR_9R_{10}$, —$N(R_9)COR_{10}$, —$N(R_9)COOR_{10}$, —$OCH_2COR_9$, —$N(R_9)CH_2COR_{10}$, —$N(R_9)CONR_9R_{10}$, —$SO_2NR_9R_{10}$, —$N(R_9)SO_2R_{10}$ derivatives;

Preferred $R_9$ and $R_{10}$ may be selected from hydrogen, hydroxy, alkoxy, haloalkyl, optionally substituted ($C_1$-$C_{10}$) alkyl, ($C_2$-$C_{10}$)alkynyl, ($C_3$-$C_8$)cycloalkyl, optionally substituted amino, aryl, heteroaryl, heterocyclyl, aralkyl, heterocyclylalkyl groups, In a further embodiment the groups, radicals described above may be selected from:

- the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;
- the "alkenyl" group used either alone or in combination with other radicals, is selected from a radical containing from two to six carbons, more preferably groups selected from vinyl, allyl, 2-butenyl, 3-butenyl, 2-pentenyl, 3-pentenyl, 4-pentenyl, 2-hexenyl, 3-hexenyl, 4-hexenyl and the like; the "alkenyl" group includes dienes and trienes of straight and branched chains;
- the "alkynyl" group used either alone or in combination with other radicals, is selected from a linear or branched radical containing two to six carbon atoms, more preferably thienyl, 1-propynyl, 2-propynyl, 1-butynyl, 2-butynyl, 3-butynyl, 1-pentynyl, 2-pentynyl, 3-pentynyl, 4-pentynyl, 1-hexynyl, and the like. The term "alkynyl" includes di- and tri-ynes;
- the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like;
- the "cycloalkenyl" group used either alone or in combination with other radicals, are preferably selected from cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl and the like;
- the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;

the "haloalkyl" group is selected from an alkyl radical, as defined above, suitably substituted with one or more halogens; such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;

the "aryl" or "aromatic" group used either alone or in combination with other radicals, is selected from a suitable aromatic system containing one, two or three rings wherein such rings may be attached together in a pendant manner or may be fused, more preferably the groups are selected from phenyl, naphthyl, tetrahydronaphthyl, indane, biphenyl, and the like;

the "heterocyclyl" or "heterocyclic" group used either alone or in combination with other radicals, is selected from suitable aromatic or non-aromatic radicals containing one or more hetero atoms selected from O, N or S. The non-aromatic radicals may be saturated, partially saturated or unsaturated mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thieno piperidinyl, and the like; the aromatic radicals, may be selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;

In one embodiment, the heterocycle group, wherever applicable, may consist of appropriate number of carbon atoms and include from 1-4 heteroatoms selected from the group consisting of N, O, and $S(O)_m$, m=0-2, as defined above, wherein the heterocycle group may further be substituted with 1-2 carbonyl or 1-2 iminocarbonyl groups or one or more groups selected from $R^8$ as defined earlier;

As used herein, "carbocycle" or "carbocyclic residue" is intended to mean any stable monocyclic or bicyclic or tricyclic ring; any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin);

the "heteroaryl" or "heteroaromatic" group used either alone or in combination with other radicals, is selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;

the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;

the "aralkyl" group used either alone or in combination with other radicals, is selected from groups containing an aryl radical, as defined above, attached directly to an alkyl radical, as define above, more preferably groups selected from benzyl, phenethyl, and the like;

the "heterocyclylalkyl" group used either alone or in combination with other radicals, is selected from groups containing an heterocyclyl radical, as defined above, attached directly to an alkyl radical, as define above;

the "cycloalkanylalkyl" group used either alone or in combination with other radicals, is selected from groups containing a cycloalkyl radical, as defined above, attached directly to an alkyl radical, as define above;

the "heteroaralkyl" group used either alone or in combination with other radicals, is selected from groups containing an heteroaryl radical, as defined above, attached directly to an alkyl radical, as define above;

the "oxo" or "carbonyl" group used either alone (—C═O—) or in combination with other radicals such as alkyl described above, for e.g. "alkylcarbonyl", denotes a carbonyl radical (—C═O—) substituted with an alkyl radical described above such as acyl or alkanoyl;

the "alkylsulfonyloxy" group used either alone or in combination, refers to an alkylsulfonyl group attached directly to an oxygen atom, wherein a suitable alkyl group as defined above is attached to a sulfonyl radical;

the "mono-substituted amino" group used either alone or in combination with other radicals, represents an amino group substituted with one group selected from $(C_1-C_6)$ alkyl, substituted alkyl, aryl, substituted aryl or arylalkyl groups as defined earlier, more preferably such groups are selected from methylamine, ethylamine, n-propylamine, n-butylamine, n-pentylamine and the like;

the 'disubstituted amino" group used either alone or in combination with other radicals, represents an amino group, substituted with two radicals that may be same or different selected from $(C_1-C_6)$alkyl, substituted alkyl, aryl, substituted aryl, or arylalkyl groups, as defined above, more preferably the groups are selected from dimethylamino, methylethylamino, diethylamino, phenylmethyl amino and the like;

Suitable groups and substituents on the groups may be selected from those described anywhere in the specification.

Preferred compounds according to the present invention include but not limited to:

2-(1-(benzyloxy)-4-hydroxy-2-oxo-1,2-dihydroquinoline-3-carboxamido)acetic acid;
2-(1-(cyclopropylmethoxy)-4-hydroxy-2-oxo-1,2-dihydroquinoline-3-carboxamido)acetic acid;
1-(cyclopropylmethoxy)-4-hydroxy-N-(2-(methylsulfonamido)-2-oxoethyl)-2-oxo-1,2-dihydroquinoline-3-carboxamide;
2-(4-hydroxy-2-oxo-1-((4-(trifluoromethyl)benzyl)oxy)-1,2-dihydro-1,8-naphthyridine-3-carboxamido)acetic acid;
2-(1,4-dihydroxy-2-oxo-1,2-dihydroquinoline-3-carboxamido)acetic acid;
2-(1-(benzo[d]thiazol-2-ylmethoxy)-4-hydroxy-2-oxo-1,2-dihydroquinoline-3-carboxamido)acetic acid;
2-(4-hydroxy-2-oxo-1-((2-(trifluoromethyl)thiazol-4-yl)methoxy)-1,2-dihydroquinoline-3-carboxamido)acetic acid;
2-(1-(allyloxy)-4-hydroxy-2-oxo-6-phenoxy-1,2-dihydroquinoline-3-carboxamido) acetic acid;
2-(1-(allyloxy)-4-hydroxy-2-oxo-6-phenyl-1,2-dihydroquinoline-3-carboxamido) acetic acid;
2-(4-(allyloxy)-7-hydroxy-5-oxo-4,5-dihydrothieno[3,2-b]pyridine-6-carboxamido) acetic acid;
2-(4-hydroxy-1-methoxy-2-oxo-1,2-dihydroquinoline-3-carboxamido)acetic acid;
2-(4-hydroxy-2-oxo-1-((4-(trifluoromethyl)benzyl)oxy)-1,2-dihydroquinoline-3-carboxamido)acetic acid;
2-(4-hydroxy-2-oxo-1-((2-(trifluoromethyl)benzyl)oxy)-1,2-dihydroquinoline-3-carboxamido)acetic acid;
2-(4-hydroxy-2-oxo-1-(pyridin-2-ylmethoxy)-1,2-dihydroquinoline-3-carboxamido) acetic acid;
2-(1-(allyloxy)-4-hydroxy-2-oxo-1,2-dihydroquinoline-3-carboxamido)acetic acid;
2-(1-(((2,6-difluorobenzyl)oxy)-4-hydroxy-2-oxo-1,2-dihydroquinoline-3-carboxamido)acetic acid;
2-(1-(benzyloxy)-7-chloro-4-hydroxy-2-oxo-1,2-dihydroquinoline-3-carboxamido) acetic acid;
2-(7-chloro-4-hydroxy-2-oxo-1-((4-(trifluoromethyl)benzyl)oxy)-1,2-dihydroquinoline-3-carboxamido)acetic acid;
2-(1-(allyloxy)-7-chloro-4-hydroxy-2-oxo-1,2-dihydroquinoline-3-carboxamido) acetic acid;
2-(7-chloro-1-((2,6-difluorobenzyl)oxy)-4-hydroxy-2-oxo-1,2-dihydroquinoline-3-carboxamido)acetic acid;
2-(4-hydroxy-2-oxo-1-propoxy-1,2-dihydroquinoline-3-carboxamido) acetic acid;
2-(1-((3,5-dimethylbenzyl)oxy)-4-hydroxy-2-oxo-1,2-dihydroquinoline-3-carboxamido)acetic acid;
2-(1-((4-fluorobenzyl)oxy)-4-hydroxy-2-oxo-1,2-dihydroquinoline-3-carboxamido)acetic acid;
2-(1-((4-cyanobenzyl)oxy)-4-hydroxy-2-oxo-1,2-dihydroquinoline-3-carboxamido)acetic acid;
2-(4-hydroxy-1-isopropoxy-2-oxo-1,2-dihydroquinoline-3-carboxamido)acetic acid;
2-(1-((2-cyanobenzyl)oxy)-4-hydroxy-2-oxo-1,2-dihydroquinoline-3-carboxamido)acetic acid;
2-(1-(allyloxy)-4-hydroxy-2-oxo-1,2-dihydro-1,8-naphthyridine-3-carboxamido)acetic acid;
2-(4-hydroxy-1-isobutoxy-2-oxo-1,2-dihydroquinoline-3-carboxamido)acetic acid;
2-(1-(cyclopropylmethoxy)-4-hydroxy-6-methoxy-2-oxo-1,2-dihydroquinoline-3-carboxamido)acetic acid;
2-(1-(allyloxy)-6-chloro-4-hydroxy-2-oxo-1,2-dihydroquinoline-3-carboxamido)acetic acid;
2-(1-(allyloxy)-5-fluoro-4-hydroxy-2-oxo-1,2-dihydroquinoline-3-carboxamido)acetic acid;
2-(1-(cyclopropylmethoxy)-4-hydroxy-2-oxo-1,2-dihydro-1,6-naphthyridine-3-carboxamido)acetic acid;
2-(1-(allyloxy)-4-hydroxy-6-methoxy-2-oxo-1,2-dihydroquinoline-3-carboxamido)acetic acid;
2-(4-hydroxy-6-methoxy-2-oxo-1-(prop-2-yn-1-yloxy)-1,2-dihydroquinoline-3-carboxamido)acetic acid;
2-(5-(cyclopropylmethoxy)-8-hydroxy-6-oxo-5,6-dihydropyrido[2,3-b]pyrazine-7-carboxamido)acetic acid;
2-(5-((2,6-difluorobenzyl)oxy)-8-hydroxy-6-oxo-5,6-dihydropyrido[2,3-b]pyrazine-7-carboxamido)acetic acid;
2-(1-(cyclopropylmethoxy)-4-hydroxy-2-oxo-6-phenoxy-1,2-dihydroquinoline-3-carboxamido)acetic acid;
2-(4-hydroxy-2-oxo-1-(pentan-3-yloxy)-1,2-dihydroquinoline-3-carboxamido)acetic acid;
2-(4-(allyloxy)-7-hydroxy-3-methyl-5-oxo-4,5-dihydrothieno[3,2-b]pyridine-6-carboxamido)acetic acid;
2-(7-hydroxy-3-methyl-5-oxo-4-propoxy-4,5-dihydrothieno[3,2-b]pyridine-6-carboxamido)acetic acid;
2-(4,7-dihydroxy-3-methyl-5-oxo-4,5-dihydrothieno[3,2-b]pyridine-6-carboxamido)acetic acid;
2-(4-((2,6-difluorobenzyl)oxy)-7-hydroxy-3-methyl-5-oxo-4,5-dihydrothieno[3,2-b]pyridine-6-carboxamido)acetic acid;
2-(4-hydroxy-1-(2-(methylthio)ethoxy)-2-oxo-1,2-dihydroquinoline-3-carboxamido)acetic acid;
2-(1-(cyclohexylmethoxy)-4-hydroxy-2-oxo-1,2-dihydroquinoline-3-carboxamido)acetic acid;
(S)-2-(1-(cyclopropylmethoxy)-4-hydroxy-2-oxo-1,2-dihydroquinoline-3-carboxamido)propanoic acid;
2-(8-((2,6-difluorobenzyl)oxy)-5-hydroxy-7-oxo-7,8-dihydropyrido[2,3-d]pyrimidine-6-carboxamido)acetic acid;
(S)-2-(1-(cyclopropylmethoxy)-4-hydroxy-2-oxo-1,2-dihydroquinoline-3-carboxamido)-2-phenylacetic acid;
2-(1-(allyloxy)-4-hydroxy-7-morpholino-2-oxo-1,2-dihydroquinoline-3-carboxamido)acetic acid;
tert-butyl-2-(1-(cyclopropylmethoxy)-4-hydroxy-2-oxo-1,2-dihydroquinoline-3-carboxamido)acetate;
2-(7-chloro-1-(cyclopropylmethoxy)-4-hydroxy-2-oxo-1,2-dihydroquinoline-3-carboxamido)acetic acid;
2-(1-(cyclopentylmethoxy)-4-hydroxy-2-oxo-1,2-dihydroquinoline-3-carboxamido)acetic acid;
2-(1-(cyclopentyloxy)-4-hydroxy-2-oxo-1,2-dihydroquinoline-3-carboxamido)acetic acid;
Methyl-2-(1-(cyclopropylmethoxy)-4-hydroxy-2-oxo-1,2-dihydroquinoline-3-carboxamido)acetate;
(S)-2-(1-(cyclopropylmethoxy)-4-hydroxy-2-oxo-1,2-dihydroquinoline-3-carboxamido)-4-methylpentanoic acid;
(S)-2-(1-(cyclopropylmethoxy)-4-hydroxy-2-oxo-1,2-dihydroquinoline-3-carboxamido)-3-methylbutanoic acid;
3-(1-(cyclopropylmethoxy)-4-hydroxy-2-oxo-1,2-dihydroquinoline-3-carboxamido)propanoic acid;
2-(1-(allyloxy)-4-hydroxy-2-oxo-7-phenoxy-1,2-dihydroquinoline-3-carboxamido)acetic acid;
(S)-2-(1-(cyclopropylmethoxy)-4-hydroxy-2-oxo-1,2-dihydroquinoline-3-carboxamido)-3-phenylpropanoic acid;
(S)-4-(1-(cyclopropylmethoxy)-4-hydroxy-2-oxo-1,2-dihydroquinoline-3-carboxamido)-2-hydroxybutanoic acid;
5-(1-(cyclopropylmethoxy)-4-hydroxy-2-oxo-1,2-dihydroquinoline-3-carboxamido)pentanoic acid;
2-(4-hydroxy-2-oxo-1-(prop-2-yn-1-yloxy)-1,2-dihydroquinoline-3-carboxamido)acetic acid;
2-(1-((2-fluorobenzyl)oxy)-4-hydroxy-2-oxo-1,2-dihydroquinoline-3-carboxamido)acetic acid;
2-(1-ethoxy-4-hydroxy-2-oxo-1,2-dihydroquinoline-3-carboxamido)acetic acid;
2-(4-hydroxy-2-oxo-1-((4-(trifluoromethoxy)benzyl)oxy)-1,2-dihydroquinoline-3-carboxamido)acetic acid;

2-(1-((2,4-difluorobenzyl)oxy)-4-hydroxy-2-oxo-1,2-dihydroquinoline-3-carboxamido)acetic acid;
2-(1-((2,6-difluorobenzyl)oxy)-4-hydroxy-2-oxo-1,2-dihydro-1,8-naphthyridine-3-carboxamido)acetic acid;
2-(4-hydroxy-1-((4-methoxybenzyl)oxy)-2-oxo-1,2-dihydroquinoline-3-carboxamido) acetic acid;
2-(1-(cyclopropylmethoxy)-4-hydroxy-2-oxo-1,2-dihydro-1,8-naphthyridine-3-carboxamido)acetic acid;
2-(4-hydroxy-2-oxo-1-(2,2,2-trifluoroethoxy)-1,2-dihydroquinoline-3-carboxamido) acetic acid;
2-(1-(cyclopropylmethoxy)-4-hydroxy-2-oxo-1,2-dihydro-1,7-naphthyridine-3-carboxamido)acetic acid;
2-(6-cyano-1-(cyclopropylmethoxy)-4-hydroxy-2-oxo-1,2-dihydroquinoline-3-carboxamido)acetic acid;
2-(8-(benzyloxy)-5-hydroxy-7-oxo-7,8-dihydropyrido[2,3-d]pyrimidine-6-carboxamido)acetic acid;
(S)-2-(4-hydroxy-2-oxo-1-propoxy-1,2-dihydroquinoline-3-carboxamido)propanoic acid;
2-(4-hydroxy-1-(2-methoxyethoxy)-2-oxo-1,2-dihydroquinoline-3-carboxamido) acetic acid;
2-(4-hydroxy-2-oxo-6-phenoxy-1-propoxy-1,2-dihydroquinoline-3-carboxamido) acetic acid;
2-(1-((4-cyclopropylbut-3-en-1-yl)oxy)-4-hydroxy-2-oxo-1,2-dihydroquinoline-3-carboxamido)acetic acid;
2-(1-(heptan-4-yloxy)-4-hydroxy-2-oxo-1,2-dihydroquinoline-3-carboxamido)acetic acid;
Ethyl-2-(4-(cyclopropylmethoxy)-7-hydroxy-5-oxo-4,5-dihydrothieno[3,2-b]pyridine-6-carboxamido)acetate;
2-(4-(cyclopropylmethoxy)-7-hydroxy-5-oxo-4,5-dihydrothieno[3,2-b]pyridine-6-carboxamido)acetic acid;
2-(1-(heptyloxy)-4-hydroxy-2-oxo-1,2-dihydroquinoline-3-carboxamido)acetic acid;
2-(4-hydroxy-2-oxo-1-((6-(trifluoromethyl)pyridin-3-yl)methoxy)-1,2-dihydroquinoline-3-carboxamido)acetic acid;
2-(4-hydroxy-2-oxo-1-(4-(trifluoromethyl)phenoxy)-1,2-dihydroquinoline-3-carboxamido)acetic acid;
2-(4-hydroxy-2-oxo-1-(4-(trifluoromethyl)phenethoxy)-1,2-dihydroquinoline-3-carboxamido)acetic acid;
2-(4-hydroxy-2-oxo-1-(4-(trifluoromethyl)phenethoxy)-1,2-dihydro-1,8-naphthyridine-3-carboxamido)acetic acid;
2-(1-(but-2-yn-1-yloxy)-4-hydroxy-2-oxo-1,2-dihydroquinoline-3-carboxamido)acetic acid;
2-(4-hydroxy-2-oxo-1-(3,3,3-trifluoropropoxy)-1,2-dihydroquinoline-3-carboxamido)acetic acid;
2-(1-(2-amino-2-oxoethoxy)-4-hydroxy-2-oxo-1,2-dihydroquinoline-3-carboxamido)acetic acid;
2-(1-(benzo[d]oxazol-2-ylmethoxy)-4-hydroxy-2-oxo-1,2-dihydroquinoline-3-carboxamido)acetic acid;
2-(1-(benzo[d]thiazol-2-ylmethoxy)-6-chloro-4-hydroxy-2-oxo-1,2-dihydroquinoline-3-carboxamido)acetic acid;
2-(1-(allyloxy)-4-hydroxy-8-methoxy-2-oxo-1,2-dihydroquinoline-3-carboxamido)acetic acid;
2-(1-ethoxy-4-hydroxy-8-methoxy-2-oxo-1,2-dihydroquinoline-3-carboxamido)acetic acid;
2-(4-hydroxy-1-(oxazol-2-ylmethoxy)-2-oxo-1,2-dihydroquinoline-3-carboxamido)acetic acid;
2-(1-(allyloxy)-6-cyano-4-hydroxy-2-oxo-1,2-dihydroquinoline-3-carboxamido)acetic acid;
2-(1-(allyloxy)-4-hydroxy-6-nitro-2-oxo-1,2-dihydroquinoline-3-carboxamido)acetic acid;
2-(4-hydroxy-1-methoxy-2-oxo-6-(trifluoromethyl)-1,2-dihydroquinoline-3-carboxamido)acetic acid;
2-(4,6-dihydroxy-2-oxo-1-propoxy-1,2-dihydroquinoline-3-carboxamido)acetic acid;
2-(1-((4-(tert-butyl)benzyl)oxy)-4-hydroxy-2-oxo-1,2-dihydroquinoline-3-carboxamido)acetic acid;
2-(1-([1,1-biphenyl]-4-ylmethoxy)-4-hydroxy-2-oxo-1,2-dihydroquinoline-3-carboxamido)acetic acid;
2-(4-hydroxy-1-((4-(oxazol-2-yl)benzyl)oxy)-2-oxo-1,2-dihydroquinoline-3-carboxamido)acetic acid;
2-(1-(benzyloxy)-4-hydroxy-2-oxo-6-phenoxy-1,2-dihydroquinoline-3-carboxamido)acetic acid;
2-(1-(benzyloxy)-4-hydroxy-2-oxo-6-(pyridin-2-yloxy)-1,2-dihydroquinoline-3-carboxamido)acetic acid;
2-(1-(benzyloxy)-4-hydroxy-2-oxo-6-(phenylthio)-1,2-dihydroquinoline-3-carboxamido)acetic acid;
2-(1-(benzyloxy)-4-hydroxy-6-(methylsulfonyl)-2-oxo-1,2-dihydroquinoline-3-carboxamido)acetic acid;
2-(1-(benzyloxy)-4-hydroxy-2-oxo-6-phenyl-1,2-dihydroquinoline-3-carboxamido)acetic acid;
2-(1-(benzyloxy)-4-hydroxy-6-(4-methoxyphenyl)-2-oxo-1,2-dihydroquinoline-3-carboxamido)acetic acid;
2-(1-(benzyloxy)-4-hydroxy-6-(5-methoxypyridin-2-yl)-2-oxo-1,2-dihydroquinoline-3-carboxamido)acetic acid;
2-(1-(benzyloxy)-4-hydroxy-2-oxo-6-sulfamoyl-1,2-dihydroquinoline-3-carboxamido)acetic acid;
2-(1-(benzyloxy)-4-hydroxy-6-(methylsulfonamido)-2-oxo-1,2-dihydroquinoline-3-carboxamido)acetic acid;
2-(1-(benzyloxy)-4-hydroxy-2-oxo-6-(trifluoromethoxy)-1,2-dihydroquinoline-3-carboxamido)acetic acid;
2-(6-benzoyl-4-hydroxy-2-oxo-1-((4-(trifluoromethyl)benzyl)oxy)-1,2-dihydroquinoline-3-carboxamido)acetic acid;
2-(1-(benzyloxy)-4-hydroxy-N-methyl-2-oxo-1,2-dihydroquinoline-3-carboxamido)acetic acid;
2-(1-(benzyloxy)-4-hydroxy-2-oxo-1,2-dihydroquinoline-3-carboxamido)-2-methylpropanoic acid;
1-(1-(benzyloxy)-4-hydroxy-2-oxo-1,2-dihydroquinoline-3-carboxamido)cyclopropanecarboxylic acid;
3-(1-(benzyloxy)-4-hydroxy-2-oxo-1,2-dihydroquinoline-3-carboxamido)propanoic acid;
1-(benzyloxy)-4-hydroxy-N-(2-(methylsulfonamido)-2-oxoethyl)-2-oxo-1,2-dihydroquinoline-3-carboxamide;
1-(benzyloxy)-4-hydroxy-2-oxo-N-(2-oxo-2-(thiophene-2-carboxamido)ethyl)-1,2-dihydroquinoline-3-carboxamide;
2-(4-hydroxy-1-methoxy-2-oxo-1,2-dihydro-1,5-naphthyridine-3-carboxamido)acetic acid;
2-(8-hydroxy-5-methoxy-6-oxo-5,6-dihydropyrido[2,3-b]pyrazine-7-carboxamido)acetic acid;
2-(7-hydroxy-4-methoxy-5-oxo-4,5-dihydrofuro[3,2-b]pyridine-6-carboxamido)acetic acid;
2-(4-(cyclopropylmethoxy)-7-hydroxy-5-oxo-4,5-dihydrofuro[3,2-b]pyridine-6-carboxamido)acetic acid;
2-(7-hydroxy-5-oxo-4-propoxy-4,5-dihydrofuro[3,2-b]pyridine-6-carboxamido)acetic acid;
2-(7-hydroxy-4-methoxy-5-oxo-4,5-dihydrothieno[3,2-b]pyridine-6-carboxamido)acetic acid;
2-(7-hydroxy-4-methoxy-1-methyl-5-oxo-4,5-dihydro-1H-pyrrolo[3,2-b]pyridine-6-carboxamido)acetic acid;
2-(7-hydroxy-1-methyl-5-oxo-4-propoxy-4,5-dihydro-1H-pyrrolo[3,2-b]pyridine-6-carboxamido)acetic acid;
2-(7-hydroxy-4-methoxy-5-oxo-4,5-dihydrothiazolo[4,5-b]pyridine-6-carboxamido)acetic acid;
2-(7-hydroxy-5-oxo-4-propoxy-4,5-dihydrothiazolo[5,4-b]pyridine-6-carboxamido)acetic acid;
2-(4-hydroxy-7-methoxy-1-methyl-6-oxo-6,7-dihydro-1H-pyrazolo[3,4-b]pyridine-5-carboxamido)acetic acid;
2-(7-hydroxy-4-methoxy-5-oxo-4,5-dihydrooxazolo[4,5-b]pyridine-6-carboxamido)acetic acid;
2-(7-hydroxy-5-oxo-4-propoxy-4,5-dihydrooxazolo[4,5-b]pyridine-6-carboxamido)acetic acid;

2-(4-hydroxy-1-methoxy-2-oxo-1,2,5,7-tetrahydrothieno[3,4-b]pyridine-3-carboxamido)acetic acid;
2-(7-ethoxy-4-hydroxy-6-oxo-6,7-dihydrothieno[2,3-b]pyridine-5-carboxamido)acetic acid;
2-(7-(cyclopropylmethoxy)-4-hydroxy-6-oxo-6,7-dihydrothieno[2,3-b]pyridine-5-carboxamido)acetic acid;
2-(4-hydroxy-1-methoxy-6,6-dioxido-2-oxo-1,2,5,7-tetrahydrothieno[3,4-b]pyridine-3-carboxamido)acetic acid;
2-(7-ethoxy-4-hydroxy-1-methyl-6-oxo-6,7-dihydro-1H-pyrazolo[3,4-b]pyridine-5-carboxamido)acetic acid;
2-(7-ethoxy-4-hydroxy-6-oxo-1-phenyl-6,7-dihydro-1H-pyrazolo[3,4-b]pyridine-5-carboxamido)acetic acid;
2-(7-ethoxy-4-hydroxy-3-methyl-6-oxo-6,7-dihydroisothiazolo[5,4-b]pyridine-5-carboxamido)acetic acid;
2-(4-hydroxy-2-oxo-1-(2-(2-oxooxazolidin-3-yl)ethoxy)-1,2-dihydroquinoline-3-carboxamido)acetic acid;
2-(4-hydroxy-2-oxo-1-((4-(trifluoromethyl)benzyl)oxy)-1,2,5,6,7,8-hexahydroquinoline-3-carboxamido)acetic acid;
2-(4-hydroxy-2-oxo-1-propoxy-1,2,5,6,7,8-hexahydroquinoline-3-carboxamido)acetic acid;

The compounds of the present invention can be formulated by using suitable excipients and formulating agents as are known in the art. Such formulations will depend on the route, dose of administration and also on the patient profile. A skilled person is well equipped in formulating the compounds of the present invention based on these and other factors which needs to be considered keeping the best interest of the patients in mind.

The novel compounds of this invention may be prepared using the reactions and techniques as shown in scheme below and described in this section. The reactions are performed in solvents appropriate to the reagents and materials employed and are suitable for the transformations being affected. It is understood by those skilled in the art that the nature and order of the synthetic steps presented may be varied for the purpose of optimizing the formation of the compounds of the present invention. It will also be well appreciated that one or more of the reactants may be protected and deprotected for facile synthesis by techniques known to persons skilled in the art. It will also be appreciated that one or more of the compounds of the present invention may exist in stereoisomeric and/or diastereomeric forms. Such stereoisomers and/or diastereomers as well as their optical antipodes are to be construed to be within the scope of the present invention. It will also be well appreciated that one or more of these compounds may be converted to their salts and other derivatives based on the specific groups present on the compounds, which can be well comprehended by persons skilled in the art. Such salts and/or other derivatives, as the case may be should also be construed to be within the scope of the present invention.

Scheme 1: Synthesis of compounds of general formula (I)

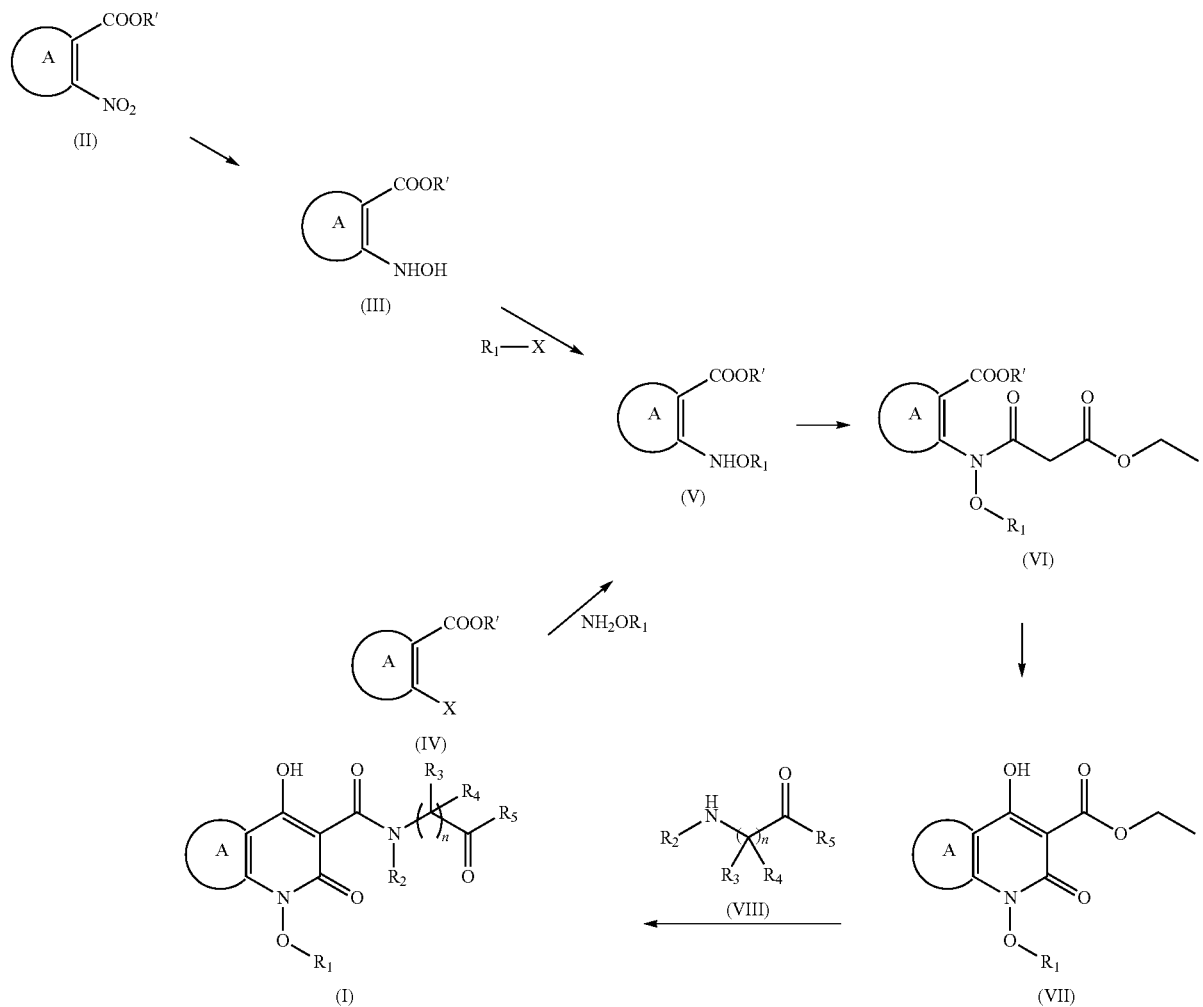

wherein 'X' denotes a suitable leaving group such as halogen, mesyl etc. R' represents suitable alkyl or aralkyl group such as methyl, ethyl, n-butyl, benzyl and the like.

The compound (III) can be obtained by partial reduction of nitro group of compound (II) using general techniques described in literature. Preferred methods involve reduction using metals in presence of acids. The most preferred techniques involve reduction using Zn metal in presence of mild acidic environment provided by $NH_4Cl$ in solvents such as alcohols, THF, acetonitrile, water etc or treatment with stannous chloride dihydrate and sodium acetate trihydrate in solvent mixture of $THF:CH_3OH$. The preferred temperature for reaction ranges from 0° C. to 60° C.

The compounds of general formula (V) can be obtained by alkylation of (III) by appropriate reagent of the formula $R_1$—X, wherein. $R_1$ & 'X' are as defined earlier, using various techniques reported in literature. Most preferred techniques involves alkylation in presence of bases such as sodium carbonate, potassium carbonate, cesium carbonate, sodium hydride etc. in protic solvents such as alcohols and aprotic solvents such as THF, acetonitrile, DMF etc.

Alternatively, compounds of general formula (V) can also be obtained by direct displacement of leaving group 'X' from compounds of general formula (IV) with O-substituted hydroxylamine derivative ($NH_2OR_1$). The displacement techniques involves reaction of (IV) with $NH_2OR_1$ in presence or absence of organic bases such as TEA, DIPEA etc. in presence or absence of solvents such as dioxane, DMF, toluene etc. The reaction temperature ranges from 25° C. to 150° C.

The compounds of general formula (VI) can be obtained by reacting (V) with ethyl malonyl chloride using various techniques reported in literature for acid chloride coupling. The preferred technique involves reaction using organic bases such as TEA, DIPEA, pyridine etc. in solvents such as DCM, EDC etc. The compounds of general formula (VI) can also be prepared by reacting (V) with ethyl hydrogen malonate using $POCl_3$-pyridine coupling method in presence or absence of solvent(s) such as DCM, EDC $CH_3CN$ and the like at 0-25° C.

The compounds of the formula (VII) can be obtained by cyclisation of (VI) using strong bases such as metal alkoxides ($NaOCH_3$, $NaOC_2H_5$, potassium tert-butoxide and the like) in solvent(s) such as methanol, ethanol, tert-butanol and the like. The preferred temperature ranges from 0-40° C.

The compounds of general formula (I) can be obtained by amidation of (VII) with suitable amine derivative (VIII) using various techniques reported in literature.

Preferred methods involves heating (VII) with (VIII) in presence or absence of organic bases such as TEA, DIPEA and the like and in presence or absence of solvent(s) such as dioxane, toluene, xylene etc. When (VIII) represents an amino acid derivative, preferred method utilizes equimolar base such as sodium methoxide with respect to amino acid derivative and solvent(s) such as dioxane, toluene and the like. Alternatively, ester derivatives of amino acid can be coupled with (VII) using methods described above followed by hydrolysis of ester group using strong bases such as NaOH, KOH etc. in solvent(s) such as water, THF, methanol or mixture thereof.

The invention is explained in greater detail by the examples given below, which are provided by way of illustration only and therefore should not be construed to limit the scope of the invention.

1H NMR spectral data given in the examples (vide infra) are recorded using a 400 MHz spectrometer (Bruker Topspin 2.0) and reported in δ scale. Tetramethyl silane is used as the internal standard.

Example 1

Preparation of 2-(1-(benzyloxy)-4-hydroxy-2-oxo-1, 2-dihydroquinoline-3-carboxamido)acetic acid

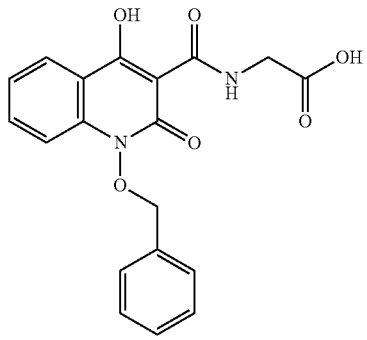 [SMILES: O=C(O)CNC(=O)c1c(O)c2ccccc2n(OCc2ccccc2)c1=O]

Step 1: Preparation of ethyl 2-(hydroxyamino)benzoate

To a stirring solution of ethyl 2-nitrobenzoate (32.0 g, 0.164 mol), ammonium chloride (22.28 g, 0.416 mol) in solvent mixture of water (240 mL) and THF (288 mL) was added zinc powder (26.8 g, 0.410 mol) slowly at 0° C. Reaction mixture was stirred at 0° C.-10° C. for 2 h. Reaction mixture was then diluted with water followed by DCM and filtered through Hyflow bed. The organic layer was separated and distilled out to get crude product which was column purified using 0-5% EtOAC in hexane to get titled compound as light yellow solid in 50% yield.

$^1$HNMR (DMSO-$d_6$): 1.30 (t, J=7 Hz, 3H), 4.24-4.30 (q, J=7.2 Hz, 2H), 6.77-6.81 (m, 1H), 7.25-7.27 (dd, J=0.4 and 7.6 Hz, 1H), 7.46-7.50 (m, 1H), 7.78-7.780 (dd, J=1.6 and 8.0 Hz, 1H), 8.88 (d, J=1.6 Hz, 1H), 9.16 (s, 1H).

Step 2: Preparation of ethyl 2-(benzyloxyamino)benzoate

To a stirring suspension of benzyl bromide (1.038 g, 6.07 mmol) and cesium carbonate (2.70 g, 8.28 mmol) in DMF (4 mL) was added ethyl 2-(hydroxyamino)benzoate (1.0 g, 5.52 mmol) dissolved in 2 mL DMF at RT and stirred for 1 h. Reaction mixture was diluted with water and extracted with EtOAC. The organic layer was separated and distilled out to get crude product which was column purified using 0-3% EtOAC in hexane to get the titled compound in 72% yield.

$^1$HNMR (DMSO-$d_6$): 1.28 (t, J=7.2 Hz, 3H), 4.22-4.27 (q, J=7.2 Hz, 2H), 4.89 (s, 2H), 6.86-6.90 (m, 1H), 7.27 (d, J=8.4 Hz, 1H), 7.36-7.43 (m, 3H), 7.45-7.48 (dd, J=1.6 and 8.0 Hz, 2H), 7.50-7.54 (m, 1H), 7.81-7.83 (dd, J=1.6 and 8.0 Hz, 1H), 9.76 (s, 1H).

Step 3: Preparation of ethyl 2-(N-(benzyloxy)-3-ethoxy-3-oxopropanamido)benzoate To a stirring solution of ethyl hydrogen malonate (0.6 g, 4.54 mmol) and ethyl 2-(benzyloxyamino)benzoate (1.12 g, 4.13 mmol) in acetonitrile (10 mL) was added pyridine (1.3 g, 16.51 mmol) and reaction mixture was cooled to 0-10° C. To this was added POCl₃ (0.423 mL, 4.54 mmol), at 0-10° C. in 15-30 min. and stirring continued for 1 h. Reaction mixture was diluted with DCM and washed with water. Organic layer was separated and distilled out to get crude product which was column purified using 15% EtOAC in hexane to get titled compound in 79% yield.

¹HNMR (DMSO-d₆): 1.14 (t, J=7.2 Hz, 3H), 1.25 (t, J=7.2 Hz, 3H), 3.69 (s, 2H), 4.05-4.10 (q, J=7.0 Hz, 2H), 4.19-4.24 (q, J=7.2 Hz, 2H), 4.88 (s, 2H), 7.36 (m, 5H), 7.46-7.51 (m, 2H), 7.66-7.70 (m, 1H), 7.77 (d, J=7.2 Hz, 1H).

Step 4: Preparation of ethyl 1-(benzyloxy)-4-hydroxy-2-oxo-1,2-dihydroquinoline-3-carboxylate To a stirring solution of ethyl 2-(N-(benzyloxy)-3-ethoxy-3-oxopropanamido)benzoate (1.3 g, 3.37 mmol) in MeOH (10 mL) was added sodium methoxide (0.255 g, 4.72 mmol) slowly at 20-25° C. Reaction mixture was stirred for 1 h. Excess methanol was distilled out and then reaction mixture diluted with NH₄CJ solution. Precipitated product was filtered and dried to get titled compound in 58% yield.

¹HNMR (DMSO-d₆): 1.31 (t, J=7.0 Hz, 3H), 4.26-4.31 (q, J=7.0 Hz, 2H), 5.11 (s, 2H), 7.24 (d, J=8.0 Hz, 1H), 7.41-7.49 (m, 4H), 7.60-7.62 (dd, J=1.6 and 7.6 Hz, 2H), 7.66 (d, J=7.2 Hz, 1H) 8.01-8.04 (dd, J=1.2 and 8.0 Hz, 1H).

Step 5: Preparation of ethyl 2-(1-(benzyloxy)-4-hydroxy-2-oxo-1,2-dihydroquinoline-3-carboxamido) acetate To a stirring suspension of ethyl 1-(benzyloxy)-4-hydroxy-2-oxo-1,2-dihydroquinoline-3-carboxylate (700 mg, 2.063 mmol), ethyl 2-aminoacetate hydrochloride (387 mg, 2.77 mmol) in dioxane (5 mL) was added DIPEA (0.660 ml, 3.78 mmol). Reaction mixture was heated at 100° C. for 12 h. Solvent from reaction mixture was distilled out to get crude product which was then column purified using 15% EtOAC in hexane to get titled product in 37% yield.

¹HNMR (DMSO-d₆): 1.23 (t, J=7.2 Hz, 3H), 4.14-4.20 (q, J=7.2 Hz, 2H), 4.23 (d, J=5.6 Hz, 2H), 5.22 (s, 2H), 7.40-7.47 (m, 4H), 7.63-7.67 (m, 3H), 7.84-7.88 (m, 1H), 8.10-8.12 (dd, J=1.2 and 8.0 Hz, 1H), 10.33 (t, J=5.8 Hz, 1H).

Step 6: Preparation of 2-(1-(benzyloxy)-4-hydroxy-2-oxo-1,2-dihydroquinoline-3-carboxamido)acetic acid To a stirring solution of ethyl 2-(1-(benzyloxy)-4-hydroxy-2-oxo-1,2-dihydroquinoline-3-carboxamido)acetate (500 mg, 1.261 mmol) in THF (5 mL) was added solution of sodium hydroxide (126 mg, 3.15 mmol) in water (5 mL) and stirred at 25-30° C. for 2 h. Organic solvent was distilled out followed by addition of ice cold water. Reaction mixture was then acidified using dil. HCl up to pH-2-3. Precipitated solid was filtered to get titled compound in 80% yield.

¹HNMR (DMSO-d₆): 4.17 (d, J=6 Hz, 2H), 5.22 (s, 2H), 7.39-7.46 (m, 4H), 7.63-7.66 (m, 3H), 7.83-7.85 (dd, J=2 and 7.6 Hz, 1H), 8.10-8.13 (dd, J=1.2 and 8 Hz, 1H), 10.29 (t, 1H).

Example 2

Preparation of 2-(1-(cyclopropylmethoxy)-4-hydroxy-2-oxo-1,2-dihydroquinoline-3-carboxamido) acetic acid

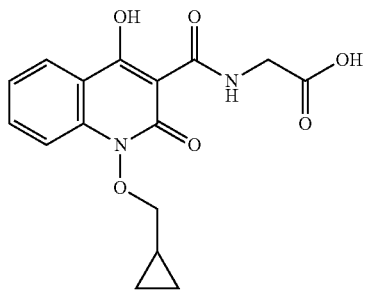 [SMILES: O=C(O)CNC(=O)c1c(O)c2ccccc2n(OCC2CC2)c1=O]

Step 1: Preparation of (iodomethyl)cyclopropane

To a stirring solution of cyclopropylmethanol (30 g, 0.416 mol) in solvent acetone (60 mL) was added methanesulfonyl chloride (35.7 ml, 0.46 mol) and reaction mixture was cooled to −15 to −20° C. To this was added solution of TEA (63.8 ml, 0.46 mol) in acetone (60 mL) at −15 to −20° C. in 2 h and stirring continued for further 1 h. Precipitated salt was filtered. The filtrate was diluted with acetone (600 mL) and transferred to another flask. To this was added sodium iodide (68.6 g, 0.46 mol) at RT and refluxed for 5 h. Reaction mixture was diluted with water and extracted with hexane. The organic layer was washed with sodium thiosulphate, separated and distilled out to get titled compound as yellow liquid in 66% yield.

¹HNMR (CDCl₃): 0.29-0.31 (m, 2H), 0.79-0.83 (m, 2H), 1.29-1.33 (m, 1H), 3.11 (d, J=7.6 Hz, 2H).

Step 2: Preparation of ethyl 2-(hydroxyamino)benzoate

To a stirring solution of ethyl 2-nitrobenzoate (1.0 g, 5.12 mmol), sodium acetate trihydrate (4.18 g, 30.7 mmol) in solvent mixture of MeOH (7 ml) and THF (7 ml) was added stannous chloride dihydrate (3.47 g, 15.37 mmol) slowly at 10-20° C. Reaction mixture was stirred at 25-30° C. for 16 h. Reaction mixture was diluted with water and basified with aq. sodium bicarbonate solution. Product was extracted with ethyl acetate. The organic layer was separated and distilled out to get crude product which was stirred with hexane to get white solid in 80% yield.

Step 3: Preparation of ethyl 2-((cyclopropylmethoxy)amino)benzoate

The titled compound was prepared using similar procedure as that of Example-1 (step-2) using product of step 1 described above and ethyl 2-(hydroxyamino)benzoate in 50% yield.

¹HNMR (DMSO-d₆): 0.31 (m, 2H), 0.52-0.56 (m, 2H), 1.10-1.17 (m, 1H), 3.31 (t, J=7.0 Hz, 3H), 3.67 (d, J=6.8 Hz, 2H), 4.25-4.30 (q, J=7.0 Hz, 2H), 6.86 (t, J=7.6 Hz, 1H), 7.25 (d, J=8.0 Hz, 1H), 7.49-7.53 (m, 1H), 7.81-7.83 (dd, J=1.6 and 8.0 Hz, 1H) 9.27 (s, 1H).

Step 4: Preparation of ethyl 2-(N-(cyclopropylmethoxy)-3-ethoxy-3-oxopropanamido)benzoate The titled compound was prepared using similar procedure as that of Example-1 (step-3) using product of step 3 described above in 85% yield.

$^1$HNMR (DMSO-$d_6$): 0.22-0.25 (m, 2H), 0.45-0.50 (m, 2H), 1.01-1.07 (m, 1H), 1.16-1.27 (m, 6H), 3.66 (d, J=7.6 Hz, 2H), 3.70 (s, 2H), 4.10-4.15 (q, J=7.0 Hz, 2H), 4.18-4.23 (q, J=7.2 Hz, 2H), 7.42-7.48 (m, 2H), 7.64-7.67 (m, 1H), 7.72 (d, J=7.6 Hz, 1H).

Step 5: Preparation of ethyl 1-(cyclopropylmethoxy)-4-hydroxy-2-oxo-1,2-dihydroquinoline-3-carboxylate The titled compound was prepared using similar procedure as that of Example-1 (step-4) using product of step 4 described above in 75% yield.

$^1$HNMR (DMSO-$d_6$): 0.32-0.40 (m, 2H), 0.45-0.50 (m, 2H), 1.22-1.28 (m, 1H), 1.31 (t, J=7.0 Hz, 3H), 3.96 (d, J=7.2 Hz, 2H), 4.31-4.37 (q, J=7.0 Hz, 2H), 7.31-7.35 (m, 1H), 7.61 (d, J=8.0 Hz, 1H) 7.78-7.82 (m, 1H), 8.05-8.07 (dd, J=1.2 and 8.0 Hz, 1H).

Step 6: Preparation of ethyl 2-(1-(cyclopropylmethoxy)-4-hydroxy-2-oxo-1,2-dihydroquinoline-3-carboxamido)acetate The titled compound was prepared using similar procedure as that of Example-1 (step-5) using product of step 5 described above in 70% yield.

$^1$HNMR (DMSO-$d_6$): 0.39 (m, 2H), 0.56-0.61 (m, 2H), 1.21 (t, J=7.0 Hz, 3H), 1.25-1.30 (m, 1H), 4.03 (d, J=7.6 Hz, 2H), 4.12-4.18 (q, J=7.2 Hz, 2H), 4.19 (d, J=5.6 Hz, 2H) 7.39-7.43 (m, 1H), 7.70 (d, J=8.0 Hz, 1H), 7.85-7.89 (m, 1H), 8.08-8.11 (dd, J=1.2 and 8.0 Hz, 1H), 10.27 (t, J=5.6 Hz, 1H).

Step 7: Preparation of 2-(1-(cyclopropylmethoxy)-4-hydroxy-2-oxo-1,2-dihydroquinoline-3-carboxamido)acetic acid The titled compound was prepared using similar procedure as that of Example-1 (step-6) using product of step 6 described above in 90% yield.

$^1$H NMR (DMSO-$d_6$): 0.38-0.40 (m, 2H), 0.57-0.61 (m, 2H), 1.27-1.30 (m, 1H), 4.04 (d, J=7.6 Hz, 2H), 4.12 (d, J=5.2 Hz, 2H), 7.39-7.43 (m, 1H), 7.70 (d, J=8.0 Hz, 1H), 7.85-7.89 (m, 1H), 8.09-8.11 (dd, J=1.2 and 8.0 Hz, 1H), 10.25 (t, J=5.4 Hz, 1H), 12.98 (bs, 1H).

Example 3

Preparation of 1-(cyclopropylmethoxy)-4-hydroxy-N-(2-(methylsulfonamido)-2-oxoethyl)-2-oxo-1,2-dihydroquinoline-3-carboxamide

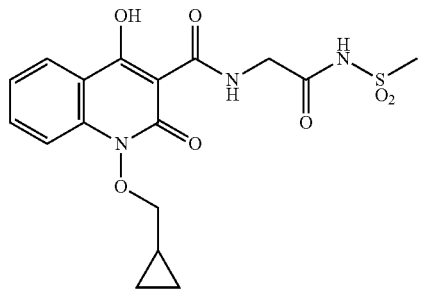 [SMILES: CS(=O)(=O)NC(=O)CNC(=O)c1c(O)c2ccccc2n(OCC2CC2)c1=O]

To a stirring solution of product of Example-2 (600 mg, 1.806 mmol) in DMF (6 mL) was added methanesulfonamide (206 mg, 2.167 mmol), DMAP (110 mg, 0.903 mmol), 4-ethylmorpholine (624 mg, 5.42 mmol) and EDCI.HCl (415 mg, 2.167 mmol). Reaction mixture was stirred at RT for 16 h. Reaction mixture was diluted with water and extracted with EtOAC. The organic layer was separated and distilled out to get crude product which was purified by preparative HPLC technique to get the titled compound in 41% yield.

$^1$H NMR (DMSO-$d_6$): 0.37-0.40 (m, 2H), 0.57-0.61 (m, 2H), 1.27-1.30 (m, 1H), 3.27 (s, 3H), 4.04 (d, J=7.2 Hz, 2H), 4.19 (d, J=5.6 Hz, 2H), 7.39-7.43 (m, 1H), 7.71 (d, J=8.4 Hz, 1H), 7.85-7.90 (m, 1H), 8.09 (dd, J=1.2 and 8.0 Hz, 1H), 10.28 (t, J=5.6 Hz, 1H), 12.06 (bs, 1H). ESI/MS m/z 410 $(M+H)^+$.

Example 4

Preparation of 2-(4-hydroxy-2-oxo-1-((4-(trifluoromethyl)benzyl)oxy)-1,2-dihydro-1,8-naphthyridine-3-carboxamido)acetic acid

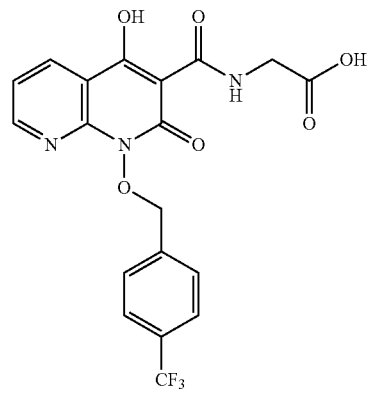 [SMILES: O=C(O)CNC(=O)c1c(O)c2cccnc2n(OCc2ccc(C(F)(F)F)cc2)c1=O]

Step 1: Preparation of 2-((4-(trifluoromethyl)benzyl)oxy)isoindoline-1,3-dione To a stirring solution of N-hydroxy phthalamide (5.25 g, 32.3 mmol) in DMF (30 mL) was added cesium carbonate (15.80 g, 48.5 mmol) and 1-(bromomethyl)-4-(trifluoromethyl)benzene (5 ml, 32.3 mmol) at RT. Reaction mixture was stirred for 3 h. and then diluted with water. Precipitated product was filtered and dried to get titled compound in 87% yield.

$^1$H NMR (DMSO-$d_6$): 5.28 (s, 2H), 7.75-7.80 (m, 4H), 7.87 (m, 4H).

Step 2: Preparation of O-(4-(trifluoromethyl)benzyl)hydroxylamine

To a stirring solution of 2-((4-(trifluoromethyl)benzyl)oxy)isoindoline-1,3-dione (9 g, 28.0 mmol) in ethanol (90 mL) was added hydrazine hydrate (1.543 g, 30.8 mmol) at RT. Reaction mixture was stirred for 16 h. Reaction mixture was filtered and filtrate was diluted with water and extracted with EtOAC. The organic layer was separated and distilled out to get the titled compound in 68% yield.

$^1$H NMR (DMSO-$d_6$): 4.65 (s, 2H), 6.17 (s, 2H), 7.53 (d, J=8.0 Hz, 2H), 7.69 (d, J=8.0 Hz, 2H).

Step 3: Preparation of ethyl 2-(((4-(trifluoromethyl) benzyl)oxy)amino)nicotinate The mixture of ethyl 2-chloronicotinate (1.4 g, 7.54 mmol) and O-(4-(trifluoromethyl)benzyl)hydroxylamine (2.163 g, 11.31 mmol) was heated at 120° C. for 6 h. Reaction mixture was diluted with water and extracted with EtOAC. The organic layer was separated and distilled out to get crude product which was column purified using 15-20% EtOAc in hexane to get the titled compound in 41% yield.

$^1$HNMR (DMSO-$d_6$): 1.27 (t, J=7.2 Hz, 3H), 4.23-4.28 (q, J=7.0 Hz, 2H), 5.09 (s, 2H), 6.93-6.96 (dd, J=4.8 and 7.6 Hz, 1H), 7.67-7.76 (m, 4H), 8.13-8.16 (dd, J=1.6 and 7.6 Hz, 1H), 8.47-8.48 (dd, J=1.6 and 7.6 Hz, 1H), 10.14 (s, 1H).

Step 4: Preparation of ethyl 2-(3-ethoxy-3-oxo-N-((4-(trifluoromethyl)benzyl)oxy) propanamido)nicotinate The titled compound was prepared using similar procedure as that of Example-1 (step-3) using product of step 3 described above in 72% yield.

$^1$HNMR (DMSO-$d_6$): 1.14 (t, J=7.0 Hz, 3H), 1.26 (t, J=7.2 Hz, 3H), 3.72 (s, 2H), 4.04-4.09 (q, J=7.2 Hz, 2H), 4.21-4.26 (q, J=7.0 Hz, 2H), 5.11 (s, 2H), 7.54-7.57 (dd, J=4.8 and 7.6 Hz, 1H), 7.59 (d, J=7.6 Hz, 2H), 7.71 (d, J=8.0 Hz, 2H), 8.20-8.23 (dd, J=1.6 and 7.6 Hz, 1H), 8.69 (d, J=3.2 Hz, 1H).

Step 5: Preparation of ethyl 4-hydroxy-2-oxo-1-((4-(trifluoromethyl)benzyl)oxy)-1,2-dihydro-1,8-naphthyridine-3-carboxylate The titled compound was prepared using similar procedure as that of Example-1 (step-4) using product of step 4 described above in 65% yield.

$^1$HNMR (DMSO-$d_6$): 1.22 (t, J=7.0 Hz, 3H), 4.07-4.12 (q, J=7.0 Hz, 2H), 5.17 (s, 2H), 7.11-7.14 (dd, J=4.8 and 7.6 Hz, 1H), 7.78 (d, J=8.0 Hz, 2H), 7.89 (d, J=8.0 Hz, 2H), 8.23 (d, J=6.4 Hz, 1H), 8.48 (d, J=3.2 Hz, 1H).

Step 6: Preparation of ethyl 2-(4-hydroxy-2-oxo-1-((4-(trifluoromethyl)benzyl)oxy)-1,2-dihydro-1,8-naphthyridine-3-carboxamido)acetate The titled compound was prepared using similar procedure as that of Example-1 (step-5) using product of step 5 described above in 56% yield.

$^1$HNMR (DMSO-$d_6$): 1.23 (t, J=7.0 Hz, 3H), 4.14-4.19 (q, J=7.2 Hz, 2H), 4.22 (d, J=6.0 Hz, 2H), 5.33 (s, 2H), 7.50-7.53 (dd, J=4.8 and 8.0 Hz, 1H), 7.82 (d, J=8.0 Hz, 2H), 7.91 (d, J=8.0 Hz, 2H), 8.51-8.54 (dd, J=1.6 and 7.6 Hz, 1H), 8.89-8.90 (dd, J=1.6 and 4.8 Hz, 1H), 10.21 (t, J=5.6 Hz, 1H).

Step 7: Preparation of 2-(4-hydroxy-2-oxo-1-((4-(trifluoromethyl)benzyl)oxy)-1,2-dihydro-1,8-naphthyridine-3-carboxamido)acetic acid The titled compound was prepared using similar procedure as that of Example-1 (step-6) using product of step 6 described above in 67% yield.

$^1$H NMR (DMSO-$d_6$): 4.15 (d, J=5.6 Hz, 2H), 5.33 (s, 2H), 7.49-7.52 (dd, J=4.4 and 7.6 Hz, 1H), 7.82 (d, J=8.4 Hz, 2H), 7.91 (d, J=8.4 Hz, 2H), 8.51-8.54 (dd, J=2.0 and 8.0 Hz, 1H), 8.89 (d, J=4.4 Hz, 1H), 10.19 (bs, 1H).

Example 5

Preparation of 2-(1,4-dihydroxy-2-oxo-1,2-dihydroquinoline-3-carboxamido) acetic acid

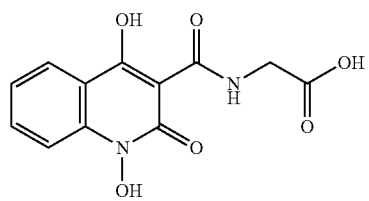 [SMILES: O=C(O)CNC(=O)c1c(O)c2ccccc2n(O)c1=O]

To a stirring solution of product of Example-1 (383 mg, 1.261 mmol) in solvent MeOH (2 mL) was added 10% Pd/C (10 mg). Reaction mixture was stirred at RT for 2 h under $H_2$ atm. Reaction mixture was filtered through Hyflow bed. The organic layer was distilled out to get titled compound as solid in 57% yield.

$^1$H NMR (DMSO-$d_6$): 4.00 (d, J=5.2 Hz, 2H), 7.35 (t, J=7.6 Hz, 1H), 7.71 (d, J=8.4 Hz, 1H), 7.80 (t, J=7.4 Hz, 1H), 8.06 (d, J=7.6 Hz, 1H), 10.44 (bs, 1H).

Example 6

Preparation of 2-(1-(benzo[d]thiazol-2-ylmethoxy)-4-hydroxy-2-oxo-1,2-dihydroquinoline-3-carboxamido)acetic acid

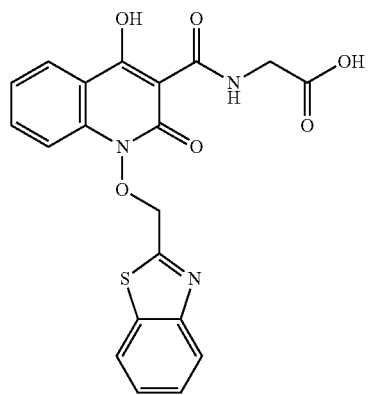 [SMILES: O=C(O)CNC(=O)c1c(O)c2ccccc2n(OCc2nc3ccccc3s2)c1=O]

Step 1: Preparation of ethyl 2-((benzo[d]thiazol-2-ylmethoxy)amino)benzoate

The titled compound was prepared using similar procedure as that of Example-1 (step-2) using ethyl 2-(hydroxyamino)benzoate and 2-(chloromethyl)benzo[d]thiazole in 52% yield.

$^1$HNMR (DMSO-$d_6$): 1.27 (t, J=7.2 Hz, 3H), 4.22-4.28 (q, J=7.0 Hz, 2H), 5.37 (s, 2H), 6.95 (t, J=7.6 Hz, 1H), 7.36 (d, J=8.4 Hz, 1H), 7.45-7.49 (m, 1H), 7.52-7.58 (m, 2H), 7.83-

7.86 (dd, J=1.6 and 8.0 Hz, 1H), 8.02 (d, J=8.0 Hz, 1H), 8.14 (d, J=7.6 Hz, 1H), 10.26 (s, 1H).

Step 2: Preparation of ethyl 2-(N-(benzo[d]thiazol-2-ylmethoxy)-3-ethoxy-3-oxopropanamido)benzoate The titled compound was prepared using similar procedure as that of Example-1 (step-3) using product of step 1 described above in 77% yield.

$^1$HNMR (DMSO-$d_6$): 1.14 (t, J=7.2 Hz, 3H), 1.25 (t, J=7.2 Hz, 3H), 3.84 (s, 2H), 4.02-4.07 (q, J=6.6 Hz, 2H), 4.21-4.26 (q, J=7.0 Hz, 2H), 5.39 (s, 2H), 7.45-7.56 (m, 4H), 7.66 (d, J=7.2 Hz, 1H), 7.83 (d, J=7.6 Hz, 1H), 8.00 (d, J=8.0 Hz, 1H), 8.12 (d, J=7.6 Hz, 1H).

Step 3: Preparation of ethyl 1-(benzo[d]thiazol-2-ylmethoxy)-4-hydroxy-2-oxo-1,2-dihydroquinoline-3-carboxylate The titled compound was prepared using similar procedure as that of Example-1 (step-4) using product of step 2 described above in 63% yield. ESI/MS m/z 397 (M+H)$^+$.

Step 4: Preparation of tert-butyl 2-(1-(benzo[d]thiazol-2-ylmethoxy)-4-hydroxy-2-oxo-1,2-dihydroquinoline-3-carboxamido)acetate To a stirring suspension of ethyl 1-(benzo[d]thiazol-2-ylmethoxy)-4-hydroxy-2-oxo-1,2-dihydroquinoline-3-carboxylate (930 mg, 2.346 mmol), tert-butyl 2-aminoacetate (369 mg, 2.82 mmol) in dioxane (5 mL) was added DIPEA (410 μl, 2.346 mmol). Reaction mixture was heated at 100° C. for 12 h. Solvent from reaction mixture was distilled out to get crude product which was then column purified using 15% EtOAC in hexane to get titled product in 43% yield.

$^1$HNMR (DMSO-$d_6$): 1.44 (s, 9H), 4.13 (d, J=5.6 Hz, 2H), 5.72 (s, 2H), 7.39-7.43 (m, 1H), 7.51-7.54 (m, 1H), 7.55-7.59 (m, 1H), 7.68 (d, J=8.4 Hz, 1H), 7.81-7.83 (m, 1H), 8.06-8.08 (m, 1H), 8.11-8.13 (dd, J=1.2 and 8.0 Hz, 1H), 8.18-8.21 (m, 1H), 10.19 (t, 1H).

Step 5: Preparation of 2-(1-(benzo[d]thiazol-2-ylmethoxy)-4-hydroxy-2-oxo-1,2-dihydroquinoline-3-carboxamido)acetic acid To a stirring solution of tert-butyl 2-(1-(benzo[d]thiazol-2-ylmethoxy)-4-hydroxy-2-oxo-1,2-dihydroquinoline-3-carboxamido)acetate (0.3 g, 0.623 mmol) in DCM (2 ml) was added TFA (3.36 ml, 43.6 mmol) slowly at 20-25° C. Reaction mixture was stirred for 3 h. Excess solvent was distilled out and then diluted with water. Precipitated product was filtered to get crude product which was then recrystallized in EtOH:EtOAC to get titled product in 87% yield.

$^1$H NMR (DMSO-$d_6$): 4.16 (d, J=5.6 Hz, 2H), 5.72 (s, 2H), 7.38-7.42 (m, 1H), 7.50-7.59 (m, 2H), 7.68 (d, J=8.4 Hz, 1H), 7.81-7.85 (m, 1H), 8.08-8.11 (dd, J=1.2 and 10.0 Hz, 1H), 8.13 (d, J=1.2 Hz, 1H), 8.18-8.21 (m, 1H), 10.20 (t, 1H), 12.96 (bs, 1H).

Example 7

Preparation of 2-(4-hydroxy-2-oxo-1-((2-(trifluoromethyl)thiazol-4-yl)methoxy)-1,2-dihydroquinoline-3-carboxamido)acetic acid

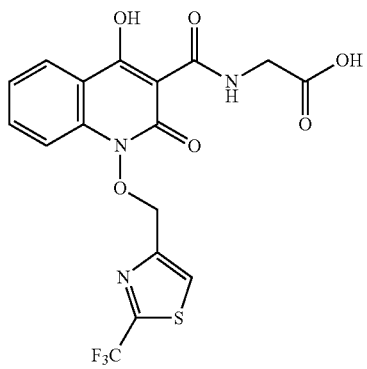 [SMILES: O=C(O)CNC(=O)c1c(O)c2ccccc2n(OCc2csc(C(F)(F)F)n2)c1=O]

Step 1: Preparation of ethyl 2-(trifluoromethyl)thiazole-4-carboxylate

To a stirring solution of ethyl 2,2,2-trifluoroethanethioamide (0.35 g, 2.71 mmol) in THF (12 ml) was added ethyl bromo pyruvate (0.375 ml, 2.98 mmol) at RT. Reaction mixture was heated at 90-100° C. for 16 h. Reaction mixture was diluted with water and DCM. The organic layer was separated and distilled out to get crude product which was column purified using 0-2% EtOAC in hexane to get titled compound in 42% yield.

$^1$HNMR (CDCl$_3$): 1.42 (t, J=7.0 Hz, 3H), 4.44-4.49 (q, J=7.0 Hz, 2H), 8.38 (s, 1H).

Step 2: Preparation of (2-(trifluoromethyl)thiazol-4-yl)methanol

To a stirring solution of ethyl 2-(trifluoromethyl)thiazole-4-carboxylate (1.0 g, 4.44 mmol) in THF (10 ml) was added LiAlH$_4$ (0.169 g, 4.44 mmol) at 0-10° C. and stirred for 1 h at RT. Reaction mixture was cooled and quenched with saturated sodium sulfate solution till precipitates observed. Precipitates obtained were filtered and filtrate was evaporated to get desired product in 56% yield.

$^1$HNMR (CDCl$_3$): 2.21 (t, J=6.0 Hz, 1H), 4.86 (d, J=5.2 Hz, 2H), 7.49 (s, 1H).

Step 3: Preparation of 4-(bromomethyl)-2-(trifluoromethyl)thiazole

To a stirring solution of (2-(trifluoromethyl)thiazol-4-yl)methanol (550 mg, 3.00 mmol) in DCM (5 ml) was added PBr$_3$ (0.283 ml, 3.00 mmol) at 0-5° C. in 5-10 min. and stirring continued for 1 h. Reaction mixture was diluted with DCM and washed with water. Organic layer was separated and distilled out to get crude product which was column purified using 0-2% EtOAC in hexane to get title compound in 36% yield.

$^1$HNMR (CDCl$_3$): 4.61 (s, 2H), 7.57 (s, 1H).

Step 4: Preparation of ethyl 2-(((2-(trifluoromethyl)thiazol-4-yl)methoxy)amino)benzoate The titled compound was prepared using similar procedure as that of Example-1 (step-2) using ethyl 2-(hydroxyamino)benzoate and product of step 3 described above in 52% yield.

$^1$HNMR (DMSO-d$_6$): 1.29 (t, J=7.0 Hz, 3H), 4.23-4.28 (q, J=7.0 Hz, 2H), 5.07 (s, 2H), 6.89 (m, 1H), 7.25 (d, J=8.0 Hz, 1H), 7.49 (s, 1H), 7.81 (d, J=6.8 Hz, 1H), 8.25 (s, 1H), 9.89 (s, 1H).

Step 5: Preparation of ethyl ethyl 2-(3-ethoxy-3-oxo-N-((2-(trifluoromethyl) thiazol-4-yl)methoxy)propanamido)benzoate The titled compound was prepared using similar procedure as that of Example-1 (step-3) using product of step 4 described above in 78% yield.

$^1$HNMR (DMSO-d$_6$): 1.16 (t, J=7.2 Hz, 3H), 1.25 (t, J=7.0 Hz, 3H), 3.72 (s, 2H), 4.06-4.11 (q, J=6.8 Hz, 2H), 4.20-4.25 (q, J=7.0 Hz, 2H), 5.09 (s, 2H), 7.42-7.48 (m, 2H), 7.62-7.66 (m, 1H), 7.76 (d, J=7.6 Hz, 1H), 8.22 (s, 1H).

Step 6: Preparation of ethyl 4-hydroxy-2-oxo-1-((2-(trifluoromethyl)thiazol-4-yl)methoxy)-1,2-dihydroquinoline-3-carboxylate The titled compound was prepared using similar procedure as that of Example-1 (step-4) using product of step 5 described above in 62% yield.

$^1$HNMR (DMSO-d$_6$): 1.21 (t, J=7.0 Hz, 3H), 4.03-4.08 (q, J=7.0 Hz, 2H), 5.25 (s, 2H), 6.94-6.98 (m, 1H), 7.21 (d, J=8.0 Hz, 1H), 7.30-7.34 (m, 1H), 7.86-7.89 (dd, J=1.2 and 8.0 Hz, 1H), 8.31 (s, 1H).

Step 7: Preparation ethyl 2-(4-hydroxy-2-oxo-1-((2-(trifluoromethyl)thiazol-4-yl)methoxy)-1,2-dihydroquinoline-3-carboxamido)acetate The titled compound was prepared using similar procedure as that of Example-1 (step-5) using product of step 6 described above in 79% yield.

$^1$HNMR (DMSO-d$_6$): 1.23 (t, J=7.0 Hz, 3H), 4.15-4.20 (q, J=7.0 Hz, 2H), 4.23 (d, J=5.6 Hz, 2H), 5.45 (s, 2H), 7.35-7.39 (m, 1H), 7.51 (d, J=8.0 Hz, 1H), 7.72-7.77 (m, 1H), 8.06-8.09 (dd, J=1.2 and 8.0 Hz, 1H), 8.42 (s, 1H), 10.27 (t, 1H).

Step 8: Preparation of 2-(4-hydroxy-2-oxo-1-((2-(trifluoromethyl)thiazol-4-yl)methoxy)-1,2-dihydroquinoline-3-carboxamido)acetic acid The titled compound was prepared using similar procedure as that of Example-1 (step-6) using product of step 7 described above in 86% yield.

$^1$H NMR (DMSO-d$_6$): 4.14 (d, J=5.6 Hz, 2H), 5.45 (s, 2H), 7.36 (t, 1H), 7.51 (d, J=8.4 Hz, 1H), 7.72-7.76 (m, 1H), 8.06-8.09 (dd, J=1.2 and 8.0 Hz, 1H), 8.42 (s, 1H), 10.23 (t, 1H).

Example 8

Preparation of 2-(1-(allyloxy)-4-hydroxy-2-oxo-6-phenoxy-1,2-dihydroquinoline-3-carboxamido)acetic acid

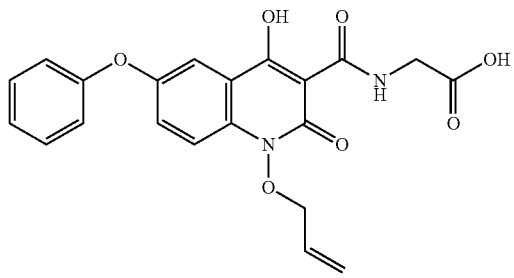 [SMILES: C=CCOn1c(=O)c(C(=O)NCC(=O)O)c(O)c2cc(Oc3ccccc3)ccc21]

Step 1: Preparation of ethyl 2-nitro-5-phenoxybenzoate

To a stirring suspension of ethyl 5-chloro-2-nitrobenzoate (15 g, 65.3 mmol) and K$_2$CO$_3$ (13.54 g, 98 mmol) in DMF (5 ml) was added phenol (6.76 g, 71.9 mmol). Reaction mixture was heated at 130° C. for 16 h. Reaction mixture was diluted with water and extracted with EtOAc. The organic layer was separated and distilled out to get crude product which was column purified using 10% EtOAC in hexane to get the titled compound in 36% yield.

$^1$HNMR (DMSO-d$_6$): 1.25 (t, J=7.0 Hz, 3H), 4.27-4.32 (q, J=7.2 Hz, 2H), 7.20-7.23 (m, 3H), 7.27 (d, J=2.8 Hz, 1H), 7.30-7.34 (m, 1H), 7.49-7.53 (m, 2H), 8.13 (d, J=9.2 Hz, 1H).

Step 2: Preparation of ethyl 2-(hydroxyamino)-5-phenoxybenzoate

The titled compound was prepared using similar procedure as that of Example-1 (step-1) using product of step 1 described above. The crude product was directly used in next step.

Step 3: Preparation of ethyl 2-((allyloxy)amino)-5-phenoxybenzoate

The titled compound was prepared using similar procedure as that of Example-1 (step-2) using product of step 2 described above.

$^1$HNMR (DMSO-d$_6$): 1.26 (t, J=7.2 Hz, 3H), 4.22-4.27 (q, J=7.0 Hz, 2H), 4.37-4.4 (m, 2H), 5.27-5.30 (m, 1H), 5.35-5.40 (m, 1H), 6.00-6.07 (m, 1H), 6.92-7.07 (m, 2H), 7.07-7.11 (m, 1H), 7.28-7.30 (m, 2H), 7.34-7.38 (m, 2H), 7.44-7.45 (m, 1H), 9.65 (s, 1H).

Step 4: Preparation of ethyl 2-(N-(allyloxy)-3-ethoxy-3-oxopropanamido)-5-phenoxybenzoate The titled compound was prepared using similar procedure as that of Example-1 (step-3) using product of step 3 described above. The crude product was directly used in next step.

Step 5: Preparation of ethyl 1-(allyloxy)-4-hydroxy-2-oxo-6-phenoxy-1,2-dihydroquinoline-3-carboxylate The titled compound was prepared using similar procedure as that of Example-1 (step-4) using product of step 4 described above. ESI/MS m/z 382 (M+H)⁺.

Step 6: Preparation of ethyl 2-(1-(allyloxy)-4-hydroxy-2-oxo-6-phenoxy-1,2-dihydroquinoline-3-carboxamido)acetate The titled compound was prepared using similar procedure as that of Example-1 (step-5) using product of step 5 described above. ESI/MS m/z 439.1 (M+H)⁺.

Step 7: Preparation of 2-(1-(allyloxy)-4-hydroxy-2-oxo-6-phenoxy-1,2-dihydroquinoline-3-carboxamido)acetic acid The titled compound was prepared using similar procedure as that of Example-1 (step-6) using product of step 6 described above in 78% yield.
¹H NMR (DMSO-d₆): 4.12 (d, J=5.6 Hz, 2H), 4.74 (d, J=6.4 Hz, 2H), 5.37 (d, J=10.4 Hz, 1H), 5.48-5.52 (dd, J=1.2 and 17.2 Hz, 1H), 6.12-6.22 (m, 1H), 7.09 (d, J=7.6 Hz, 2H), 7.21 (t, J=7.4 Hz, 1H), 7.36-7.46 (m, 2H), 7.49 (d, J=2.8 Hz, 1H), 7.60-7.63 (dd, J=2.4 and 9.2 Hz, 1H), 7.69 (d, J=8.8 Hz, 1H), 10.27 (bs, 1H).

Example 9

Preparation of 2-(1-(allyloxy)-4-hydroxy-2-oxo-6-phenyl-1,2-dihydroquinoline-3-carboxamido)acetic acid

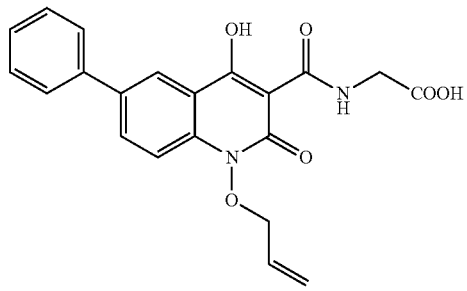 [SMILES: C=CCOn1c(=O)c(C(=O)NCC(=O)O)c(O)c2cc(-c3ccccc3)ccc21]

Step 1: Preparation of ethyl 4-nitro-[1,1'-biphenyl]-3-carboxylate

To a stirring solution of ethyl 5-chloro-2-nitrobenzoate (2 g, 8.71 mmol) and phenylboronic acid (2.124 g, 17.42 mmol) in DMF (20 ml) was added K₃PO₄ (2.77 g, 13.07 mmol), palladium acetate (0.098 g, 0.436 mmol) and tetrabutylammonium bromide (4.21 g, 13.07 mmol). Reaction mixture was heated at 95° C. for 16 h. Reaction mixture was diluted with water and extracted with EtOAc. The organic layer was separated and distilled out to get crude product which was column purified using 10% EtOAC in hexane to get the titled compound in 89% yield.
¹HNMR (DMSO-d₆): 1.30 (t, J=7.0 Hz, 3H), 4.32-4.38 (q, J=7.2 Hz, 2H), 7.48-7.57 (m, 3H), 7.80-7.83 (m, 2H), 8.08-8.10 (m, 2H), 8.16-8.19 (m, 1H).

Step 2: Preparation of ethyl 4-(hydroxyamino)-[1,1'-biphenyl]-3-carboxylate

The titled compound was prepared using similar procedure as that of Example-1 (step-1) using product of step 1 described above. The crude product was directly used in next step.

Step 3: Preparation of ethyl 4-((allyloxy)amino)-[1,1'-biphenyl]-3-carboxylate The titled compound was prepared using similar procedure as that of Example-1 (step-2) using product of step 2 described above. ESI/MS m/z 297.9 (M+H)⁺.

Step 4: Preparation of ethyl 4-(N-(allyloxy)-3-ethoxy-3-oxopropanamido)-[1,1-biphenyl]-3-carboxylate The titled compound was prepared using similar procedure as that of Example-1 (step-3) using product of step 3 described above. ESI/MS m/z 412.0 (M+H)⁺.

Step 5: Preparation of ethyl 1-(allyloxy)-4-hydroxy-2-oxo-6-phenyl-1,2-dihydroquinoline-3-carboxylate The titled compound was prepared using similar procedure as that of Example-1 (step-4) using product of step 4 described above. ESI/MS m/z 366.0 (M+H)⁺.

Step 6: Preparation of ethyl 2-(1-(allyloxy)-4-hydroxy-2-oxo-6-phenyl-1,2-dihydroquinoline-3-carboxamido)acetate The titled compound was prepared using similar procedure as that of Example-1 (step-5) using product of step 5 described above.
¹H NMR (DMSO-d₆): 1.23 (t, J=7.2 Hz, 3H), 4.14-4.19 (q, J=7.2 Hz, 2H), 4.22 (d, J=5.6 Hz, 2H), 4.78 (d, J=6.4 Hz, 2H), 5.38-5.41 (dd, J=0.8 and 10.0 Hz, 1H), 5.49-5.53 (dd, J=1.2 and 17.2 Hz, 1H), 6.16-6.23 (m, 1H), 7.40-7.44 (m, 1H), 7.49-7.53 (m, 2H), 7.74-7.76 (dd, J=1.6 and 8.8 Hz, 3H), 8.17-8.20 (dd, J=2.0 and 8.8 Hz, 1H), 8.28 (d, J=2.4 Hz, 1H), 10.28 (t, 1H).

Step 7: Preparation of 2-(1-(allyloxy)-4-hydroxy-2-oxo-6-phenyl-1,2-dihydroquinoline-3-carboxamido) acetic acid The titled compound was prepared using similar procedure as that of Example-1 (step-6) using product of step 6 described above in 79% yield.
¹H NMR (DMSO-d₆): 4.04 (d, J=6.4 Hz, 2H), 4.77 (d, J=6.4 Hz, 2H), 5.38-5.40 (m, 1H), 5.33-5.49 (dd, J=1.6 and 17.2 Hz, 1H), 6.14-6.24 (m, 1H), 7.41 (t, J=7.2 Hz, 1H), 7.49-7.52 (m, 2H), 7.27-7.75 (m, 3H), 8.16-8.19 (dd, J=2.0 and 8.4 Hz, 1H), 8.28 (d, J=2.0 Hz, 1H), 10.25 (t, J=4.8 Hz, 1H), 12.98 (bs, 1H).

Example 10

Preparation of 2-(4-(allyloxy)-7-hydroxy-5-oxo-4,5-dihydrothieno[3,2-b]pyridine-6-carboxamido)acetic acid

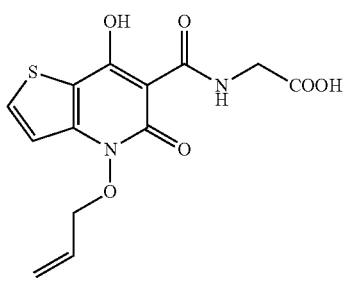 [SMILES: C=CCOn1c(=O)c(C(=O)NCC(=O)O)c(O)c2sccc21]

Step 1: Preparation of methyl 3-nitrothiophene-2-carboxylate

To a stirring solution of methyl 3-aminothiophene-2-carboxylate (5 g, 31.8 mmol) in Conc. HCl (4.77 ml) was added aq. solution of sodium nitrite (2.195 g, 31.8 mmol) slowly at 0-5° C. Reaction mixture was stirred at 0-5° C. for 1 h. To this was added aq. solution of sodium tetrafluoroborate (5.24 g, 47.7 mmol) in one lot. After 30 min. precipitated product was filtered. The product was added to the stirring suspension of copper bronze (6.06 g, 95 mmol) and sodium nitrite (26.3 g, 382 mmol) in water (100 ml). Reaction mixture was stirred at 25° C. for 1 h. Reaction mixture was diluted with water and EtOAc and filtered through Hyflow bed. The organic layer was separated and distilled out to get crude product which was column purified using 0-5% EtOAC in hexane to get titled compound as light yellow solid in 63% yield.

$^1$HNMR (DMSO-$d_6$): 3.86 (s, 3H), 7.67 (d, J=5.2 Hz, 1H), 8.04 (d, J=5.6 Hz, 1H).

Step 2: Preparation of methyl 3-(hydroxyamino)thiophene-2-carboxylate

The titled compound was prepared using similar procedure as that of Example-1 (step-1) using product of step 1 described above. The crude product was directly used in next step.

Step 3: Preparation of methyl 3-((allyloxy)amino)thiophene-2-carboxylate

The titled compound was prepared using similar procedure as that of Example-1 (step-2) using product of step 2 described above in 49% yield.

$^1$H NMR (DMSO-$d_6$): 3.86 (s, 3H), 4.36-4.38 (m, 2H), 5.25-5.28 (m, 1H), 5.32-5.38 (m, 1H), 5.96-6.06 (m, 1H), 6.95 (d, J=5.2 Hz, 1H), 7.76 (d, J=4.8 Hz, 1H), 9.33 (s, 1H).

Step 4: Preparation of methyl 3-(N-(allyloxy)-3-ethoxy-3-oxopropanamido)thiophene-2-carboxylate The titled compound was prepared using similar procedure as that of Example-1 (step-3) using product of step 3 described above. ESI/MS m/z 328.0 (M+H)$^+$.

Step 5: Preparation of ethyl 4-(allyloxy)-7-hydroxy-5-oxo-4,5-dihydrothieno[3,2-b]pyridine-6-carboxylate The titled compound was prepared using similar procedure as that of Example-1 (step-4) using product of step 4 described above in 68% yield.

$^1$H NMR (DMSO-$d_6$): 1.31 (t, J=7.2 Hz, 3H), 4.31-4.36 (q, J=7.0 Hz, 2H), 4.70 (d, J=6.4 Hz, 2H), 5.32-5.34 (dd, J=0.8 and 10.0 Hz, 1H), 5.40-5.45 (dd, J=1.2 and 18.4 Hz, 1H), 6.07-6.14 (m, 1H), 7.27 (d, J=5.6 Hz, 1H), 8.23 (d, J=5.2 Hz, 1H), 13.36 (bs, 1H).

Step 6: Preparation of ethyl 2-(4-(allyloxy)-7-hydroxy-5-oxo-4,5-dihydrothieno[3,2-b]pyridine-6-carboxamido)acetate The titled compound was prepared using similar procedure as that of Example-1 (step-5) using product of step 5 described above in 62% yield.

$^1$H NMR (DMSO-$d_6$): 1.22 (t, J=7.0 Hz, 3H), 4.13-4.18 (q, J=7.2 Hz, 2H), 4.19 (d, J=5.6 Hz, 2H), 4.78 (d, J=6.4 Hz, 2H), 5.34 (d, J=10.4 Hz, 1H), 5.42-5.46 (dd, J=1.6 and 17.2 Hz, 1H), 6.09-6.19 (m, 1H), 7.36 (d, J=5.2 Hz, 1H), 8.29 (d, J=5.6 Hz, 1H), 10.24 (t, J=5.6 Hz, 1H).

Step 7: Preparation of 2-(4-(allyloxy)-7-hydroxy-5-oxo-4,5-dihydrothieno[3,2-b]pyridine-6-carboxamido)acetic acid The titled compound was prepared using similar procedure as that of Example-1 (step-6) using product of step 6 described above in 75% yield.

$^1$H NMR (DMSO-$d_6$): 4.11 (d, J=5.6 Hz, 2H), 4.77 (d, J=6.8 Hz, 2H), 5.34 (d, J=10.4 Hz, 1H), 5.42-5.47 (dd, J=0.8 and 16.8 Hz, 1H), 6.11-6.17 (m, 1H), 7.36 (d, J=5.2 Hz, 1H), 8.28 (d, J=5.2 Hz, 1H), 10.22 (t, J=5.4 Hz, 1H), 12.94 (bs, 1H).

Using appropriate starting materials and suitable modifications of the process described in above examples, including suitable addition and/or deletion of steps as may be necessary, well within the scope of a person skilled in the art, the following compounds were prepared in an analogous manner.

Example 11

Preparation of 2-(4-hydroxy-1-methoxy-2-oxo-1,2-dihydroquinoline-3-carboxamido)acetic acid

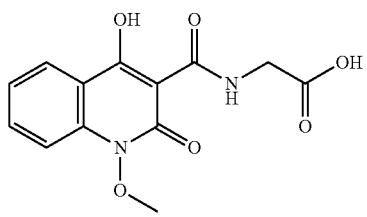 [SMILES: COn1c(=O)c(C(=O)NCC(=O)O)c(O)c2ccccc21]

$^1$HNMR (DMSO-$d_6$): 4.01 (s, 3H), 4.15 (d, J=5.6 Hz, 2H), 7.43 (t, 1H), 7.67 (d, J=8.4 Hz, 1H), 7.88 (t, 1H), 8.13 (d, J=8 Hz, 1H), 10.25 (t, 1H).

Example 12

Preparation of 2-(4-hydroxy-2-oxo-1-((4-(trifluoromethyl)benzyl)oxy)-1,2-dihydroquinoline-3-carboxamido)acetic acid

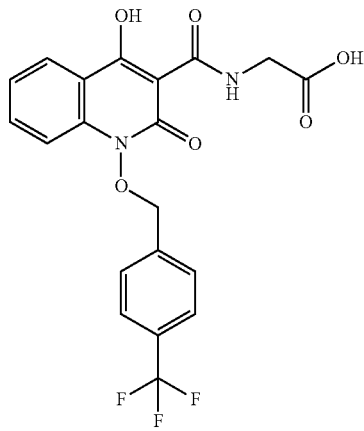 [SMILES: O=C(O)CNC(=O)c1c(O)c2ccccc2n(OCc2ccc(C(F)(F)F)cc2)c1=O]

$^1$H NMR (DMSO-d$_6$): 4.16 (d, J=5.6 Hz, 2H), 5.32 (s, 2H), 7.42 (t, 1H), 7.67 (d, J=8.4 Hz, 1H), 7.82-7.90 (m, 5H), 8.11-8.13 (dd, J=1.2 and 8 Hz, 1H), 10.27 (t, 1H).

Example 13

Preparation of 2-(4-hydroxy-2-oxo-1-((2-(trifluoromethyl)benzyl)oxy)-1,2-dihydroquinoline-3-carboxamido)acetic acid

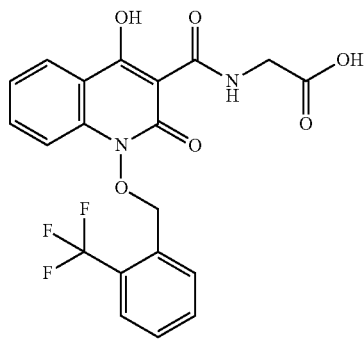 [SMILES: O=C(O)CNC(=O)c1c(O)c2ccccc2n(OCc2ccccc2C(F)(F)F)c1=O]

$^1$H NMR (DMSO-d$_6$): 4.17 (d, J=5.6 Hz, 2H), 5.41 (s, 2H), 7.40 (t, 1H), 7.51 (d, J=8.4 Hz, 1H), 7.67 (t, 1H), 7.79-7.85 (m, 3H), 8.02 (d, J=7.6 Hz, 1H), 8.12 (d, J=7.6 Hz, 1H), 10.22 (t, 1H).

Example 14

Preparation of 2-(4-hydroxy-2-oxo-1-(pyridin-2-ylmethoxy)-1,2-dihydroquinoline-3-carboxamido)acetic acid

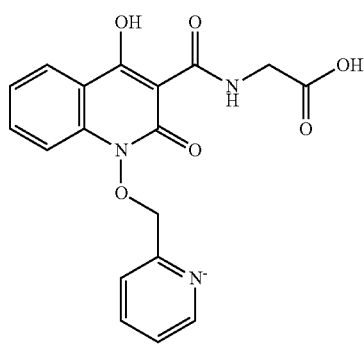

$^1$H NMR (DMSO-d$_6$): 4.17 (d, J=5.6 Hz, 2H), 5.31 (s, 2H), 7.38-7.45 (m, 2H), 7.71-7.74 (m, 2H), 7.81-7.85 (m, 1H), 7.87-7.91 (m, 1H), 8.11 (d, J=6.8 Hz, 1H), 8.64 (d, J=4 Hz, 1H), 10.27 (t, 1H).

Example 15

Preparation of 2-(1-(allyloxy)-4-hydroxy-2-oxo-1,2-dihydroquinoline-3-carboxamido)acetic acid

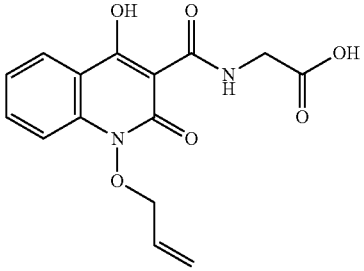 [SMILES: C=CCOn1c(=O)c(C(=O)NCC(=O)O)c(O)c2ccccc21]

$^1$H NMR (DMSO-d$_6$): 4.14 (d, J=6 Hz, 2H), 4.75 (d, J=6.8 Hz, 2H), 5.39 (d, J=10.4 Hz, 1H), 5.52 (d, J=17.2 Hz, 1H), 6.12-6.22 (m, 1H), 7.42 (t, 1H), 7.64 (t, 1H), 7.87 (t, 1H), 8.12 (d, 1H), 10.25 (t, 1H).

Example 16

Preparation of 2-(1-((2,6-difluorobenzyl)oxy)-4-hydroxy-2-oxo-1,2-dihydroquinoline-3-carboxamido)acetic acid

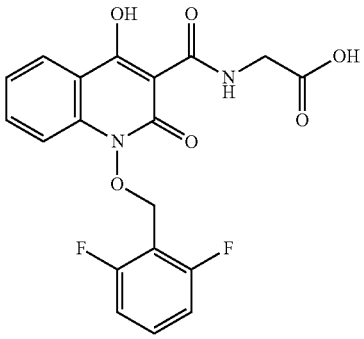 [SMILES: O=C(O)CNC(=O)c1c(O)c2ccccc2n(OCc2c(F)cccc2F)c1=O]

$^1$H NMR (DMSO-d$_6$): 4.17 (d, J=6 Hz, 2H), 5.4 (s, 2H), 7.18 (t, 2H), 7.37 (t, 1H), 7.50-7.56 (m, 2H), 7.78-7.82 (m, 1H), 8.07-8.10 (dd, J=1.2 and 8 Hz, 1H), 10.22 (t, 1H).

Example 17

Preparation of 2-(1-(benzyloxy)-7-chloro-4-hydroxy-2-oxo-1,2-dihydroquinoline-3-carboxamido)acetic acid

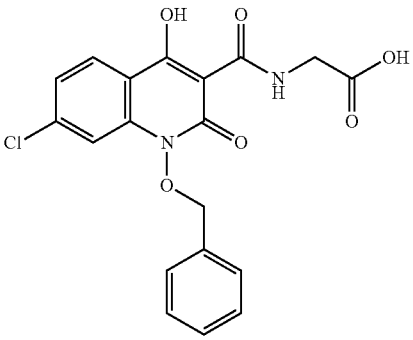 [SMILES: O=C(O)CNC(=O)c1c(O)c2ccc(Cl)cc2n(OCc2ccccc2)c1=O]

$^1$H NMR (DMSO-d$_6$): 4.16 (d, J=5.6 Hz, 2H), 5.26 (s, 2H), 7.41-7.53 (m, 5H), 7.62 (t, 2H), 8.09 (d, J=8.4 Hz, 1H), 10.21 (t, 1H).

Example 18

Preparation of 2-(7-chloro-4-hydroxy-2-oxo-1-((4-(trifluoromethyl)benzyl)oxy)-1,2-dihydroquinoline-3-carboxamido)acetic acid

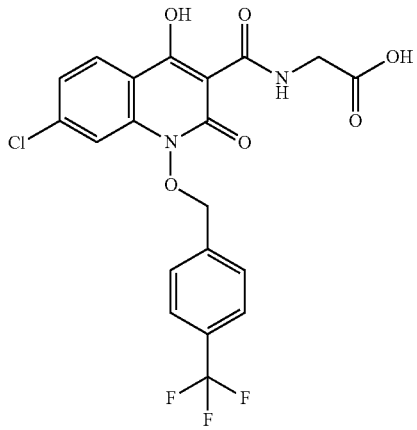 [SMILES: O=C(O)CNC(=O)c1c(O)c2ccc(Cl)cc2n(OCc2ccc(C(F)(F)F)cc2)c1=O]

$^1$H NMR (DMSO-d$_6$): 4.13 (d, J=5.2 Hz, 2H), 5.35 (s, 2H), 7.43 (d, J=7.6 Hz, 1H), 7.56 (s, 1H), 7.83 (d, J=8.4 Hz, 2H), 7.89 (d, J=8 Hz, 2H), 8.10 (d, J=8.4 Hz, 1H), 10.18 (t, 1H).

Example 19

Preparation of 2-(1-(allyloxy)-7-chloro-4-hydroxy-2-oxo-1,2-dihydroquinoline-3-carboxamido)acetic acid

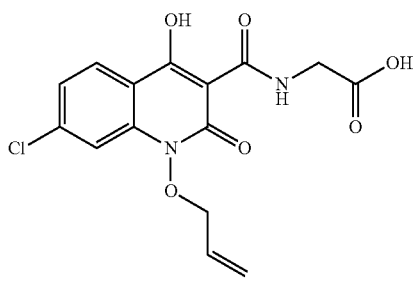 [SMILES: C=CCOn1c(=O)c(C(=O)NCC(=O)O)c(O)c2ccc(Cl)cc21]

$^1$H NMR (DMSO-d$_6$): 4.07 (d, J=5.2 Hz, 2H), 4.74 (d, J=6.4 Hz, 2H), 5.36 (d, 1H), 5.51 (d, 1H), 6.14-6.20 (m, 1H), 7.42 (d, J=8.0 Hz, 1H), 7.63 (s, 1H), 8.08 (d, J=8.4 Hz, 1H), 10.29 (t, 1H).

Example 20

Preparation of 2-(7-chloro-1-((2,6-difluorobenzyl)oxy)-4-hydroxy-2-oxo-1,2-dihydroquinoline-3-carboxamido)acetic acid

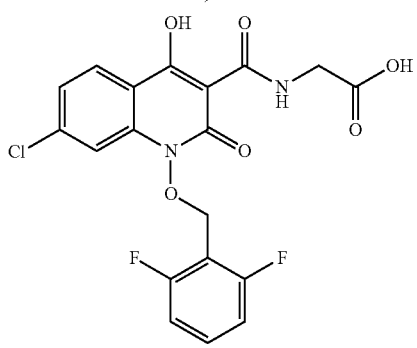

$^1$H NMR (DMSO-d$_6$): 4.15 (d, J=5.6 Hz, 2H), 5.40 (s, 2H), 7.21 (t, 2H), 7.40-7.43 (dd, J=2.0 and J=8.4 Hz, 1H), 7.50 (d, J=2.0 Hz, 1H), 7.53-7.59 (m, 1H), 8.06 (d, J=8.4 Hz, 1H), 10.13 (t, 1H), 12.95 (bs, 1H).

Example 21

Preparation of 2-(4-hydroxy-2-oxo-1-propoxy-1,2-dihydroquinoline-3-carboxamido) acetic acid

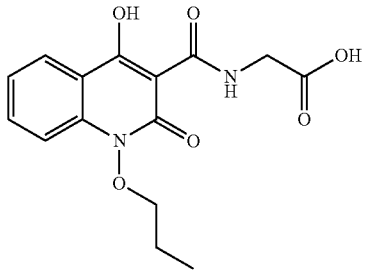 [SMILES: CCCOn1c(=O)c(C(=O)NCC(=O)O)c(O)c2ccccc21]

$^1$H NMR (DMSO-d$_6$): 1.06 (t, 3H), 1.79-1.87 (m, 2H), 4.12-4.16 (m, 4H), 7.41 (t, 1H), 7.62 (d, J=8.4 Hz, 1H), 7.85-7.89 (m, 1H), 8.09-8.11 (dd, J=0.8 and J=8.0 Hz, 1H), 10.25 (t, 1H).

Example 22

Preparation of 2-(1-((3,5-dimethylbenzyl)oxy)-4-hydroxy-2-oxo-1,2-dihydroquinoline-3-carboxamido)acetic acid

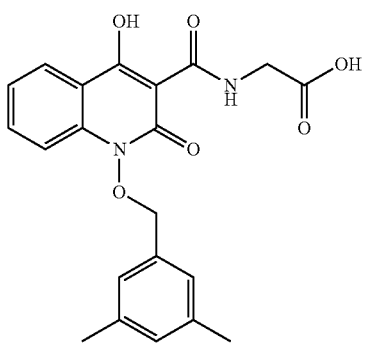 [SMILES: Cc1cc(C)cc(COn2c(=O)c(C(=O)NCC(=O)O)c(O)c3ccccc32)c1]

$^1$H NMR (DMSO-d$_6$): 2.32 (s, 6H), 4.16 (d, J=5.6 Hz, 2H), 5.11 (s, 2H), 7.24 (s, 1H), 7.42 (t, 2H), 7.65 (d, J=8.4 Hz, 1H), 7.86 (d, J=1.2 Hz, 1H), 7.90 (t, 1H), 8.13 (t, 1H), 10.29 (t, 1H), 12.95 (bs, 1H).

Example 23

Preparation of 2-(1-((4-fluorobenzyl)oxy)-4-hydroxy-2-oxo-1,2-dihydroquinoline-3-carboxamido) acetic acid

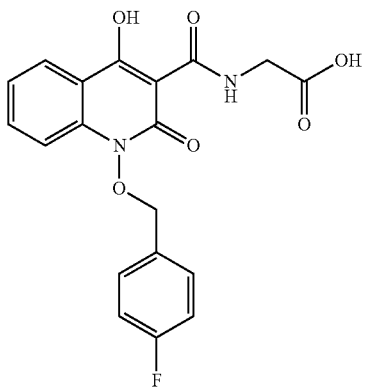 [SMILES: O=C(O)CNC(=O)c1c(O)c2ccccc2n(OCc2ccc(F)cc2)c1=O]

$^1$H NMR (DMSO-d$_6$): 4.15 (d, J=5.6 Hz, 2H), 5.21 (s, 2H), 7.28 (t, 2H), 7.41 (t, 1H), 7.63 (d, J=8.4 Hz, 1H), 7.69-7.73 (m, 2H), 7.84 (t, 1H), 8.10 (d, J=8.0 Hz, 1H), 10.28 (t, 1H),

Example 24

Preparation of 2-(1-((4-cyanobenzyl)oxy)-4-hydroxy-2-oxo-1,2-dihydroquinoline-3-carboxamido)acetic acid

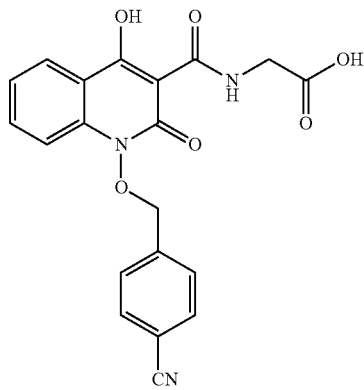 [SMILES: N#Cc1ccc(COn2c(=O)c(C(=O)NCC(=O)O)c(O)c3ccccc32)cc1]

$^1$H NMR (DMSO-d$_6$): 4.14 (d, J=5.2 Hz, 2H), 5.32 (s, 2H), 7.42 (t, 1H), 7.64 (d, J=8.4 Hz, 1H), 7.83-7.87 (m, 3H), 7.92 (d, J=8.0 Hz, 2H), 8.11 (d, J=8.0 Hz, 1H), 10.23 (t, 1H).

Example 25

Preparation of 2-(4-hydroxy-1-isopropoxy-2-oxo-1,2-dihydroquinoline-3-carboxamido)acetic acid

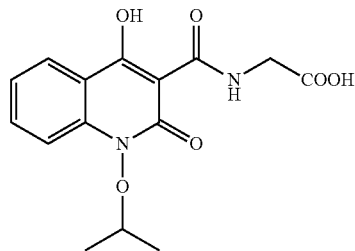 [SMILES: CC(C)On1c(=O)c(C(=O)NCC(=O)O)c(O)c2ccccc21]

$^1$H NMR (DMSO-d$_6$): 1.29 (d, J=6.0 Hz, 6H), 4.12 (d, J=5.6 Hz, 2H), 4.77-4.83 (m, 1H), 7.37-7.41 (m, 1H), 7.70 (d, J=8.4 Hz, 1H), 7.81 (m, 1H), 8.08-8.10 (dd, J=1.2 and 8.0 Hz, 1H), 10.26 (t, J=5.2 Hz, 1H), 12.91 (bs, 1H).

Example 26

Preparation of 2-(1-((2-cyanobenzyl)oxy)-4-hydroxy-2-oxo-1,2-dihydroquinoline-3-carboxamido)acetic acid

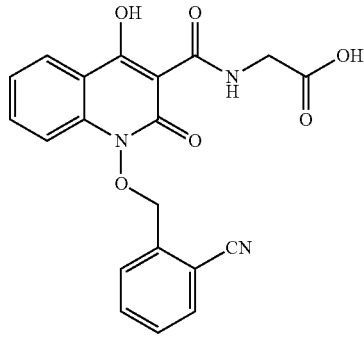 [SMILES: N#Cc1ccccc1COn1c(=O)c(C(=O)NCC(=O)O)c(O)c2ccccc21]

$^1$H NMR (DMSO-d$_6$): 4.15 (d, J=5.6 Hz, 2H), 5.43 (s, 2H), 7.37-7.41 (m, 1H), 7.58-7.66 (m, 2H), 7.76-7.83 (m, 2H), 7.92 (d, J=1.2 Hz, 1H), 7.924 (d, J=0.8 Hz, 1H), 8.10-8.12 (dd, J=1.2 and 8.0 Hz, 1H), 10.21 (t, 1H).

Example 27

Preparation of 2-(1-(allyloxy)-4-hydroxy-2-oxo-1,2-dihydro-1,8-naphthyridine-3-carboxamido)acetic acid

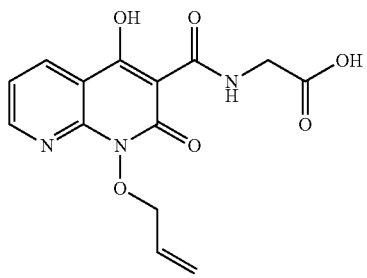 [SMILES: C=CCOn1c(=O)c(C(=O)NCC(=O)O)c(O)c2cccnc21]

$^1$H NMR (DMSO-d$_6$): 4.13 (d, J=5.6 Hz, 2H), 4.74 (d, J=6.4 Hz, 2H), 5.31 (d, 1H), 5.40-5.44 (m, 1H), 6.09-6.18 (m, 1H), 7.46-7.50 (dd, J=4.4 and 7.6 Hz, 1H), 8.48-8.50 (dd, J=1.6 and 8.0 Hz, 1H), 8.85-8.86 (dd, J=1.6 and 4.4 Hz, 1H), 10.18 (t, 1H), 12.98 (bs, 1H).

Example 28

Preparation of 2-(4-hydroxy-1-isobutoxy-2-oxo-1,2-dihydroquinoline-3-carboxamido)acetic acid

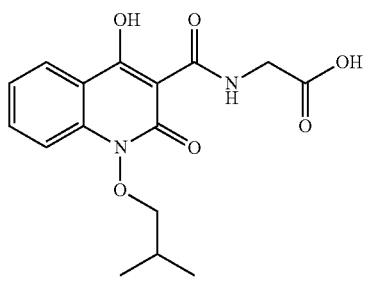 [SMILES: CC(C)COn1c(=O)c(C(=O)NCC(=O)O)c(O)c2ccccc21]

$^1$H NMR (DMSO-d$_6$): 1.07 (d, 6H), 2.13-2.21 (m, 1H), 3.96 (d, J=6.8 Hz, 2H), 4.11 (d, J=5.6 Hz, 2H), 7.41 (t, 1H), 7.60 (d, J=8.4 Hz, 1H), 7.88 (t, 1H), 8.10-8.12 (dd, J=1.2 and 8.0 Hz, 1H), 10.25 (t, 1H).

Example 29

Preparation of 2-(1-(cyclopropylmethoxy)-4-hydroxy-6-methoxy-2-oxo-1,2-dihydroquinoline-3-carboxamido)acetic acid

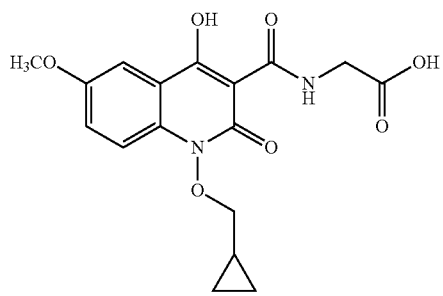 [SMILES: COc1ccc2c(c1)c(O)c(C(=O)NCC(=O)O)c(=O)n2OCC1CC1]

$^1$H NMR (DMSO-d$_6$): 0.57 (m, 2H), 0.59 (m, 2H), 1.23-1.28 (m, 1H), 3.86 (s, 3H), 4.03 (d, J=7.2 Hz, 2H), 4.12 (d, J=6.0 Hz, 2H), 7.51 (t, 2H), 7.66 (d, J=9.6 Hz, 1H), 10.33 (t, 1H), 12.95 (bs, 1H).

Example 30

Preparation of 2-(1-(allyloxy)-6-chloro-4-hydroxy-2-oxo-1,2-dihydroquinoline-3-carboxamido)acetic acid

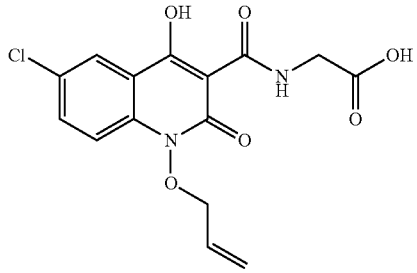 [SMILES: C=CCOn1c(=O)c(C(=O)NCC(=O)O)c(O)c2cc(Cl)ccc21]

$^1$H NMR (DMSO-$d_6$): 4.12 (d, J=5.6 Hz, 2H), 4.73 (d, J=6.4 Hz, 2H), 5.46 (d, J=1.2 Hz, 1H), 5.51 (d, J=1.2 Hz, 1H), 6.10-6.21 (m, 1H), 7.66 (d, J=8.8 Hz, 1H), 7.87 (d, J=8.8 Hz, 1H), 8.03 (d, J=2.4 Hz, 1H), 10.21 (t, 1H).

Example 31

Preparation of 2-(1-(allyloxy)-5-fluoro-4-hydroxy-2-oxo-1,2-dihydroquinoline-3-carboxamido)acetic acid

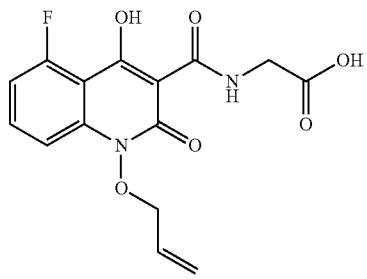 [SMILES: C=CCOn1c(=O)c(C(=O)NCC(=O)O)c(O)c2c(F)cccc21]

$^1$H NMR (DMSO-$d_6$): 4.12 (d, J=5.6 Hz, 2H), 4.71 (d, J=6.4 Hz, 2H), 5.47 (d, J 1.6 Hz, 1H), 5.52 (d, J=1.6 Hz, 1H), 6.12-6.17 (m, 1H), 7.19 (t, 1H), 7.46 (d, J=8.8 Hz, 1H), 7.83 (d, J=5.6 Hz, 1H), 10.26 (t, 1H).

Example 32

Preparation of 2-(1-(cyclopropylmethoxy)-4-hydroxy-2-oxo-1,2-dihydro-1,6-naphthyridine-3-carboxamido)acetic acid

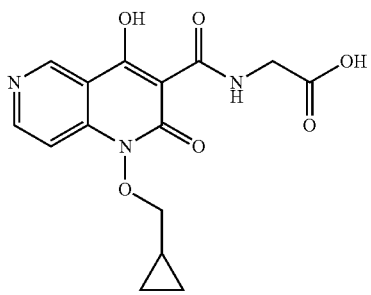 [SMILES: O=C(O)CNC(=O)c1c(O)c2cnccc2n(OCC2CC2)c1=O]

$^1$H NMR (DMSO-$d_6$): 0.35-0.39 (m, 2H), 0.56-0.61 (m, 2H), 1.23-1.30 (m, 1H), 4.05 (d, J=7.6 Hz, 2H), 4.12 (d, J=5.2 Hz, 2H), 7.61 (d, J=6.00 Hz, 1H), 8.77 (d, J=5.6 Hz, 1H), 9.18 (s, 1H), 10.06 (t, 1H).

Example 33

Preparation of 2-(1-(allyloxy)-4-hydroxy-6-methoxy-2-oxo-1,2-dihydroquinoline-3-carboxamido) acetic acid

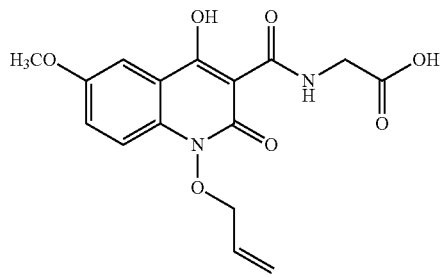 [SMILES: C=CCOn1c(=O)c(C(=O)NCC(=O)O)c(O)c2cc(OC)ccc21]

$^1$H NMR (DMSO-$d_6$): 3.85 (s, 3H), 4.13 (d, J=5.6 Hz, 2H), 4.72 (d, J=6.4 Hz, 2H), 5.35-5.38 (m, 1H), 5.45-5.50 (dd, J=1.2 and 16.8 Hz, 1H), 6.10-6.20 (m, 1H), 7.33-7.62 (m, 3H), 10.32 (t, 1H).

Example 34

Preparation of 2-(4-hydroxy-6-methoxy-2-oxo-1-(prop-2-yn-1-yloxy)-1,2-dihydroquinoline-3-carboxamido)acetic acid

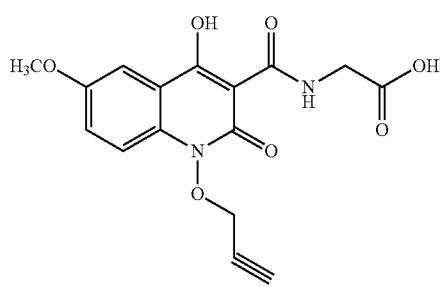 [SMILES: C#CCOn1c(=O)c(C(=O)NCC(=O)O)c(O)c2cc(OC)ccc21]

$^1$H NMR (DMSO-$d_6$): 3.66-3.71 (m, 1H), 3.86 (s, 3H), 4.12 (d, J=5.6 Hz, 2H), 5.03 (d, 2H), 7.48 (t, 2H), 7.64 (d, J=9.2 Hz, 1H), 10.24 (t, 1H).

Example 35

Preparation of 2-(5-(cyclopropylmethoxy)-8-hydroxy-6-oxo-5,6-dihydropyrido[2,3-b]pyrazine-7-carboxamido)acetic acid

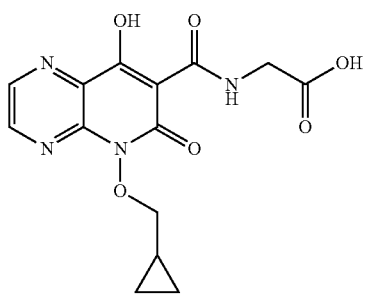 [SMILES: O=C(O)CNC(=O)c1c(O)c2nccnc2n(OCC2CC2)c1=O]

$^1$H NMR (DMSO-$d_6$): 0.36-0.37 (m, 2H), 0.55-0.59 (m, 2H), 1.23-1.29 (m, 1H), 4.03 (t, 2H), 4.14 (d, J=5.6 Hz, 2H), 8.75 (d, J=2.0 Hz, 1H), 8.89 (d, J=2.0 Hz, 1H), 10.19 (s, 1H), 12.97 (bs, 1H).

Example 36

Preparation of 2-(5-((2,6-difluorobenzyl)oxy)-8-hydroxy-6-oxo-5,6-dihydropyrido[2,3-b]pyrazine-7-carboxamido)acetic acid

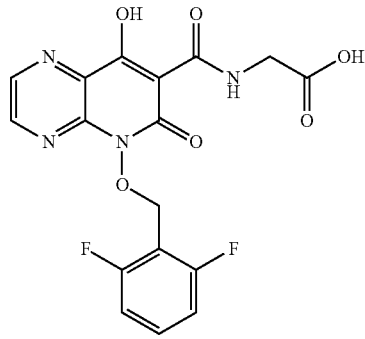 [SMILES: O=C(O)CNC(=O)c1c(O)c2nccnc2n(OCc2c(F)cccc2F)c1=O]

¹H NMR (DMSO-d₆): 4.14 (d, J=5.6 Hz, 2H), 5.38 (s, 2H), 7.11 (t, 2H), 7.50 (t, 1H), 8.70 (s, 1H), 8.77 (s, 1H), 10.13 (t, 1H).

Example 37

Preparation of 2-(1-(cyclopropylmethoxy)-4-hydroxy-2-oxo-6-phenoxy-1,2-dihydroquinoline-3-carboxamido)acetic acid

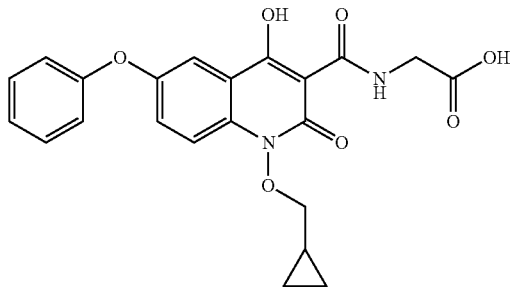 [SMILES: O=C(O)CNC(=O)c1c(O)c2cc(Oc3ccccc3)ccc2n(OCC2CC2)c1=O]

¹H NMR (DMSO-d₆): 0.38-0.39 (m, 2H), 0.58-0.62 (m, 2H), 1.23-1.30 (m, 1H), 4.05 (d, J=7.2 Hz, 2H), 4.10 (d, J=5.2 Hz, 2H), 7.09 (d, J=8.0 Hz, 2H), 7.21 (t, 1H), 7.44 (t, 2H), 7.49 (d, J=2.8 Hz, 1H), 7.60-7.63 (dd, J, 2.4 and 9.2 Hz, 1H), 7.75 (d, J=9.2 Hz, 1H), 10.28 (t, 1H).

Example 38

Preparation of 2-(4-hydroxy-2-oxo-1-(pentan-3-yloxy)-1,2-dihydroquinoline-3-carboxamido)acetic acid

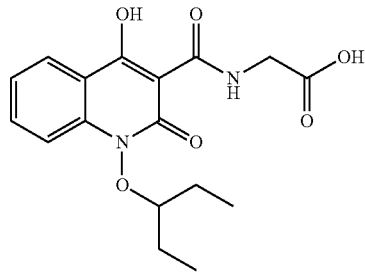 [SMILES: CCC(CC)On1c(=O)c(C(=O)NCC(=O)O)c(O)c2ccccc21]

¹H NMR (DMSO-d₆): 0.94 (t, 6H), 1.58-1.64 (m, 2H), 1.67-1.76 (m, 2H), 4.12 (d, J=5.6 Hz, 2H), 4.45-4.51 (m, 1H), 7.39 (t, 1H), 7.67 (d, J=8.4 Hz, 1H), 7.83 (t, 1H), 8.08 (d, J=7.2 Hz, 1H), 10.23 (t, 1H), 12.93 (bs, 1H).

Example 39

Preparation of 2-(4-(allyloxy)-7-hydroxy-3-methyl-5-oxo-4,5-dihydrothieno[3,2-b]pyridine-6-carboxamido)acetic acid

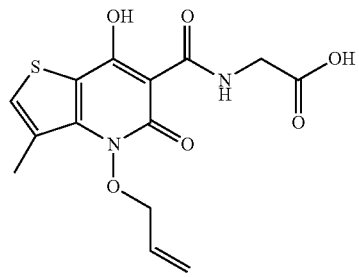 [SMILES: C=CCOn1c(=O)c(C(=O)NCC(=O)O)c(O)c2scc(C)c21]

¹H NMR (DMSO-d₆): 2.47 (s, 3H), 4.04 (d, J=5.6 Hz, 2H), 4.75 (d, J=6.0 Hz, 2H), 5.36 (d, J=10.4 Hz, 1H), 5.45-5.50 (dd, J=1.2 and 17.2 Hz, 1H), 6.02-6.09 (m, 1H), 7.89 (s, 1H), 10.20 (bs, 1H).

Example 40

Preparation of 2-(7-hydroxy-3-methyl-5-oxo-4-propoxy-4,5-dihydrothieno[3,2-b]pyridine-6-carboxamido)acetic acid

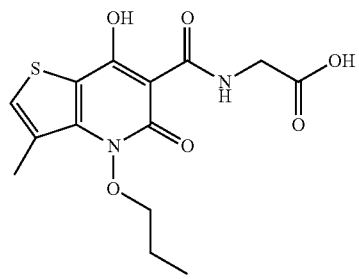 [SMILES: CCCOn1c(=O)c(C(=O)NCC(=O)O)c(O)c2scc(C)c21]

¹H NMR (CD₃OD): 1.07 (t, 3H), 1.84-1.90 (m, 2H), 2.54 (s, 3H), 4.18 (d, 2H), 4.21 (t, 2H), 7.67 (s, 1H).

Example 41

Preparation of 2-(4,7-dihydroxy-3-methyl-5-oxo-4,5-dihydrothieno[3,2-b]pyridine-6-carboxamido)acetic acid

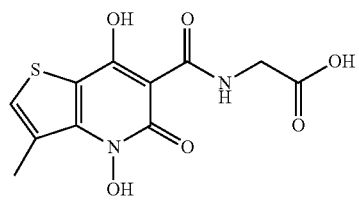 [SMILES: Cc1csc2c(O)c(C(=O)NCC(=O)O)c(=O)n(O)c12]

¹H NMR (CD₃OD): 2.53 (s, 3H), 4.18 (s, 2H), 7.62 (s, 1H).

Example 42

Preparation of 2-(4-((2,6-difluorobenzyl)oxy)-7-hydroxy-3-methyl-5-oxo-4,5-dihydrothieno[3,2-b]pyridine-6-carboxamido)acetic acid

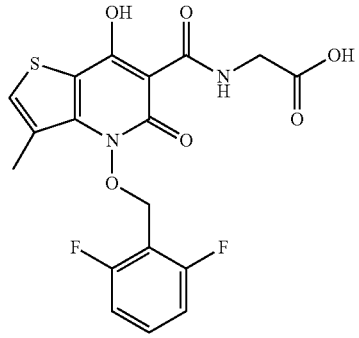 [SMILES: Cc1csc2c(O)c(C(=O)NCC(=O)O)c(=O)n(OCc3c(F)cccc3F)c12]

$^1$H NMR (DMSO-d$_6$): 2.27 (s, 3H), 4.10 (d, J=5.6 Hz, 2H), 5.43 (s, 2H), 7.17 (t, 2H), 7.55 (m, 1H), 7.84 (s, 11H), 10.19 (t, 1H).

Example 43

Preparation of 2-(4-hydroxy-1-(2-(methylthio)ethoxy)-2-oxo-1,2-dihydroquinoline-3-carboxamido)acetic acid

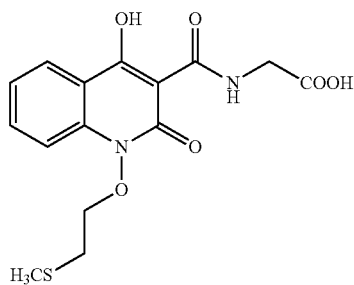

$^1$H NMR (DMSO-d$_6$): 2.16 (s, 3H), 2.94 (t, J=6.4 Hz, 2H), 4.11 (d, J=5.6 Hz, 2H), 4.35 (t, J=6.4 Hz, 2H), 7.40 (t, 1H), 7.79 (d, J=8.0 Hz, 1H), 7.84-7.88 (dd, J=7.2 and 14.4 Hz, 1H), 8.08-8.10 (dd, J=1.2 and 8.0 Hz, 1H), 10.21 (t, 1H), 12.9 (bs, 1H).

Example 44

Preparation of 2-(1-(cyclohexylmethoxy)-4-hydroxy-2-oxo-1,2-dihydroquinoline-3-carboxamido)acetic acid

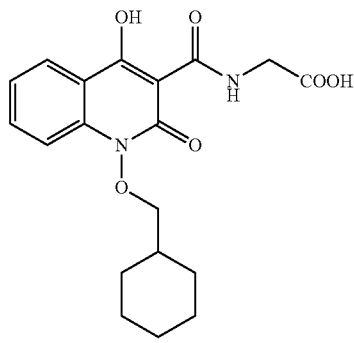 [SMILES: O=C(O)CNC(=O)c1c(O)c2ccccc2n(OCC2CCCCC2)c1=O]

$^1$H NMR (DMSO-d$_6$): 1.13-1.35 (m, 5H), 1.65-1.76 (m, 3H), 1.88-1.91 (bd, 3H), 3.98-4.038 (m, 2H), 4.14 (d, J=5.6 Hz, 2H), 7.41 (t, J=7.6 Hz, 1H), 7.59 (t, J=8.4, Hz, 1H), 7.86-7.90 (m, 1H), 8.09-8.12 (dd, J=7.2 Hz, 1H), 10.25 (t, 1H), 13.06 (bs, 1H).

Example 45

Preparation of (S)-2-(1-(cyclopropylmethoxy)-4-hydroxy-2-oxo-1,2-dihydroquinoline-3-carboxamido)propanoic acid

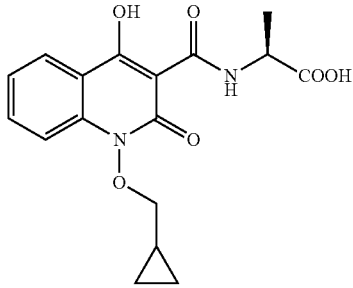 [SMILES: C[C@H](NC(=O)c1c(O)c2ccccc2n(OCC2CC2)c1=O)C(=O)O]

$^1$H NMR (DMSO-d$_6$): 0.38-0.40 (dd, J=4.0 and 5.6 Hz, 2H), 0.57-0.60 (m, 2H), 1.23-1.29 (m, 1H), 1.46 (d, J=7.2 Hz, 3H), 4.04 (d, J=7.6 Hz, 2H), 4.53 (t, J=6.8 Hz, 1H), 7.39-7.44 (m, 1H), 7.70 (d, J=8.4 Hz, 1H), 7.85-7.89 (m, 1H), 8.09-8.11 (dd, J=1.2 and 8.0 Hz, 1H), 10.38 (d, 1H).

Example 46

Preparation of 2-(8-((2,6-difluorobenzyl)oxy)-5-hydroxy-7-oxo-7,8-dihydropyrido[2,3-d]pyrimidine-6-carboxamido)acetic acid

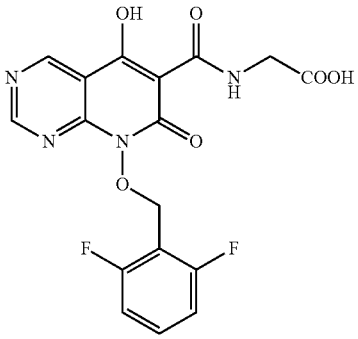 [SMILES: O=C(O)CNC(=O)c1c(O)c2cncnc2n(OCc2c(F)cccc2F)c1=O]

$^1$H NMR (DMSO-d$_6$): 4.05 (d, J=6.0 Hz, 2H), 5.38 (s, 2H), 7.19-7.10 (m, 2H), 7.55-7.47 (m, 1H), 9.17 (s, 1H), 9.31 (s, 1H), 9.94-9.85 (m, 1H).

Example 47

Preparation of (S)-2-(1-(cyclopropylmethoxy)-4-hydroxy-2-oxo-1,2-dihydroquinoline-3-carboxamido)-2-phenylacetic acid

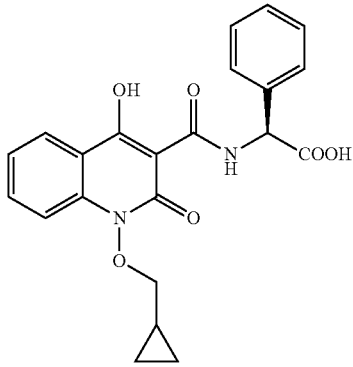 [SMILES: O=C(N[C@H](C(=O)O)c1ccccc1)c1c(O)c2ccccc2n(OCC2CC2)c1=O]

$^1$H NMR (DMSO-d$_6$): 0.41 (m, 2H), 0.57-0.61 (m, 2H), 1.27-1.31 (m, 1H), 4.05 (d, J=7.6 Hz, 2H), 5.57 (d, J=6.4 Hz, 1H), 7.37-7.46 (m, 6H), 7.72 (d, J=8.4 Hz, 1H), 7.85-7.90 (m, 1H), 8.10-8.08 (dd, J=0.8 and 8.0 Hz, 1H), 10.91 (d, J=6.4 Hz, 1H).

Example 48

Preparation of 2-(1-(allyloxy)-4-hydroxy-7-morpholino-2-oxo-1,2-dihydroquinoline-3-carboxamido)acetic acid

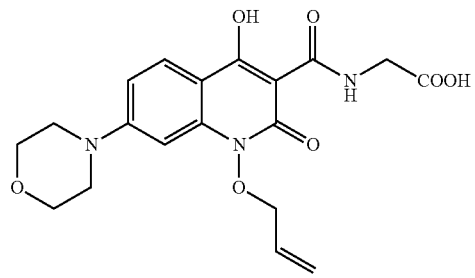 [SMILES: C=CCOn1c(=O)c(C(=O)NCC(=O)O)c(O)c2ccc(N3CCOCC3)cc21]

¹H NMR (DMSO-d₆): 3.40 (t, J=4.6 Hz, 4H), 3.77 (t, J=4.8 Hz, 4H), 4.10 (d, J=5.6 Hz, 2H), 4.72 (d, J=6.4 Hz, 2H), 5.35-5.38 (dd, J=1.6 and 10.4 Hz, 1H), 5.46-5.51 (dd, J=1.2 and 16 Hz, 1H), 6.14-6.20 (m, 1H), 6.82 (d, J=2.4 Hz, 1H), 7.05-7.08 (dd, J=2.0 and 9.2 Hz, 1H), 7.87 (d, J=9.2 Hz, 1H), 10.13 (t, J=5.6 Hz, 1H).

Example 49

Preparation of tert-butyl-2-(1-(cyclopropylmethoxy)-4-hydroxy-2-oxo-1,2-dihydroquinoline-3-carboxamido)acetate

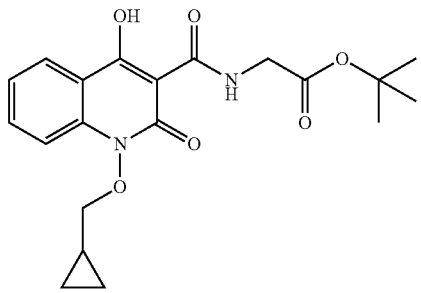 [SMILES: CC(C)(C)OC(=O)CNC(=O)c1c(O)c2ccccc2n(OCC2CC2)c1=O]

¹H NMR (DMSO-d₆): 0.39 (d, J=4.4 Hz, 2H), 0.56-0.61 (m, 2H), 1.26-1.30 (m, 1H), 1.44 (s, 9H), 4.05 (d, J=7.2 Hz, 2H), 4.10 (d, J=5.6 Hz, 2H), 7.39-7.43 (m, 1H), 7.72 (d, J=8.0 Hz, 1H), 7.85-7.89 (m, 1H), 8.09-8.11 (dd, J=1.2 and 8.0 Hz, 1H), 10.24 (t, J=5.6 Hz, 1H).

Example 50

Preparation of 2-(7-chloro-1-(cyclopropylmethoxy)-4-hydroxy-2-oxo-1,2-dihydroquinoline-3-carboxamido)acetic acid

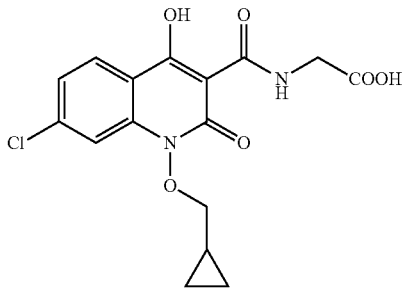 [SMILES: O=C(O)CNC(=O)c1c(O)c2ccc(Cl)cc2n(OCC2CC2)c1=O]

¹H NMR (DMSO-d₆): 0.30-0.55 (m, 2H), 0.59-0.61 (m, 2H), 1.23-1.35 (m, 1H), 4.07 (d, J=7.6 Hz, 2H), 4.12 (t, J=5.6 Hz, 2H), 7.43-7.46 (dd, J=2.0 and 8.8 Hz, 1H), 7.72 (d, J=2.0 Hz, 1H), 8.09 (d, J=8.4 Hz, 1H), 10.15 (t, J=5.6 Hz, 1H), 12.95 (bs, 1H).

Example 51

Preparation of 2-(1-(cyclopentylmethoxy)-4-hydroxy-2-oxo-1,2-dihydroquinoline-3-carboxamido)acetic acid

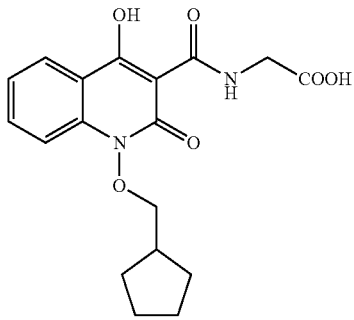 [SMILES: O=C(O)CNC(=O)c1c(O)c2ccccc2n(OCC2CCCC2)c1=O]

¹H NMR (DMSO-d₆): 1.56-1.63 (m, 6H), 1.81-1.86 (m, 2H), 2.49-2.52 (m, 1H), 4.07 (d, J=6.8 Hz, 2H), 4.13 (d, J=5.6 Hz, 2H), 7.40-7.44 (m, 1H), 7.63 (d, J=8.4 Hz, 1H), 7.86-7.90 (m, 1H), 8.10-8.12 (dd, J=1.2 and 2.4 Hz, 1H), 10.25 (t, J=5.6 Hz, 1H).

Example 52

Preparation of 2-(1-(cyclopentyloxy)-4-hydroxy-2-oxo-1,2-dihydroquinoline-3-carboxamido)acetic acid

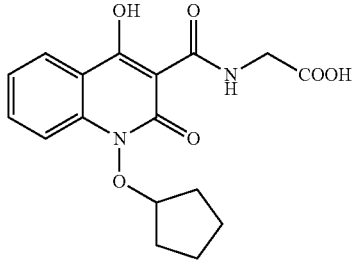 [SMILES: O=C(O)CNC(=O)c1c(O)c2ccccc2n(OC2CCCC2)c1=O]

¹H NMR (DMSO-d₆): 1.60 (d, J=8.0 Hz, 2H), 1.75-1.80 (m, 2H), 1.82-1.89 (m, 4H), 4.13 (d, J=5.6 Hz, 2H), 5.10-5.13 (m, 1H), 7.38-7.42 (m, 1H), 7.61 (d, J=8.4 Hz, 1H), 7.84-7.88 (m, 1H), 8.09-8.11 (dd, J=1.6 and 8.4 Hz, 1H), 10.24 (t, J=5.2 Hz, 1H), 12.95 (bs, 1H).

Example 53

Preparation of methyl-2-(1-(cyclopropylmethoxy)-4-hydroxy-2-oxo-1,2-dihydroquinoline-3-carboxamido)acetate

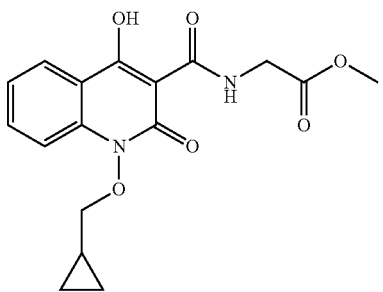 [SMILES: COC(=O)CNC(=O)c1c(O)c2ccccc2n(OCC2CC2)c1=O]

¹H NMR (DMSO-d₆): 0.3-0.6 (m, 2H), 0.79-0.80 (m, 2H), 0.56-0.82 (m, 1H), 3.69 (s, 3H), 4.05 (d, J=7.2 Hz, 2H), 4.22 (d, J=5.6 Hz, 2H), 7.41 (t, J=7.6 Hz, 1H), 7.72 (d, J=8.4 Hz, 1H), 7.87 (d, J=7.2 Hz, 1H), 8.10 (d, J=7.6 Hz, 1H), 10.28 (t, J=6.0 Hz, 1H).

Example 54

Preparation of (S)-2-(1-(cyclopropylmethoxy)-4-hydroxy-2-oxo-1,2-dihydroquinoline-3-carboxamido)-4-methylpentanoic acid

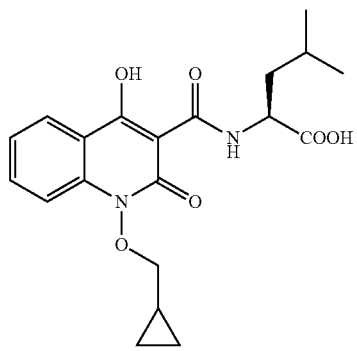 [SMILES: CC(C)C[C@H](NC(=O)c1c(O)c2ccccc2n(OCC2CC2)c1=O)C(=O)O]

$^1$H NMR (DMSO-d$_6$): 0.2-0.4 (m, 2H), 0.5-0.6 (m, 2H), 0.92-0.95 (dd, J=6.0 and 8.0 Hz, 6H), 1.26-1.31 (m, 1H), 1.67-1.73 (m, 3H), 4.05 (d, J=7.6 Hz, 2H), 4.51-4.56 (dd, J=6.8 and 14.4 Hz, 1H), 7.40-7.44 (m, 1H), 7.71 (d, J=8.4 Hz, 1H), 7.85-7.90 (m, 1H), 8.09-8.11 (dd, J=1.2 and 8.0 Hz, 1H), 10.34 (d, J=7.6 Hz, 1H).

Example 55

Preparation of (S)-2-(1-(cyclopropylmethoxy)-4-hydroxy-2-oxo-1,2-dihydroquinoline-3-carboxamido)-3-methylbutanoic acid

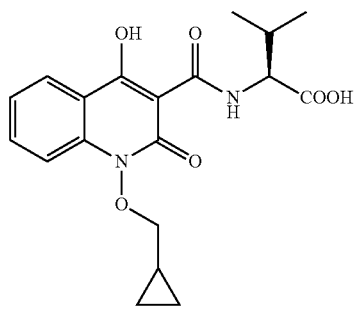 [SMILES: CC(C)[C@H](NC(=O)c1c(O)c2ccccc2n(OCC2CC2)c1=O)C(=O)O]

$^1$HNMR (DMSO-d$_6$): 0.2-0.5 (m, 2H), 0.6-0.9 (m, 2H), 1.15-1.26 (m, 6H), 1.27-1.32 (m, 1H), 2.24-2.30 (m, 1H), 4.02-4.09 (m, 2H), 4.45-4.49 (dd, J=4.8 and 8.4 Hz, 1H), 7.40-7.44 (m, 1H), 7.72 (d, J=8.4 Hz, 1H), 7.85-7.90 (m, 1H), 8.09-8.11 (dd, J=0.8 and 8.0 Hz, 1H), 10.45 (d, J=8.4 Hz, 1H).

Example 56

Preparation of 3-(1-(cyclopropylmethoxy)-4-hydroxy-2-oxo-1,2-dihydroquinoline-3-carboxamido)propanoic acid

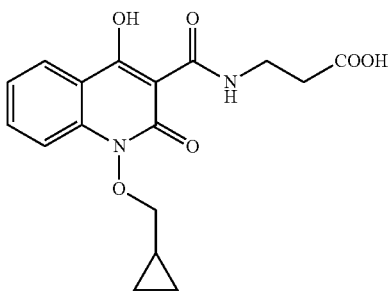 [SMILES: O=C(O)CCNC(=O)c1c(O)c2ccccc2n(OCC2CC2)c1=O]

$^1$H NMR (DMSO-d$_6$): 0.34-0.39 (m, 2H), 0.56-0.61 (m, 2H), 1.23-1.29 (m, 1H), 2.57 (t, J=6.4 Hz, 2H), 3.55-3.60 (dd, J=6.4 and 12.8 Hz, 2H), 4.02 (d, J=7.2 Hz, 2H), 7.40 (t, J=7.6 Hz, 1H), 7.69 (d, J=8.4 Hz, 1H), 7.83-7.88 (m, 1H), 8.09 (d, J=7.2 Hz, 1H), 10.15 (t, J=6.0 Hz, 1H).

Example 57

Preparation of 2-(1-(allyloxy)-4-hydroxy-2-oxo-7-phenoxy-1,2-dihydroquinoline-3-carboxamido)acetic acid

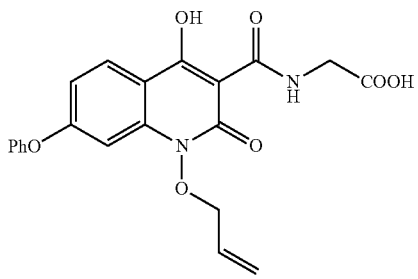

$^1$H NMR (DMSO-d$_6$): 4.09 (d, J=5.2 Hz, 2H), 4.63 (d, J=6.4 Hz, 2H), 5.23-5.35 (m, 2H), 5.88-5.98 (m, 1H), 6.92 (s, 1H), 7.03 (d, J=9.6 Hz, 1H), 7.24 (d, J=8.0 Hz, 2H), 7.32 (t, J=7.2 Hz, 1H), 7.52 (t, J=7.6 Hz, 2H), 8.09 (d, J=8.8 Hz, 1H), 10.13 (bs, 1H).

Example 58

Preparation of (S)-2-(1-(cyclopropylmethoxy)-4-hydroxy-2-oxo-1,2-dihydroquinoline-3-carboxamido)-3-phenylpropanoic acid

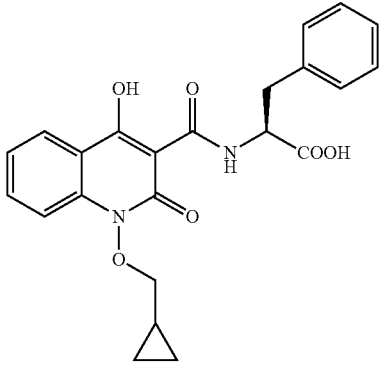 [SMILES: O=C(N[C@@H](Cc1ccccc1)C(=O)O)c1c(O)c2ccccc2n(OCC2CC2)c1=O]

$^1$H NMR (DMSO-d$_6$): 0.35-0.38 (m, 2H), 0.56-0.59 (m, 2H), 1.23-1.29 (m, 1H), 3.15 (m, 1H), 3.22 (m, 1H), 4.02 (m, 2H), 4.80-4.82 (m, 1H), 7.20-7.30 (m, 5H), 7.38-7.42 (m, 1H), 7.70 (d, J=8.4 Hz, 1H), 7.84-7.86 (m, 1H), 8.07-8.09 (dd, J=0.8 and 8.0 Hz, 1H), 10.34 (d, J=7.6 Hz, 1H).

Example 59

Preparation of (S)-4-(1-(cyclopropylmethoxy)-4-hydroxy-2-oxo-1,2-dihydroquinoline-3-carboxamido)-2-hydroxybutanoic acid

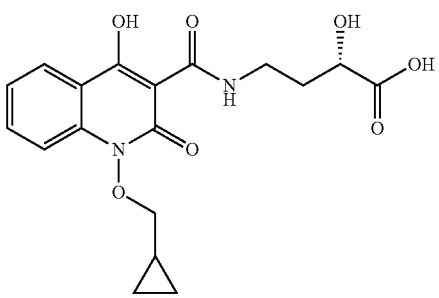 [SMILES: O=C(NCC[C@H](O)C(=O)O)c1c(O)c2ccccc2n(OCC2CC2)c1=O]

$^1$H NMR (DMSO-d$_6$): 0.3-0.4 (m, 2H), 0.5-0.7 (m, 2H), 1.22-1.30 (m, 1H), 1.75-1.84 (m, 1H), 1.91-2.02 (m, 1H), 3.47-3.52 (dd, J=6.4 and 13.2 Hz, 2H), 4.00-4.05 (m, 3H), 5.42 (t, J=2.4 Hz, 1H), 7.40 (t, J=7.6 Hz, 1H), 7.69 (d, J=8.4 Hz, 1H), 7.85 (t, J=7.2 Hz, 1H), 8.09 (d, J=8.0 Hz, 1H), 10.01 (t, J=5.2 Hz, 1H), 12.46 (bs, 1H).

Example 60

Preparation of 5-(1-(cyclopropylmethoxy)-4-hydroxy-2-oxo-1,2-dihydroquinoline-3-carboxamido)pentanoic acid

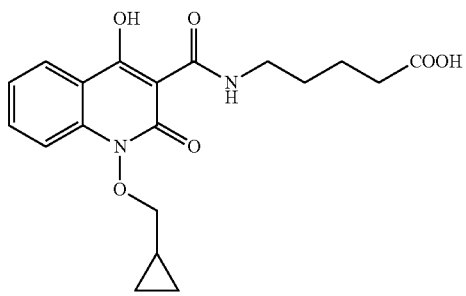 [SMILES: O=C(O)CCCCNC(=O)c1c(O)c2ccccc2n(OCC2CC2)c1=O]

$^1$H NMR (DMSO-d$_6$): 0.35-0.39 (m, 2H), 0.56-0.59 (m, 2H), 1.27-1.33 (m, 1H), 1.57 (t, J=3.2 Hz, 3H), 2.27 (t, J=6.8 Hz, 2H), 3.83 (t, J=6.0 Hz, 2H), 4.03 (d, J=7.6 Hz, 2H), 7.38-7.42 (m, 1H), 7.70 (d, J=8.4 Hz, 1H), 7.83-7.87 (m, 1H), 8.08-8.10 (dd, J=1.2 and 8.0 Hz, 1H), 10.05 (t, J=5.6 Hz, 1H), 12.03 (bs, 1H).

Example 61

Preparation of 2-(4-hydroxy-2-oxo-1-(prop-2-yn-1-yloxy)-1,2-dihydroquinoline-3-carboxamido)acetic acid

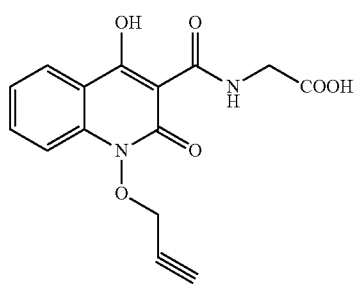 [SMILES: C#CCOn1c(=O)c(C(=O)NCC(=O)O)c(O)c2ccccc21]

$^1$H NMR (DMSO-d$_6$): 3.59 (bs, 1H), 4.00 (d, J=5.6 Hz, 2H), 5.03 (s, 2H), 7.37 (bs, 1H), 7.66 (bs, 1H), 7.82 (bs, 1H), 8.09 (d, J=7.6 Hz, 1H), 10.19 (bs, 1H).

Example 62

Preparation of 2-(1-((2-fluorobenzyl)oxy)-4-hydroxy-2-oxo-1,2-dihydroquinoline-3-carboxamido)acetic acid

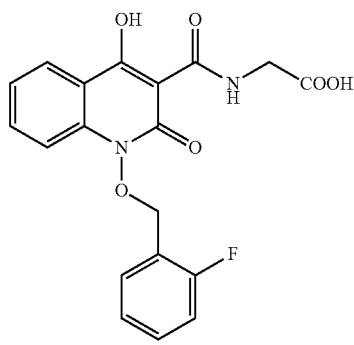 [SMILES: O=C(O)CNC(=O)c1c(O)c2ccccc2n(OCc2ccccc2F)c1=O]

$^1$H NMR (DMSO-d$_6$): 4.15 (d, J=5.6 Hz, 2H), 5.32 (s, 2H), 7.26-7.31 (m, 2H), 7.39 (t, J=7.6 Hz, 1H), 7.47-7.52 (m, 1H), 7.57 (d, J=8.0 Hz, 1H), 7.65-7.70 (m, 1H), 7.80-7.84 (m, 1H), 8.08-8.11 (dd, J=0.8 and 8.0 Hz, 1H), 10.26 (t, J=5.6 Hz, 1H).

Example 63

Preparation of 2-(1-ethoxy-4-hydroxy-2-oxo-1,2-dihydroquinoline-3-carboxamido)acetic acid

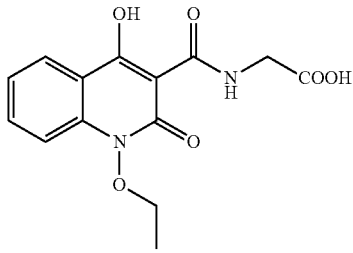 [SMILES: CCOn1c(=O)c(C(=O)NCC(=O)O)c(O)c2ccccc21]

$^1$H NMR (DMSO-d$_6$): 1.39 (t, J=7.0 Hz, 3H), 4.12 (d, J=5.6 Hz, 2H), 4.21-4.26 (q, J=6.8 Hz, 2H), 7.42 (t, J=7.6 Hz, 1H), 7.65 (d, J=8.4 Hz, 1H), 7.87 (t, J=7.8 Hz, 1H), 8.10 (d, J=8.0 Hz, 1H), 10.27 (bs, 1H).

Example 64

Preparation of 2-(4-hydroxy-2-oxo-1-((4-(trifluoromethoxy)benzyl)oxy)-1,2-dihydroquinoline-3-carboxamido)acetic acid

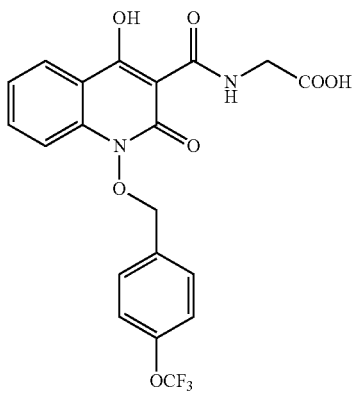

$^1$H NMR (DMSO-d$_6$): 4.15 (d, J=5.6 Hz, 2H), 5.25 (s, 2H), 7.39-7.46 (m, 3H), 7.63 (d, J=8.4 Hz, 1H), 7.78-7.86 (m, 3H), 8.10-8.12 (dd, J=1.2 and 8.4 Hz, 1H), 10.27 (t, J=5.4 Hz, 1H).

Example 65

Preparation of 2-(1-((2,4-difluorobenzyl)oxy)-4-hydroxy-2-oxo-1,2-dihydroquinoline-3-carboxamido)acetic acid

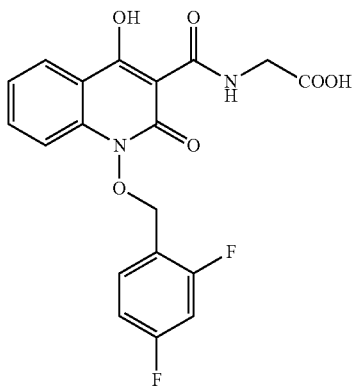 [SMILES: O=C(O)CNC(=O)c1c(O)c2ccccc2n(OCc2ccc(F)cc2F)c1=O]

¹H NMR (DMSO-d₆): 4.15 (d, J=5.2 Hz, 2H), 5.30 (s, 2H), 7.14-7.19 (m, 1H), 7.34-7.45 (m, 2H), 7.54 (d, J=8.4 Hz, 1H), 7.72-7.78 (m, 1H), 7.80-7.84 (m, 1H), 8.09 (d, J=7.2 Hz, 1H), 10.24 (bs, 1H).

Example 66

Preparation of 2-(1-((2,6-difluorobenzyl)oxy)-4-hydroxy-2-oxo-1,2-dihydro-1,8-naphthyridine-3-carboxamido)acetic acid

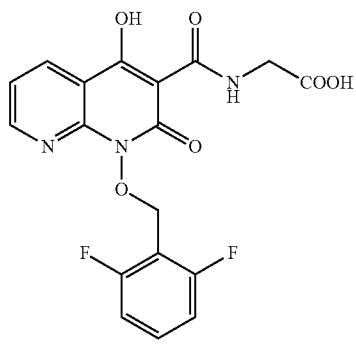 [SMILES: O=C(O)CNC(=O)c1c(O)c2cccnc2n(OCc2c(F)cccc2F)c1=O]

¹H NMR (DMSO-d₆): 4.13 (d, J=5.2 Hz, 2H), 5.3.8 (s, 2H), 7.09 (t, J=8.0 Hz, 2H), 7.40-7.51 (m, 2H), 8.45 (d, J=7.6 Hz, 1H), 8.71 (d, J=2.8 Hz, 1H), 10.11 (bs, 1H).

Example 67

Preparation of 2-(4-hydroxy-1-((4-methoxybenzyl)oxy)-2-oxo-1,2-dihydroquinoline-3-carboxamido)acetic acid

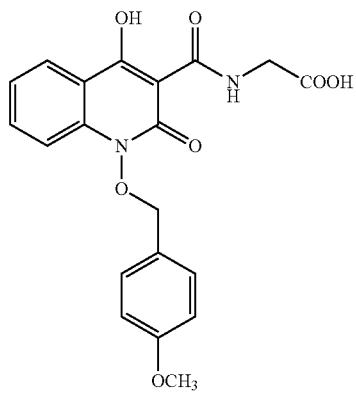 [SMILES: COc1ccc(COn2c(=O)c(C(=O)NCC(=O)O)c(O)c3ccccc32)cc1]

¹H NMR (DMSO-d₆): 3.78 (s, 3H), 4.17 (d, J=5.6 Hz, 2H), 5.14 (s, 2H), 7.01 (d, J=8.4 Hz, 2H), 7.39-7.43 (m, 1H), 7.58 (d, J=8.8 Hz, 2H), 7.65 (d, J=8.8 Hz, 1H), 7.83-7.87 (m, 1H), 8.09-8.12 (dd, J=1.2 and 8.0 Hz, 1H), 10.30 (t, J=5.6 Hz, 1H), 12.96 (bs, 1H).

Example 68

Preparation of 2-(1-(cyclopropylmethoxy)-4-hydroxy-2-oxo-1,2-dihydro-1,8-naphthyridine-3-carboxamido)acetic acid

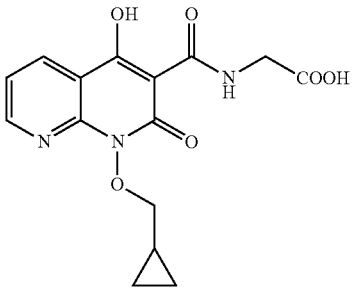 [SMILES: O=C(O)CNC(=O)c1c(O)c2cccnc2n(OCC2CC2)c1=O]

¹H NMR (DMSO-d₆): 0.36-0.39 (m, 2H), 0.54-0.59 (m, 2H), 1.23-1.28 (m, 1H), 4.02 (d, J=7.6 Hz, 2H), 4.13 (d, J=5.6 Hz, 2H), 7.45-7.48 (dd, J=4.4 and 7.6 Hz, 1H), 8.47-8.49 (dd, J=2.0 and 8.0 Hz, 1H), 8.84-8.85 (dd, J=1.6 and 4.4 Hz, 1H), 10.19 (bs, 1H).

Example 69

Preparation of 2-(4-hydroxy-2-oxo-1-(2,2,2-trifluoroethoxy)-1,2-dihydroquinoline-3-carboxamido)acetic acid

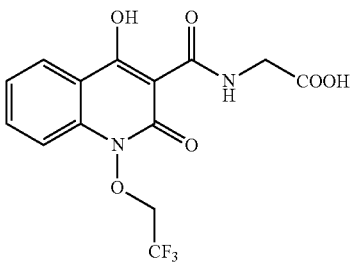 [SMILES: O=C(O)CNC(=O)c1c(O)c2ccccc2n(OCC(F)(F)F)c1=O]

¹H NMR (DMSO-d₆): 4.12 (d, J=5.6 Hz, 2H), 4.99-5.06 (q, J=9.2 Hz, 2H), 7.44 (bs, 1H), 7.58 (d, J=8.0 Hz, 1H), 7.90 (bs, 1H), 8.12-8.14 (dd, J=1.2 and 8.0 Hz, 1H), 10.11 (bs, 1H).

Example 70

Preparation of 2-(1-(cyclopropylmethoxy)-4-hydroxy-2-oxo-1,2-dihydro-1,7-naphthyridine-3-carboxamido)acetic acid

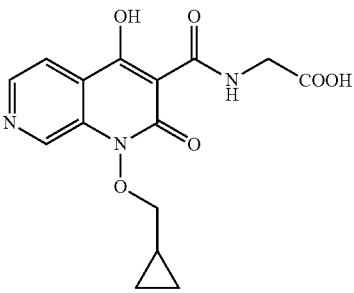 [SMILES: O=C(O)CNC(=O)c1c(O)c2ccncc2n(OCC2CC2)c1=O]

¹H NMR (DMSO-d₆): 0.36-0.39 (m, 2H), 0.57-0.60 (m, 2H), 1.29-1.35 (m, 1H), 4.11-4.14 (m, 4H), 7.94 (d, J=5.2 Hz, 1H), 8.57 (d, J=5.2 Hz, 1H), 9.10 (s, 1H), 10.22 (bs, 1H).

Example 71

Preparation of 2-(6-cyano-1-(cyclopropylmethoxy)-4-hydroxy-2-oxo-1,2-dihydroquinoline-3-carboxamido)acetic acid

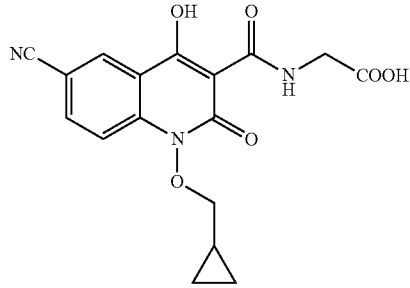 [SMILES: N#Cc1ccc2c(c1)c(O)c(C(=O)NCC(=O)O)c(=O)n2OCC1CC1]

¹H NMR (DMSO-d₆): 0.36-0.39 (m, 2H), 0.56-0.61 (m, 2H), 1.26-1.35 (m, 1H), 4.05 (d, J=7.6 Hz, 2H), 4.13 (d, J=5.6 Hz, 2H), 7.83 (d, J=8.8 Hz, 1H), 8.19-8.28 (m, 1H), 8.50 (d, J=1.6 Hz, 1H), 10.11 (bs, 1H).

Example 72

Preparation of 2-(8-(benzyloxy)-5-hydroxy-7-oxo-7,8-dihydropyrido[2,3-d]pyrimidine-6-carboxamido)acetic acid

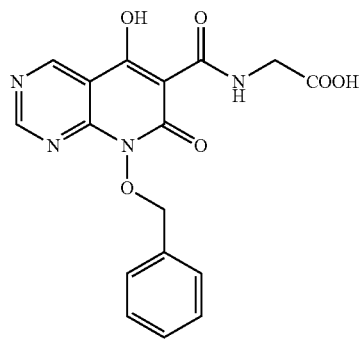 [SMILES: O=C(O)CNC(=O)c1c(O)c2cncnc2n(OCc2ccccc2)c1=O]

¹H NMR (DMSO-d₆): 4.15 (d, J=5.6 Hz, 2H), 5.21 (s, 2H), 7.43-7.48 (m, 3H), 7.66-7.68 (dd, J=2.0 and 8.0 Hz, 2H), 9.32 (s, 1H), 9.36 (s, 1H), 10.20 (bs, 1H).

Example 73

Preparation of (S)-2-(4-hydroxy-2-oxo-1-propoxy-1,2-dihydroquinoline-3-carboxamido)propanoic acid

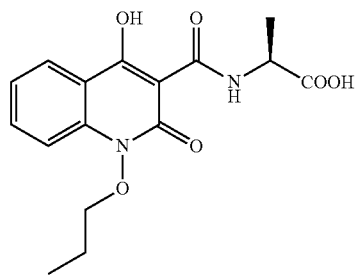 [SMILES: CCCOn1c(=O)c(C(=O)N[C@@H](C)C(=O)O)c(O)c2ccccc21]

¹H NMR (DMSO-d₆): 1.06 (t, J=7.4 Hz, 3H), 1.45 (d, J=7.2 Hz, 3H), 1.80-1.86 (m, 2H), 4.14 (t, J=6.6 Hz, 2H), 4.51-4.55 (q, 1H), 7.40-7.44 (m, 1H), 7.63 (d, J=8.0 Hz, 1H), 7.86-7.90 (m, 1H), 8.10-8.12 (dd, J=1.2 and 8.4 Hz, 1H), 10.39 (d, J=6.8 Hz, 1H), 13.13 (bs, 1H).

Example 74

Preparation of 2-(4-hydroxy-1-(2-methoxyethoxy)-2-oxo-1,2-dihydroquinoline-3-carboxamido)acetic acid

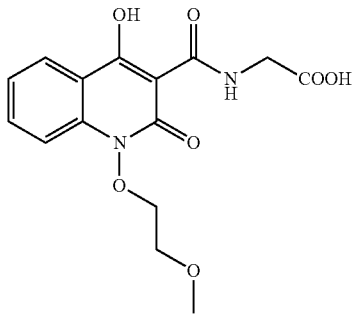 [SMILES: COCCOn1c(=O)c(C(=O)NCC(=O)O)c(O)c2ccccc21]

¹H NMR (DMSO-d₆): 3.30 (s, 3H), 3.68 (t, J=3.6 Hz, 2H), 4.11 (d, J=5.6 Hz, 2H), 4.33 (t, J=4.0 Hz, 2H), 7.37-7.42 (m, 1H), 7.73 (d, J=8.4 Hz, 1H), 7.83-7.87 (m, 1H), 8.07-8.09 (dd, J=1.2 and 8.0 Hz, 1H), 10.21 (t, J=5.6 Hz, 1H), 12.94 (bs, 1H).

Example 75

Preparation of 2-(4-hydroxy-2-oxo-6-phenoxy-1-propoxy-1,2-dihydroquinoline-3-carboxamido)acetic acid

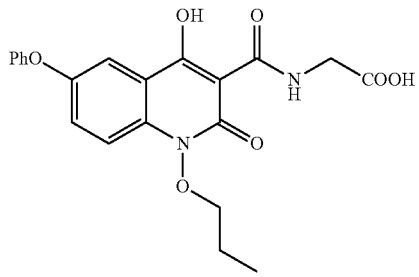

¹H NMR (DMSO-d₆): 1.06 (t, J=7.4 Hz, 3H), 1.08-1.85 (m, 2H), 4.09 (d, J=5.6 Hz, 2H), 4.15 (d, J=6.6 Hz, 2H), 7.09-7.11 (dd, J=1.2 and 8.8 Hz, 2H), 7.21 (t, J=7.4 Hz, 1H), 7.42-7.46 (m, 2H), 7.50 (d, J=2.8 Hz, 1H), 7.60-7.63 (dd, J=2.8 and 9.2 Hz, 1H), 7.67 (d, J=9.2 Hz, 1H), 10.29 (bs, 1H).

Example 76

Preparation of 2-(1-((4-cyclopropylbut-3-en-1-yl)oxy)-4-hydroxy-2-oxo-1,2-dihydroquinoline-3-carboxamido)acetic acid

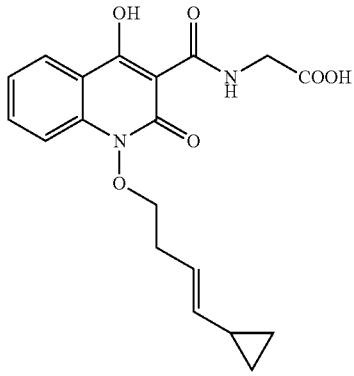 [SMILES: O=C(O)CNC(=O)c1c(O)c2ccccc2n(OCC/C=C/C2CC2)c1=O]

¹H NMR (DMSO-d₆): 0.32-0.34 (m, 2H), 0.66-0.68 (m, 2H), 1.39-1.42 (m, 1H), 2.50 (m, 2H), 4.13 (d, J=7.6 Hz, 2H), 4.17-4.20 (m, 2H), 5.13-5.19 (m, 1H), 5.55-5.60 (m, 1H), 7.42 (t, J=7.4 Hz, 1H), 7.65 (d, J=8.4 Hz, 1H), 7.84-7.88 (m, 1H), 8.10 (d, J=8.0 Hz, 1H), 10.24 (bs, 1H), 12.95 (bs, 1H).

Example 77

Preparation of 2-(1-(heptan-4-yloxy)-4-hydroxy-2-oxo-1,2-dihydroquinoline-3-carboxamido)acetic acid

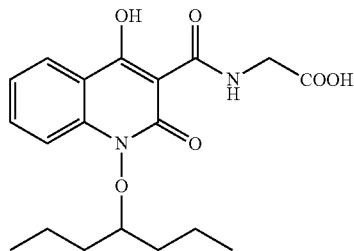 [SMILES: CCCC(CCC)On1c(=O)c(C(=O)NCC(=O)O)c(O)c2ccccc21]

$^1$H NMR (DMSO-$d_6$): 0.86 (t, J=7.2 Hz, 6H), 1.39-1.48 (m, 4H), 1.53-1.63 (m, 4H), 4.13 (d, J=5.6 Hz, 2H), 4.60-4.64 (m, 1H), 7.39 (t, J=7.6 Hz, 1H), 7.67 (d, J=8.4 Hz, 1H), 7.81-7.85 (m, 1H), 8.08 (d, J=7.6 Hz, 1H), 10.21 (t, J=5.4 Hz, 1H), 12.91 (bs, 1H).

Example 78

Preparation of ethyl-2-(4-(cyclopropylmethoxy)-7-hydroxy-5-oxo-4,5-dihydrothieno[3,2-b]pyridine-6-carboxamido)acetate

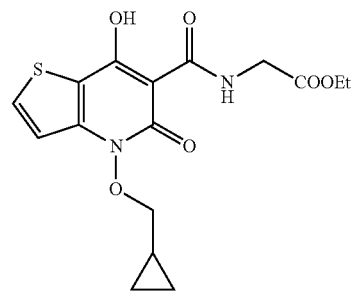 [SMILES: CCOC(=O)CNC(=O)c1c(O)c2sccc2n(OCC2CC2)c1=O]

$^1$H NMR (DMSO-$d_6$): 0.31-0.34 (m, 2H), 0.53-0.57 (m, 2H), 1.20-1.25 (m, 4H), 4.09 (d, J=7.6 Hz, 2H), 4.12-4.19 (m, 4H), 7.40 (d, J=5.2 Hz, 1H), 8.28 (d, J=5.2 Hz, 1H), 10.25 (t, J=5.6 Hz, 1H).

Example 79

Preparation of 2-(4-(cyclopropylmethoxy)-7-hydroxy-5-oxo-4,5-dihydrothieno[3,2-b]pyridine-6-carboxamido)acetic acid

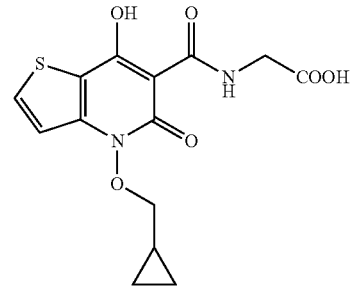 [SMILES: O=C(O)CNC(=O)c1c(O)c2sccc2n(OCC2CC2)c1=O]

$^1$H NMR (DMSO-$d_6$): 0.32-0.35 (m, 2H), 0.53-0.57 (m, 2H), 1.21-1.27 (m, 1H), 4.10 (t, J=7.2 Hz, 4H), 7.40 (d, J=5.2 Hz, 1H), 8.27 (d, J=5.6 Hz, 1H), 10.23 (t, J=4.6 Hz, 1H).

Example 80

Preparation of 2-(1-(heptyloxy)-4-hydroxy-2-oxo-1,2-dihydroquinoline-3-carboxamido)acetic acid

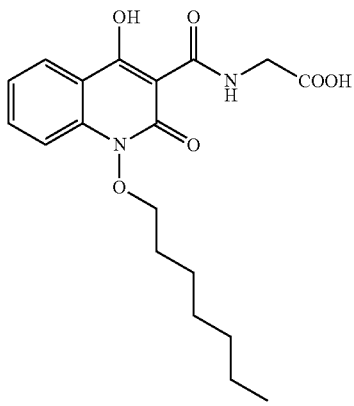 [SMILES: CCCCCCCOn1c(=O)c(C(=O)NCC(=O)O)c(O)c2ccccc21]

$^1$H NMR (DMSO-$d_6$): 0.88 (t, J=6.8 Hz, 3H), 1.26-1.38 (m, 6H), 1.45-1.51 (m, 2H), 1.77-1.84 (m, 2H), 4.12 (d, J=5.6 Hz, 2H), 4.17 (t, J=6.6 Hz, 2H), 7.41 (t, 1H), 7.61 (d, J=8.8 Hz, 1H), 7.85-7.89 (dd, J=1.2 and 8.4 Hz, 1H), 8.10 (d, J=7.2 Hz, 1H), 10.25 (bs, 1H).

The following compounds can be prepared by procedure similar to those described above with appropriate variations of reactions, reaction conditions, reagents and quantities of reagents which are within the scope of person skilled in the art.

Example 81

2-(4-hydroxy-2-oxo-1-((6-(trifluoromethyl)pyridin-3-yl)methoxy)-1,2-dihydroquinoline-3-carboxamido)acetic acid

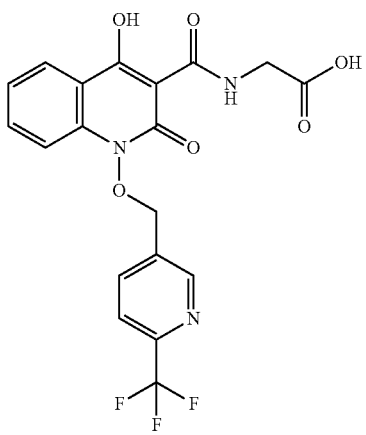 [SMILES: O=C(O)CNC(=O)c1c(O)c2ccccc2n(OCc2ccc(C(F)(F)F)nc2)c1=O]

Example 82

2-(4-hydroxy-2-oxo-1-(4-(trifluoromethyl)phenethoxy)-1,2-dihydroquinoline-3-carboxamido)acetic acid

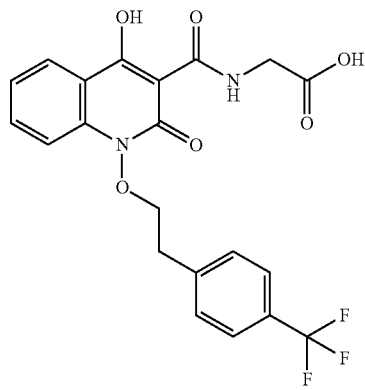 [SMILES: O=C(O)CNC(=O)c1c(O)c2ccccc2n(OCCc2ccc(C(F)(F)F)cc2)c1=O]

Example 83

2-(4-hydroxy-2-oxo-1-(4-(trifluoromethyl)phenoxy)-1,2-dihydro-1,8-naphthyridine-3-carboxamido)acetic acid

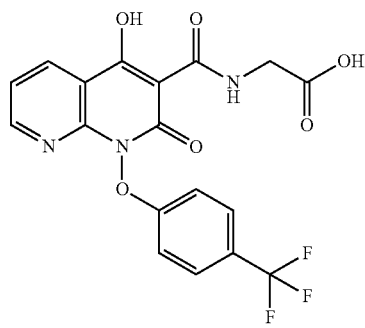 [SMILES: O=C(O)CNC(=O)c1c(O)c2cccnc2n(Oc2ccc(C(F)(F)F)cc2)c1=O]

Example 84

2-(4-hydroxy-2-oxo-1-(4-(trifluoromethyl)phenethoxy)-1,2-dihydro-1,8-naphthyridine-3-carboxamido) acetic acid

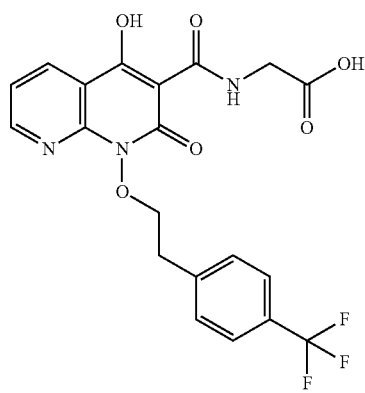

Example 85

2-(1-(but-2-yn-1-yloxy)-4-hydroxy-2-oxo-1,2-dihydroquinoline-3-carboxamido)acetic acid

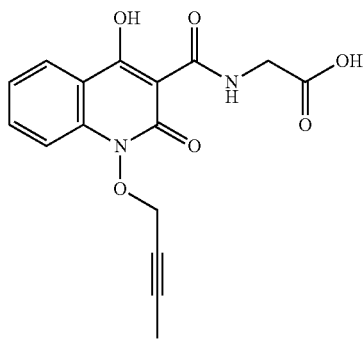 [SMILES: CC#CCOn1c(=O)c(C(=O)NCC(=O)O)c(O)c2ccccc21]

Example 86

2-(4-hydroxy-2-oxo-1-(3,3,3-trifluoropropoxy)-1,2-dihydroquinoline-3-carboxamido)acetic acid

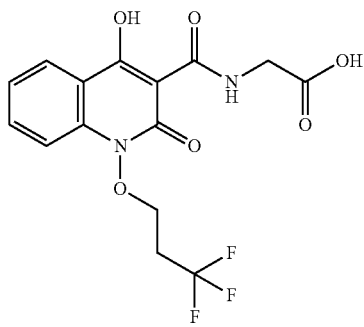 [SMILES: O=C(O)CNC(=O)c1c(O)c2ccccc2n(OCCC(F)(F)F)c1=O]

Example 87

2-(1-(2-amino-2-oxoethoxy)-4-hydroxy-2-oxo-1,2-dihydroquinoline-3-carboxamido)acetic acid

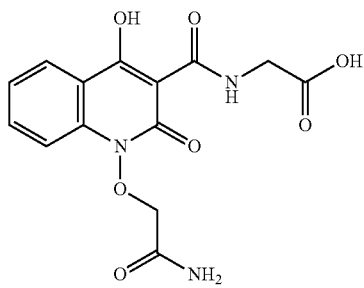 [SMILES: NC(=O)COn1c(=O)c(C(=O)NCC(=O)O)c(O)c2ccccc21]

Example 88

2-(1-(benzo[d]oxazol-2-ylmethoxy)-4-hydroxy-2-oxo-1,2-dihydroquinoline-3-carboxamido)acetic acid

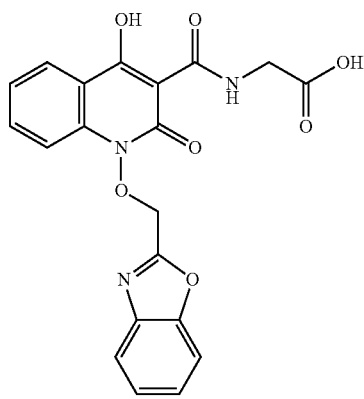 [SMILES: O=C(O)CNC(=O)c1c(O)c2ccccc2n(OCc2nc3ccccc3o2)c1=O]

Example 89

2-(1-(benzo[d]thiazol-2-ylmethoxy)-6-chloro-4-hydroxy-2-oxo-1,2-dihydroquinoline-3-carboxamido)acetic acid

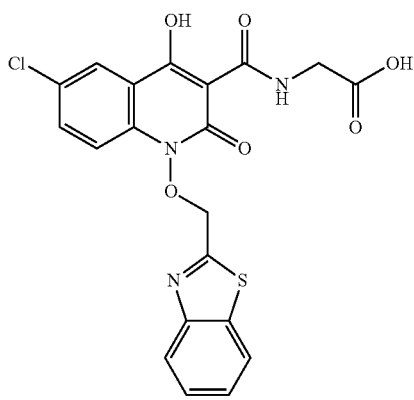 [SMILES: O=C(O)CNC(=O)c1c(O)c2cc(Cl)ccc2n(OCc2nc3ccccc3s2)c1=O]

Example 90

2-(1-(allyloxy)-4-hydroxy-8-methoxy-2-oxo-1,2-dihydroquinoline-3-carboxamido)acetic acid

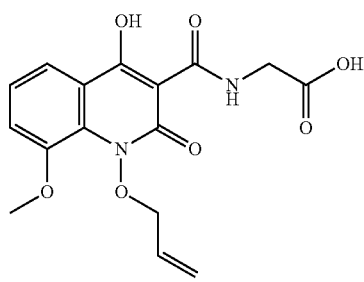 [SMILES: C=CCOn1c(=O)c(C(=O)NCC(=O)O)c(O)c2cccc(OC)c21]

Example 91

2-(1-ethoxy-4-hydroxy-8-methoxy-2-oxo-1,2-dihydroquinoline-3-carboxamido)acetic acid

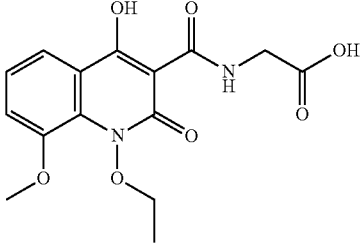 [SMILES: CCOn1c(=O)c(C(=O)NCC(=O)O)c(O)c2cccc(OC)c21]

Example 92

2-(4-hydroxy-1-(oxazol-2-ylmethoxy)-2-oxo-1,2-dihydroquinoline-3-carboxamido)acetic acid

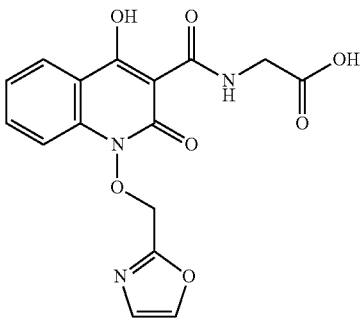 [SMILES: O=C(O)CNC(=O)c1c(O)c2ccccc2n(OCc2ncco2)c1=O]

Example 93

2-(1-(allyloxy)-6-cyano-4-hydroxy-2-oxo-1,2-dihydroquinoline-3-carboxamido)acetic acid

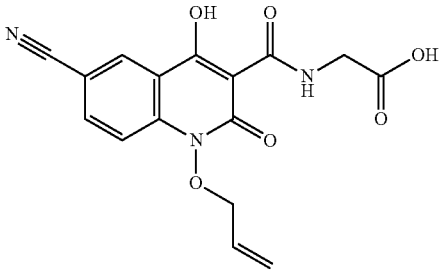 [SMILES: C=CCOn1c(=O)c(C(=O)NCC(=O)O)c(O)c2cc(C#N)ccc21]

Example 94

2-(1-(allyloxy)-4-hydroxy-6-nitro-2-oxo-1,2-dihydroquinoline-3-carboxamido)acetic acid

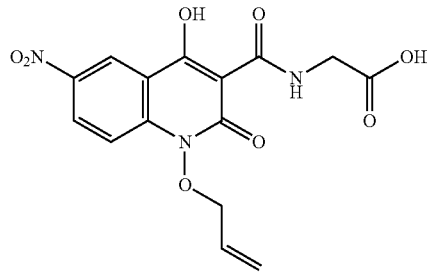 [SMILES: C=CCOn1c(=O)c(C(=O)NCC(=O)O)c(O)c2cc([N+](=O)[O-])ccc21]

Example 95

2-(4-hydroxy-1-methoxy-2-oxo-6-(trifluoromethyl)-1,2-dihydroquinoline-3-carboxamido)acetic acid

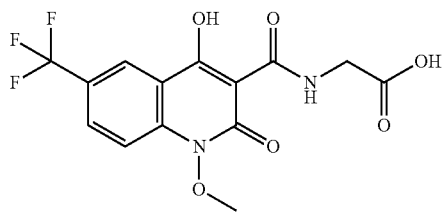 [SMILES: COn1c(=O)c(C(=O)NCC(=O)O)c(O)c2cc(C(F)(F)F)ccc21]

Example 96

2-(4,6-dihydroxy-2-oxo-1-propoxy-1,2-dihydro-quinoline-3-carboxamido)acetic acid

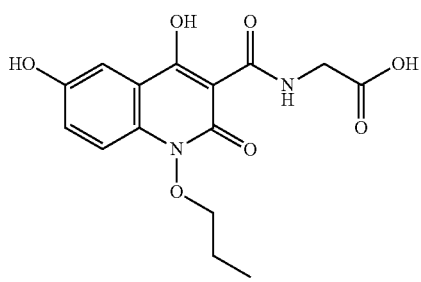 [SMILES: CCCOn1c(=O)c(C(=O)NCC(=O)O)c(O)c2cc(O)ccc21]

Example 97

2-(1-((4-(tert-butyl)benzyl)oxy)-4-hydroxy-2-oxo-1,2-dihydroquinoline-3-carboxamido)acetic acid

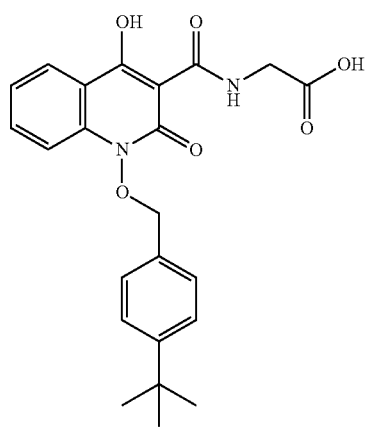 [SMILES: CC(C)(C)c1ccc(COn2c(=O)c(C(=O)NCC(=O)O)c(O)c3ccccc32)cc1]

Example 98

2-(1-([1,1-biphenyl]-4-ylmethoxy)-4-hydroxy-2-oxo-1,2-dihydroquinoline-3-carboxamido)acetic acid

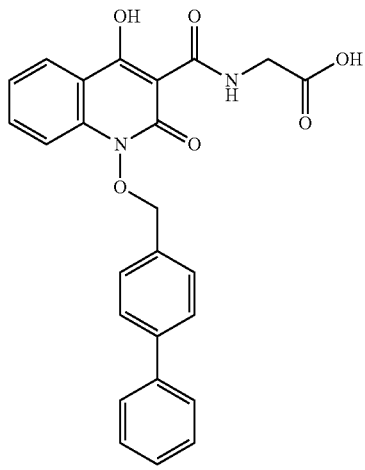 [SMILES: O=C(O)CNC(=O)c1c(O)c2ccccc2n(OCc2ccc(-c3ccccc3)cc2)c1=O]

Example 99

2-(4-hydroxy-1-((4-(oxazol-2-yl)benzyl)oxy)-2-oxo-1,2-dihydroquinoline-3-carboxamido)acetic acid

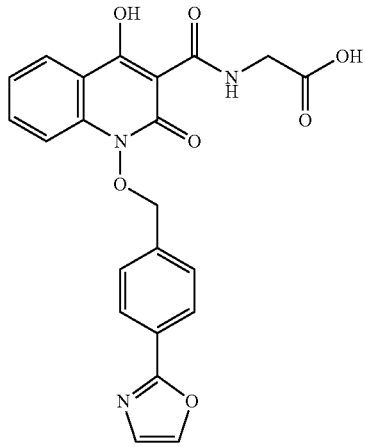 [SMILES: O=C(O)CNC(=O)c1c(O)c2ccccc2n(OCc2ccc(-c3ncco3)cc2)c1=O]

Example 100

2-(1-(benzyloxy)-4-hydroxy-2-oxo-6-phenoxy-1,2-dihydroquinoline-3-carboxamido)acetic acid

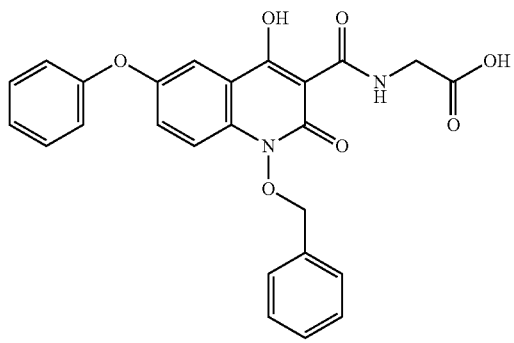 [SMILES: O=C(O)CNC(=O)c1c(O)c2cc(Oc3ccccc3)ccc2n(OCc2ccccc2)c1=O]

Example 101

2-(1-(benzyloxy)-4-hydroxy-2-oxo-6-(pyridin-2-yloxy)-1,2-dihydroquinoline-3-carboxamido)acetic acid

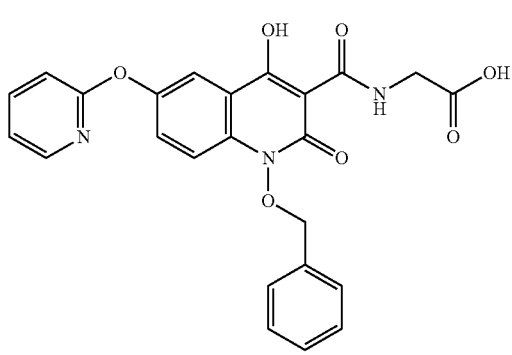 [SMILES: O=C(O)CNC(=O)c1c(O)c2cc(Oc3ccccn3)ccc2n(OCc2ccccc2)c1=O]

Example 102

2-(1-(benzyloxy)-4-hydroxy-2-oxo-6-(phenylthio)-1,2-dihydroquinoline-3-carboxamido)acetic acid

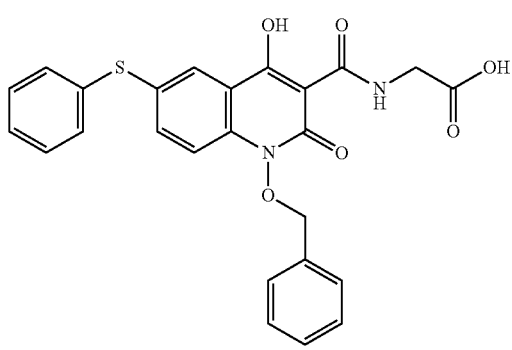 [SMILES: O=C(O)CNC(=O)c1c(O)c2cc(Sc3ccccc3)ccc2n(OCc2ccccc2)c1=O]

Example 103

2-(1-(benzyloxy)-4-hydroxy-6-(methylsulfonyl)-2-oxo-1,2-dihydroquinoline-3-carboxamido)acetic acid

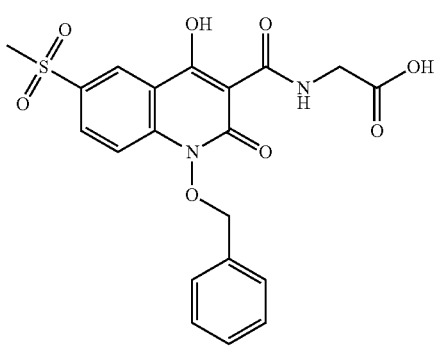 [SMILES: CS(=O)(=O)c1ccc2c(c1)c(O)c(C(=O)NCC(=O)O)c(=O)n2OCc1ccccc1]

Example 104

2-(1-(benzyloxy)-4-hydroxy-2-oxo-6-phenyl-1,2-dihydroquinoline-3-carboxamido)acetic acid

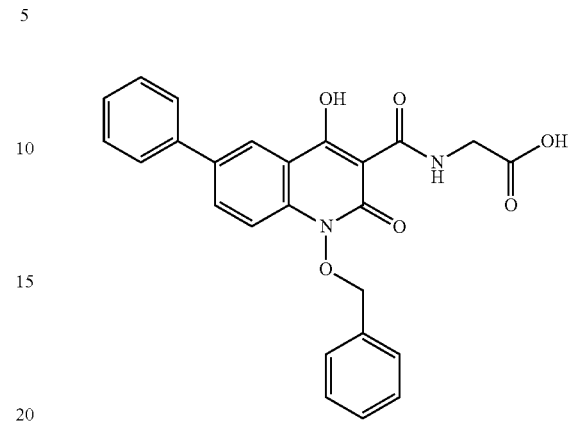

Example 105

2-(1-(benzyloxy)-4-hydroxy-6-(4-methoxyphenyl)-2-oxo-1,2-dihydroquinoline-3-carboxamido)acetic acid

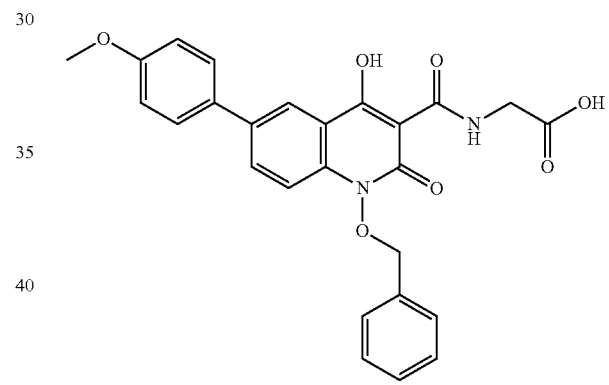

Example 106

2-(1-(benzyloxy)-4-hydroxy-6-(5-methoxypyridin-2-yl)-2-oxo-1,2-dihydroquinoline-3-carboxamido)acetic acid

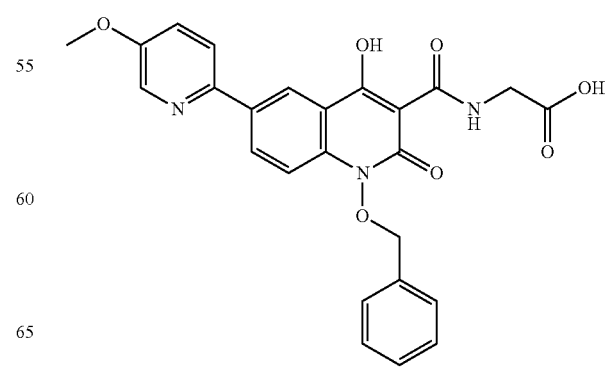

Example 107

2-(1-(benzyloxy)-4-hydroxy-2-oxo-6-sulfamoyl-1,2-dihydroquinoline-3-carboxamido)acetic acid

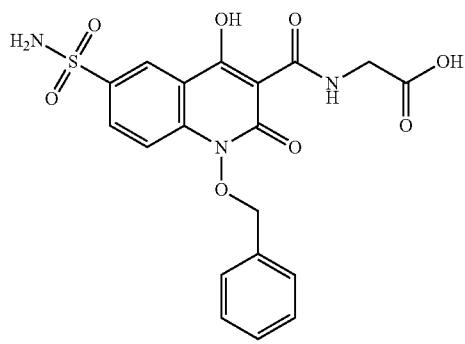 [SMILES: NS(=O)(=O)c1ccc2c(c1)c(O)c(C(=O)NCC(=O)O)c(=O)n2OCc1ccccc1]

Example 108

2-(1-(benzyloxy)-4-hydroxy-6-(methylsulfonamido)-2-oxo-1,2-dihydroquinoline-3-carboxamido)acetic acid

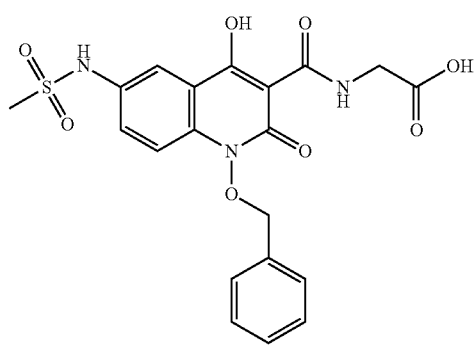 [SMILES: CS(=O)(=O)Nc1ccc2c(c1)c(O)c(C(=O)NCC(=O)O)c(=O)n2OCc1ccccc1]

Example 109

2-(1-(benzyloxy)-4-hydroxy-2-oxo-6-(trifluoromethoxy)-1,2-dihydroquinoline-3-carboxamido) acetic acid

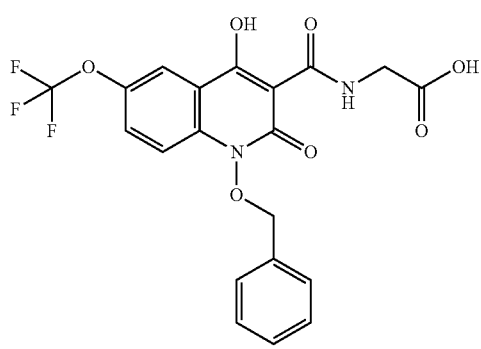 [SMILES: O=C(O)CNC(=O)c1c(O)c2cc(OC(F)(F)F)ccc2n(OCc2ccccc2)c1=O]

Example 110

2-(6-benzoyl-4-hydroxy-2-oxo-1-((4-(trifluoromethyl)benzyl)oxy)-1,2-dihydroquinoline-3-carboxamido)acetic acid

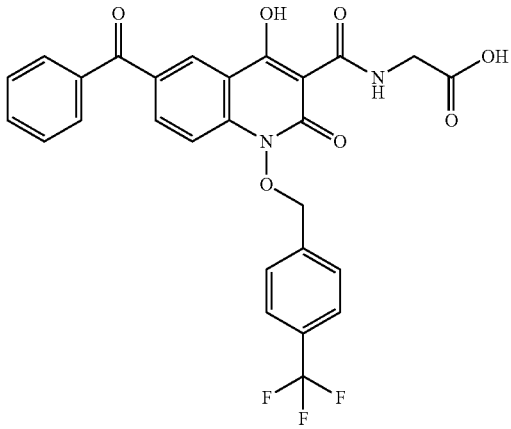 [SMILES: O=C(O)CNC(=O)c1c(O)c2cc(C(=O)c3ccccc3)ccc2n(OCc2ccc(C(F)(F)F)cc2)c1=O]

Example 111

2-(1-(benzyloxy)-4-hydroxy-N-methyl-2-oxo-1,2-dihydroquinoline-3-carboxamido) acetic acid

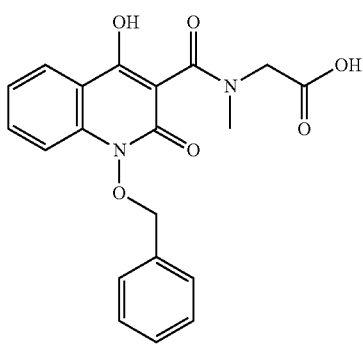 [SMILES: CN(CC(=O)O)C(=O)c1c(O)c2ccccc2n(OCc2ccccc2)c1=O]

Example 112

2-(1-(benzyloxy)-4-hydroxy-2-oxo-1,2-dihydroquinoline-3-carboxamido)-2-methylpropanoic acid

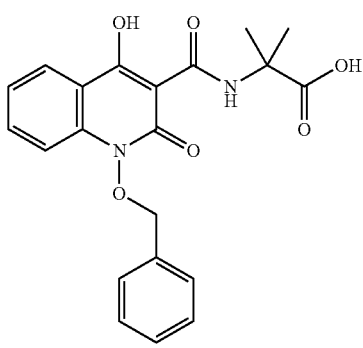 [SMILES: CC(C)(NC(=O)c1c(O)c2ccccc2n(OCc2ccccc2)c1=O)C(=O)O]

Example 113

1-(1-(benzyloxy)-4-hydroxy-2-oxo-1,2-dihydro-quinoline-3-carboxamido)cyclopropanecarboxylic acid

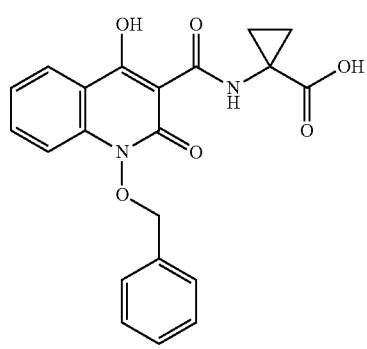 [SMILES: O=C(NC1(C(=O)O)CC1)c1c(O)c2ccccc2n(OCc2ccccc2)c1=O]

Example 114

3-(1-(benzyloxy)-4-hydroxy-2-oxo-1,2-dihydro-quinoline-3-carboxamido)propanoic acid

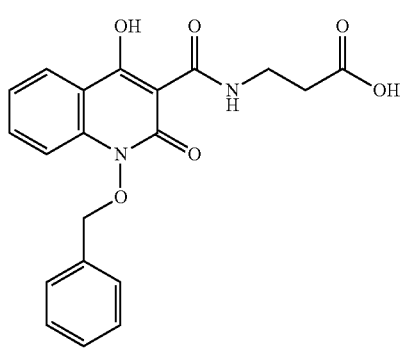 [SMILES: O=C(O)CCNC(=O)c1c(O)c2ccccc2n(OCc2ccccc2)c1=O]

Example 115

1-(benzyloxy)-4-hydroxy-N-(2-(methylsulfonamido)-2-oxoethyl)-2-oxo 1,2-dihydroquinoline-3-carboxamide

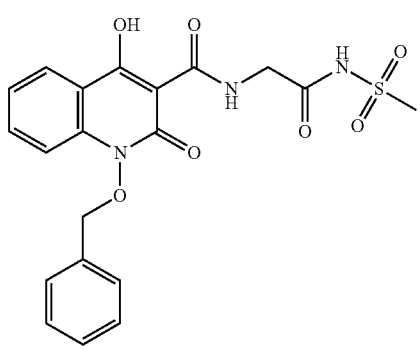 [SMILES: CS(=O)(=O)NC(=O)CNC(=O)c1c(O)c2ccccc2n(OCc2ccccc2)c1=O]

Example 116

1-(benzyloxy)-4-hydroxy-2-oxo-N-(2-oxo-2-(thiophene-2-carboxamido)ethyl) 1,2-dihydroquinoline-3-carboxamide

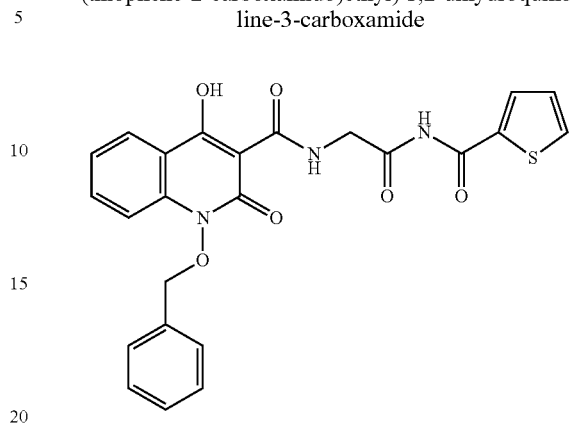

Example 117

2-(4-hydroxy-1-methoxy-2-oxo-1,2-dihydro-1,5-naphthyridine-3-carboxamido)acetic acid

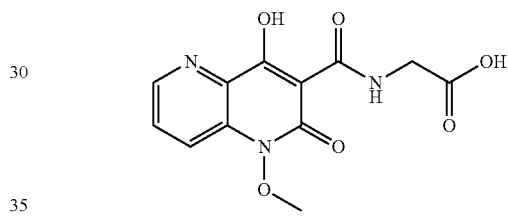

Example 118

2-(8-hydroxy-5-methoxy-6-oxo-5,6-dihydropyrido[2,3-b]pyrazine-7-carboxamido)acetic acid

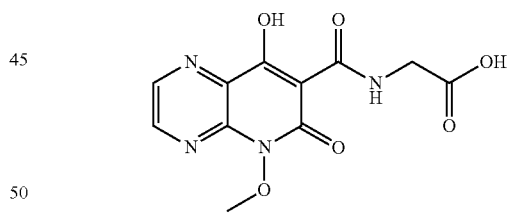

Example 119

2-(7-hydroxy-4-methoxy-5-oxo-4,5-dihydrofuro[3,2-b]pyridine-6-carboxamido)acetic acid

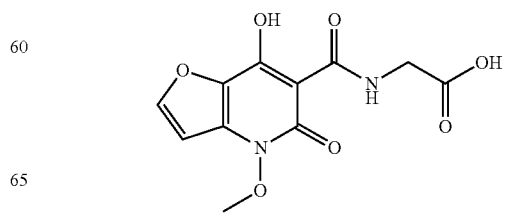

Example 120

2-(4-(cyclopropylmethoxy)-7-hydroxy-5-oxo-4,5-dihydrofuro[3,2-b]pyridine-6-carboxamido)acetic acid

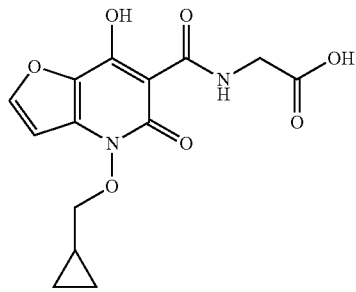 [SMILES: O=C(O)CNC(=O)c1c(O)c2occc2n(OCC2CC2)c1=O]

Example 121

2-(7-hydroxy-5-oxo-4-propoxy-4,5-dihydrofuro[3,2-b]pyridine-6-carboxamido)acetic acid

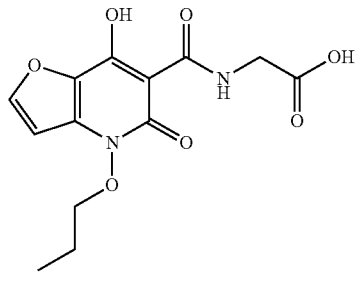 [SMILES: CCCOn1c(=O)c(C(=O)NCC(=O)O)c(O)c2occc21]

Example 122

2-(7-hydroxy-4-methoxy-5-oxo-4,5-dihydrothieno[3,2-b]pyridine-6-carboxamido)acetic acid

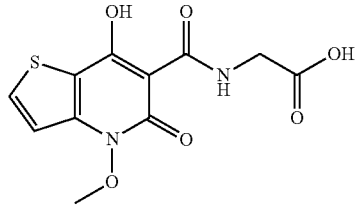

Example 123

2-(7-hydroxy-4-methoxy-1-methyl-5-oxo-4,5-dihydro-1H-pyrrolo[3,2-b]pyridine-6-carboxamido)acetic acid

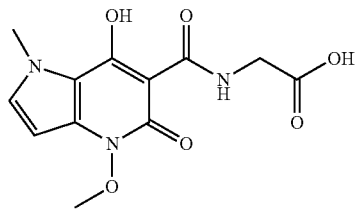 [SMILES: COn1c(=O)c(C(=O)NCC(=O)O)c(O)c2c1ccn2C]

Example 124

2-(7-hydroxy-1-methyl-5-oxo-4-propoxy-4,5-dihydro-1H-pyrrolo[3,2-b]pyridine-6-carboxamido)acetic acid

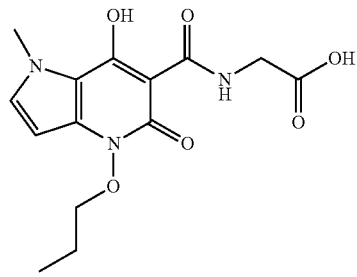 [SMILES: CCCOn1c(=O)c(C(=O)NCC(=O)O)c(O)c2c1ccn2C]

Example 125

2-(7-hydroxy-4-methoxy-5-oxo-4,5-dihydrothiazolo[4,5-b]pyridine-6-carboxamido)acetic acid

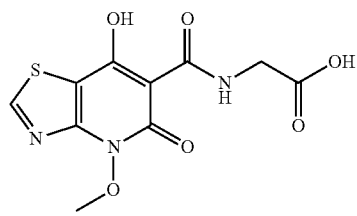

Example 126

2-(7-hydroxy-5-oxo-4-propoxy-4,5-dihydrothiazolo[5,4-b]pyridine-6-carboxamido)acetic acid

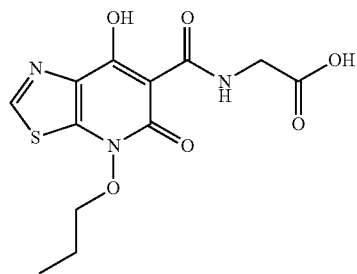 [SMILES: CCCOn1c(=O)c(C(=O)NCC(=O)O)c(O)c2ncsc21]

Example 127

2-(4-hydroxy-7-methoxy-1-methyl-6-oxo-6,7-dihydro-1H-pyrazolo[3,4-b]pyridine-5-carboxamido)acetic acid

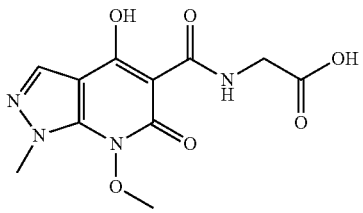 [SMILES: COn1c(=O)c(C(=O)NCC(=O)O)c(O)c2cnn(C)c21]

Example 128

2-(7-hydroxy-4-methoxy-5-oxo-4,5-dihydrooxazolo[4,5-b]pyridine-6-carboxamido)acetic acid

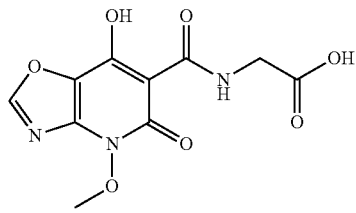 [SMILES: COn1c(=O)c(C(=O)NCC(=O)O)c(O)c2ocnc21]

Example 129

2-(7-hydroxy-5-oxo-4-propoxy-4,5-dihydrooxazolo[4,5-b]pyridine-6-carboxamido) acetic acid

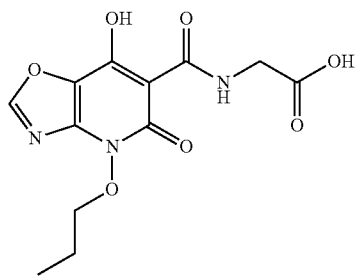 [SMILES: CCCOn1c(=O)c(C(=O)NCC(=O)O)c(O)c2ocnc21]

Example 130

2-(4-hydroxy-1-methoxy-2-oxo-1,2,5,7-tetrahydrothieno[3,4-b]pyridine-3-carboxamido)acetic acid

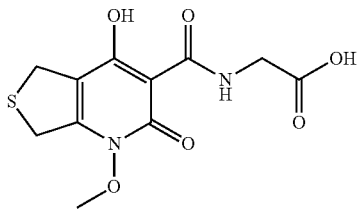 [SMILES: COn1c2c(c(O)c(C(=O)NCC(=O)O)c1=O)CSC2]

Example 131

2-(7-ethoxy-4-hydroxy-6-oxo-6,7-dihydrothieno[2,3-b]pyridine-5-carboxamido)acetic acid

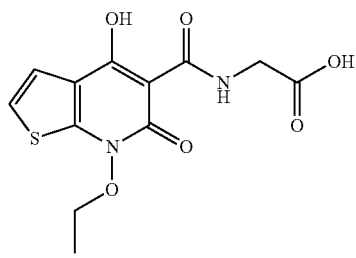 [SMILES: CCOn1c(=O)c(C(=O)NCC(=O)O)c(O)c2ccsc21]

Example 132

2-(7-(cyclopropylmethoxy)-4-hydroxy-6-oxo-6,7-dihydrothieno[2,3-b]pyridine-5-carboxamido)acetic acid

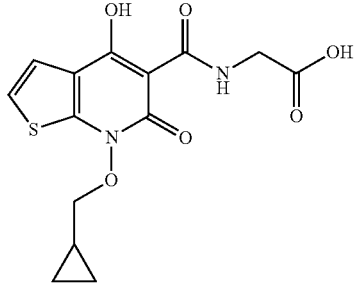 [SMILES: O=C(O)CNC(=O)c1c(O)c2ccsc2n(OCC2CC2)c1=O]

Example 133

2-(4-hydroxy-1-methoxy-6,6-dioxido-2-oxo-1,2,5,7-tetrahydrothieno[3,4-b]pyridine-3-carboxamido) acetic acid

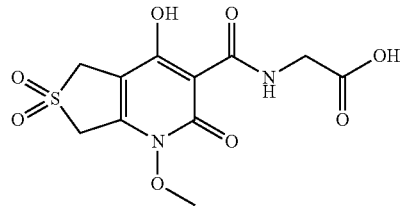 [SMILES: COn1c2c(c(O)c(C(=O)NCC(=O)O)c1=O)CS(=O)(=O)C2]

Example 134

2-(7-ethoxy-4-hydroxy-1-methyl-6-oxo-6,7-dihydro-1H-pyrazolo[3,4-b]pyridine-5-carboxamido)acetic acid

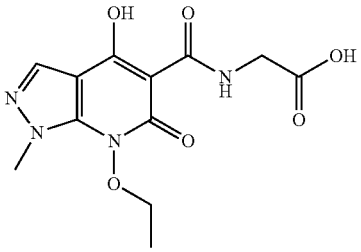 [SMILES: CCOn1c(=O)c(C(=O)NCC(=O)O)c(O)c2cnn(C)c21]

Example 135

2-(7-ethoxy-4-hydroxy-6-oxo-1-phenyl-6,7-dihydro-1H-pyrazolo[3,4-b]pyridine-5-carboxamido)acetic acid

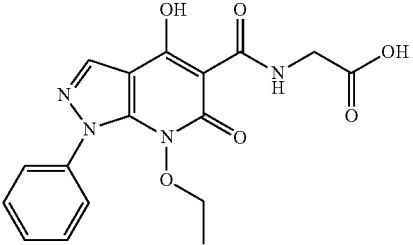 [SMILES: CCOn1c(=O)c(C(=O)NCC(=O)O)c(O)c2cnn(-c3ccccc3)c21]

Example 136

2-(7-ethoxy-4-hydroxy-3-methyl-6-oxo-6,7-dihydroisothiazolo[5,4-b]pyridine-5-carboxamido)acetic acid

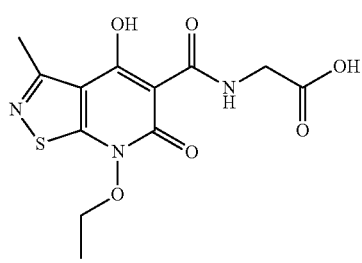 [SMILES: CCOn1c(=O)c(C(=O)NCC(=O)O)c(O)c2c(C)nsc21]

Example 137

2-(4-hydroxy-2-oxo-1-(2-(2-oxooxazolidin-3-yl)ethoxy)-1,2-dihydroquinoline-3-carboxamido)acetic acid

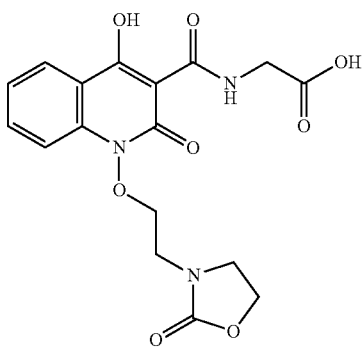 [SMILES: O=C(O)CNC(=O)c1c(O)c2ccccc2n(OCCN2CCOC2=O)c1=O]

Example 138

2-(4-hydroxy-2-oxo-1-((4-(trifluoromethyl)benzyl)oxy)-1,2,5,6,7,8-hexahydroquinoline-3-carboxamido)acetic acid

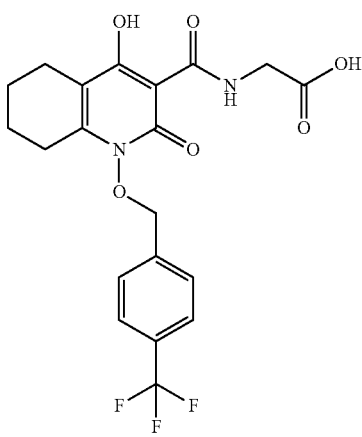 [SMILES: O=C(O)CNC(=O)c1c(O)c2c(n(OCc3ccc(C(F)(F)F)cc3)c1=O)CCCC2]

Example 139

2-(4-hydroxy-2-oxo-1-propoxy-1,2,5,6,7,8-hexahydroquinoline-3-carboxamido)acetic acid

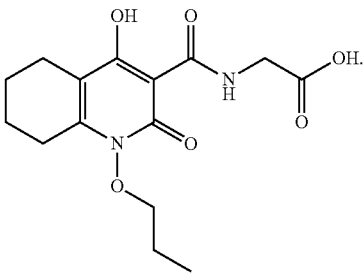 [SMILES: CCCOn1c2c(c(O)c(C(=O)NCC(=O)O)c1=O)CCCC2]

Demonstration of In Vivo Efficacy of Compounds (1) Protocol for Estimating Circulating EPO Release in Mice C57 Mice were administered various doses (10 mg/kg, 30 mg/kg, 50 mg/kg, 100 mg/kg) of compounds of the present invention by oral gavage at 10 ml/kg. Six hours after compound administration, mice were bled by retro-orbital puncture, under light ether anesthesia in microfuge tubes containing 2% EDTA (10 μl/100 μl of blood). Plasma was separated and analyzed for EPO content by mouse EPO ELISA. As shown in table 1, few selected compounds have shown significant increase in EPO levels.

TABLE 1

| Compound | EPO (ng/mL) oral gavage 10 mg/kg | EPO (ng/mL) oral gavage 30 mg/kg | EPO (ng/mL) oral gavage 50 mg/kg | EPO (ng/mL) oral gavage 100 mg/kg |
|---|---|---|---|---|
| Example 1 | ND | ND | ND | 7118 |
| Example 2 | 396 | 4822 | ND | ND |
| Example 11 | ND | ND | ND | 1593 |
| Example 12 | ND | ND | ND | 7056 |
| Example 15 | 315 | ND | 4269 | ND |
| Example 16 | 100 | ND | 8043 | ND |
| Example 20 | ND | ND | 3797 | ND |
| Example 21 | 190 | 6234 | ND | ND |
| Example 62 | ND | ND | 398 | ND |
| Example 63 | ND | ND | 539 | ND |
| Example 67 | ND | ND | 477 | ND |

ND (not determined).
EPO levels in control = 62 ng/mL (2) Protocol for Estimating Hemoglobin Levels in Mice C57 mice were administered compounds of the present invention at 10 ml/kg by oral route daily once in the morning for 7 consecutive days at 20 mg/kg. On 8th day animals were bled by retro-orbital puncture under light ether anesthesia in microfuge tubes containing 2% EDTA (10 μl/100 μl of blood) for whole blood. Hemoglobin, Reticulocyte count and RBC count were measured using standard procedures. As shown in table 2, few selected compounds have shown significant increase in Hb levels.

TABLE 2

| Compound | Hemoglobin (g/dL) Control | Hemoglobin (g/dL) 20 mg/kg compound |
|---|---|---|
| Example 2 | 13.7 | 16.3 |
| Example 8 | 14.1 | 15.8 |

TABLE 2-continued

| Compound | Hemoglobin (g/dL) Control | Hemoglobin (g/dL) 20 mg/kg compound |
|---|---|---|
| Example 10 | 13.4 | 13.8 |
| Example 15 | 13.6 | 13.2 |
| Example 21 | 14 | 15.8 |
| Example 25 | 13.7 | 14.9 |
| Example 28 | 13.7 | 16.9 |
| Example 36 | 13.5 | 14.2 |
| Example 38 | 14.5 | 15.8 |
| Example 40 | 14.5 | 16.1 |
| Example 42 | 14.5 | 16.1 |
| Example 44 | 13.4 | 16.1 |
| Example 45 | 13.5 | 15.7 |
| Example 46 | 13.5 | 14.2 |
| Example 47 | 13.4 | 14.2 |
| Example 48 | 13.5 | 13.9 |
| Example 49 | 13.4 | 14.1 |
| Example 53 | 13.4 | 15.2 |
| Example 54 | 13.4 | 13.7 |
| Example 55 | 13.4 | 13 |
| Example 56 | 14.5 | 14.4 |
| Example 58 | 13.4 | 14 |
| Example 69 | 14.1 | 15.7 |
| Example 70 | 14.1 | 13.9 |
| Example 73 | 13.5 | 16.2 |
| Example 76 | 14.5 | 17.1 |
| Example 77 | 14.5 | 15.5 |
| Example 79 | 14.5 | 14.3 |

The novel compounds of the present invention can be formulated into suitable pharmaceutically acceptable compositions by combining with suitable excipients by techniques and processes and concentrations as are well known.

The compounds of formula (I) or pharmaceutical compositions containing them are useful in treating various disorders including anemia of different types and conditions associated with ischemia/hypoxia. Compounds are suitable for humans and other warm blooded animals, and may be administered either by oral, topical or parenteral administration.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

We claim:
1. A compound of the general formula (I),

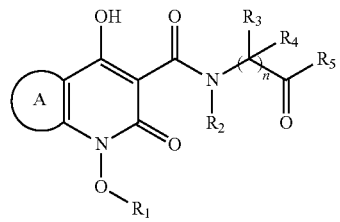

(I)

wherein
$R_1$ represents hydrogen, optionally substituted $(C_1-C_{10})$ alkyl, $(C_2-C_{10})$alkenyl, $(C_2-C_{10})$alkynyl, $(C_3-C_8)$cycloalkyl, $(C_5-C_8)$cycloalkenyl, aryl, heteroaryl, heterocyclyl, aralkyl, cycloalkanylalkyl, heteroaralkyl, heterocyclylalkyl groups;

$R_2$ represents hydrogen, optionally substituted alkyl, cycloalkyl, aryl, heteroaryl, heterocyclyl and acyl groups;

$R_3$ and $R_4$ each independently represents hydrogen, optionally substituted alkyl, cycloalkyl, aryl, heterocyclyl, heteroaryl groups; or $R_3$ and $R_4$ together with the carbon atom to which they are attached forms a cycloalkyl, or heterocyclyl group wherein the heterocyclyl group may further contain one or more heteroatoms selected from O, N & S;

$R_5$ is selected from the group comprising of $-OR_6$, $-COOR_6$, $-NR_7COR_6$ and $-NR_7SO_2R_6$ wherein each of $R_6$ and $R_7$ at each occurrence are independently selected from the group comprising of hydrogen, optionally substituted groups selected from alkyl, cycloalkyl, aryl, heterocyclyl and heteroaryl;

'A' represents a 5-7 membered saturated or unsaturated carbocyclic or heterocyclic ring system wherein the heterocyclic ring further contains one or more heteroatoms selected from N, O or $S(O)_m$; The said cycle representing 'A' is further substituted by one or more substituents selected from the group of substituents represented by $R_8$;

'm' represents integers from 0-2 and
'n' represents integers from 1-4.

2. The compound as claimed in claim 1, wherein $R_1$ is selected from $(C_1-C_{10})$alkyl, $(C_2-C_{10})$alkenyl, $(C_2-C_{10})$alkynyl, $(C_3-C_8)$cycloalkyl, cycloalkanyl alkyl, aryl, heteroaryl, heterocyclyl, aralkyl, heterocyclylalkyl groups.

3. The compound as claimed in claim 1, wherein $R_2$ is selected from hydrogen, optionally substituted alkyl, cycloalkyl and acyl groups.

4. The compound as claimed in claim 1, wherein $R_3$ and $R_4$ is independently selected from hydrogen, optionally substituted alkyl, cycloalkyl groups or $R_3$ and $R_4$ together with the carbon atom to which they are attached form a cycloalkyl, or heterocyclyl ring.

5. The compound as claimed in claim 1, wherein $R_5$ is selected from the group consisting of $-OR_6$, $-NR_7COR_6$ and $-NR_7SO_2R_6$, wherein $R_6$ and $R_7$ are as defined earlier.

6. The compound as claimed in claim 1, wherein $R_8$ is selected from the group consisting of hydrogen, hydroxy, cyano, halo, haloalkyl, $(C_1-C_{10})$alkyl, $(C_2-C_{10})$alkenyl, $(C_2-C_{10})$alkynyl, $(C_3-C_8)$cycloalkyl, aryl, heterocyclyl, heteroaryl aralkyl, heterocyclylalkyl, $-COR_9$, $-COOR_9$, $-OR_9$, $-S(O)_mR_9$, $-NR_9R_{10}$, $-CONR_9R_{10}$, $-N(R_9)COR_{10}$, $-N(R_9)COOR_{10}$, $-OCH_2COR_9$, $-N(R_9)CH_2COR_{10}$, $-N(R_9)CONR_9R_{10}$, $-SO_2NR_9R_{10}$, $-N(R_9)SO_2R_{10}$ derivatives wherein each of $R_9$ and $R_{10}$ at each occurrence independently represents hydrogen, hydroxy, alkoxy, haloalkyl, optionally substituted $(C_1-C_{10})$alkyl, $(C_2-C_{10})$alkenyl, $(C_2-C_{10})$alkynyl, $(C_3-C_8)$cycloalkyl, $(C_5-C_8)$cycloalkenyl, optionally substituted amino, aryl, heteroaryl, heterocyclyl, aralkyl, heterocyclylalkyl groups, or wherever feasible or $R_9$ and $R_{10}$ together with the atom to which they are attached may form a 5-8 membered cyclic ring containing 0-2 additional heteroatoms selected from $-O-$, $-NR_7-$ and $S(O)_m$, wherein $R_7$ and m are as defined earlier.

7. The compound as claimed in claim 1, wherein the substitution on $R_1$ or $R_8$ is independently selected from hydrogen, hydroxy, cyano, halo, nitro, oxo, imino, haloalkyl, $(C_1-C_{10})$alkyl, $(C_2-C_{10})$alkenyl, $(C_2-C_{10})$alkynyl, $(C_3-C_8)$cycloalkyl, aryl, heterocyclyl, heteroaryl, aralkyl, heterocyclylalkyl, $-COR_9$, $-C(O)COR_9$, $-COOR_9$, —OR$_9$, —S(O)$_m$R$_9$, —NR$_9$R$_{10}$, —CONR$_9$R$_{10}$, —N(R$_9$)COR$_{10}$, —N(R$_9$)COOR$_{10}$, —NR$_9$NR$_{10}$COR$_9$, —OCH$_2$COR$_9$, —N(R$_9$)CH$_2$COR$_{10}$, —N(R$_9$)CONR$_9$R$_{10}$, —P(O)(OR$_{10}$)$_2$, —SO$_2$NR$_9$R$_{10}$, —N(R$_9$)SO$_2$R$_{10}$ derivatives, wherein R$_9$ & R$_{10}$ are as defined earlier.
8. A compound as claimed in claim 1 selected from the group comprising of:
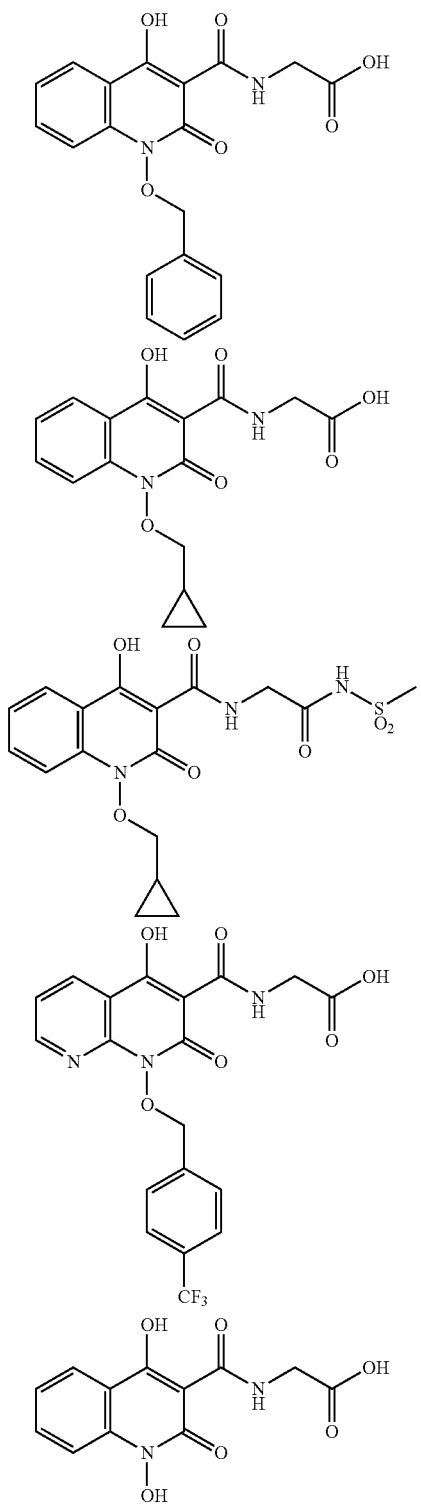
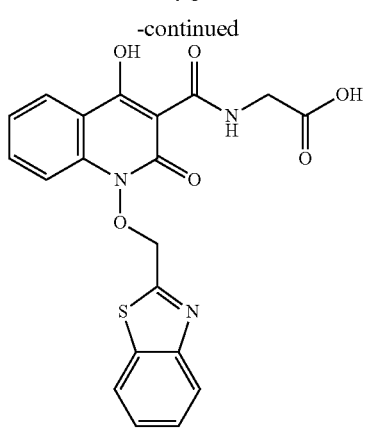
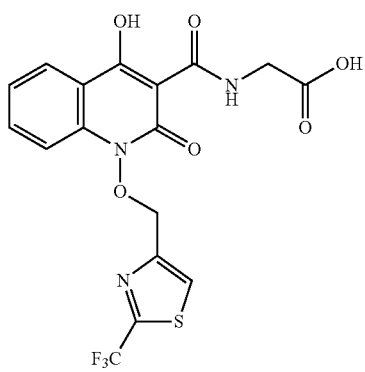
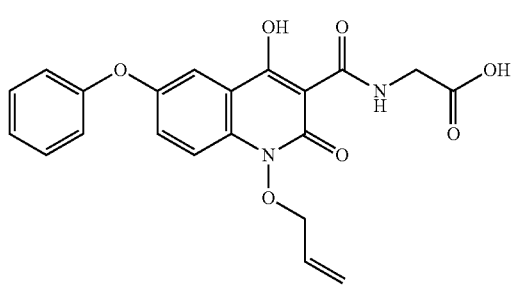
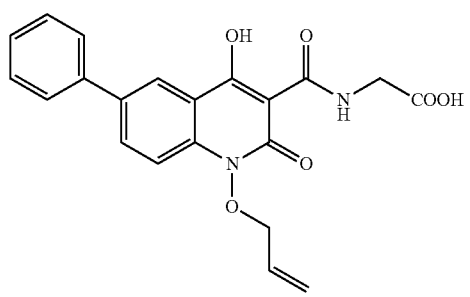
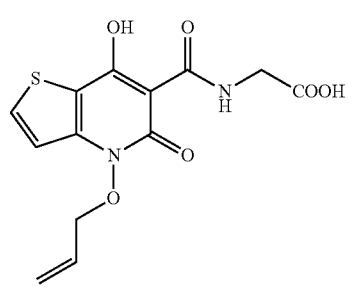

77 -continued | 78 -continued

79
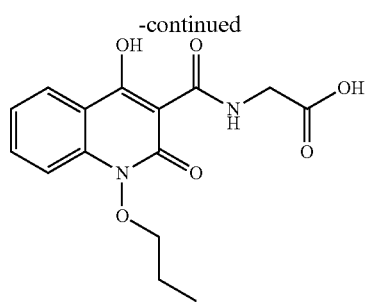
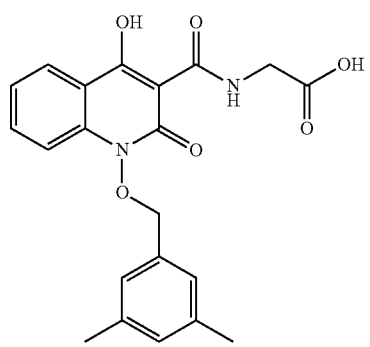
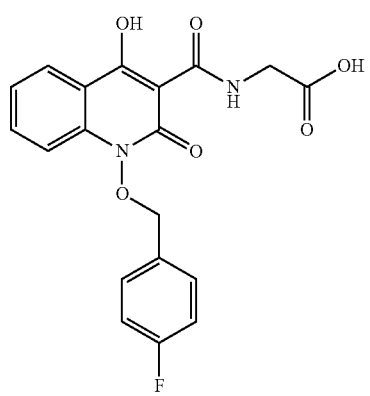
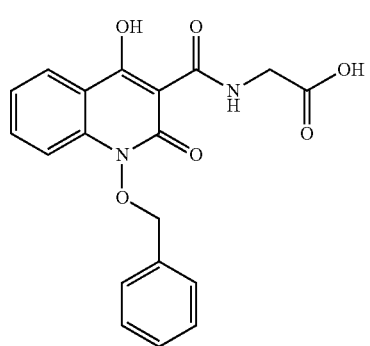
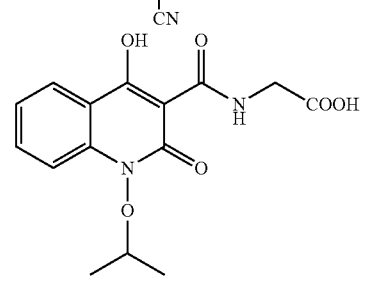
80
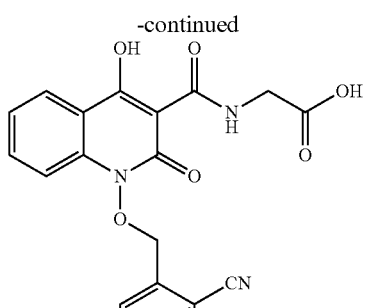
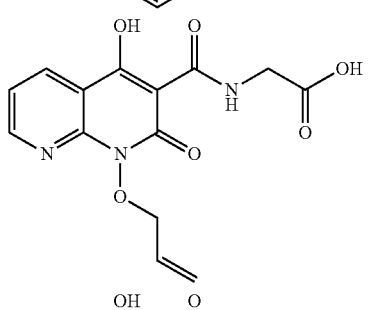
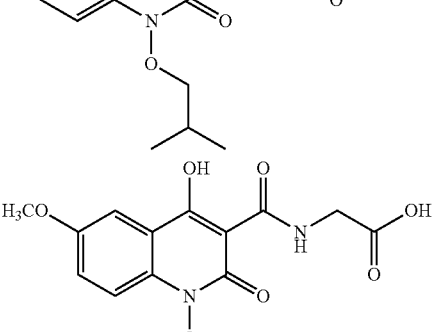
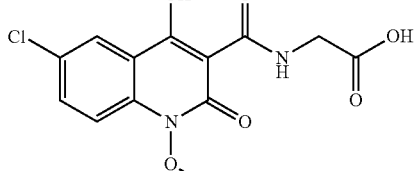
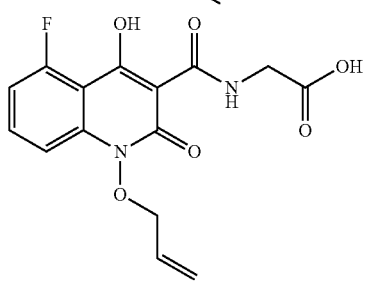

81
-continued
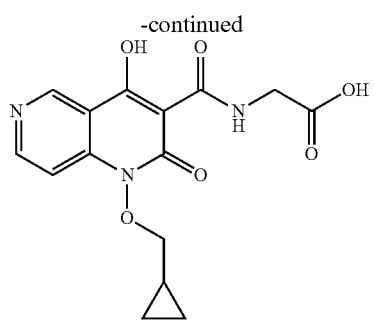
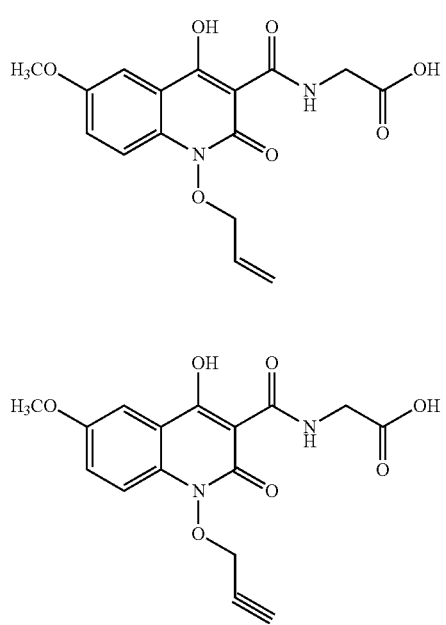
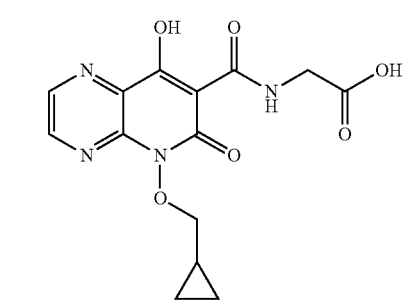
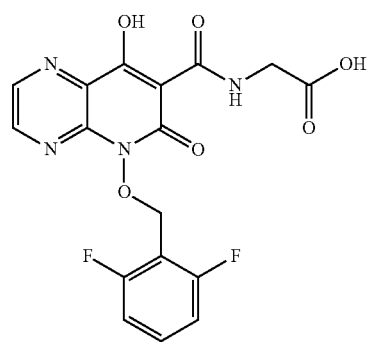
82
-continued
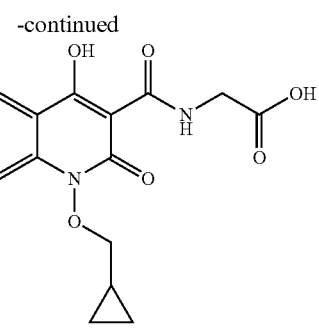
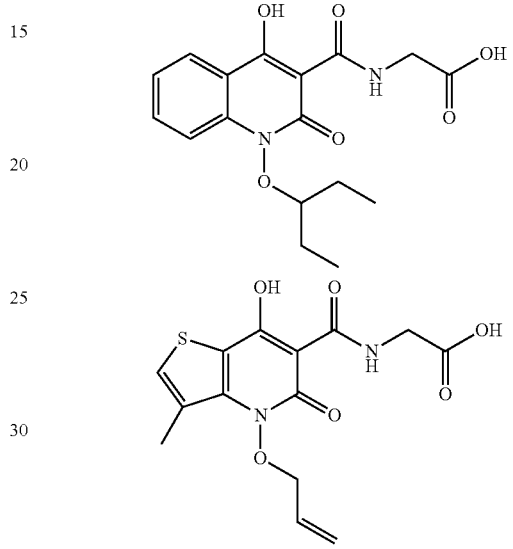
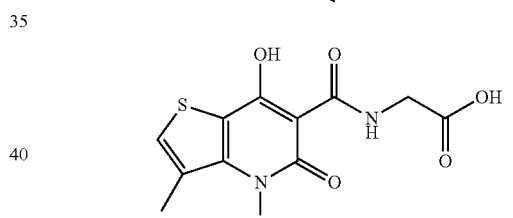
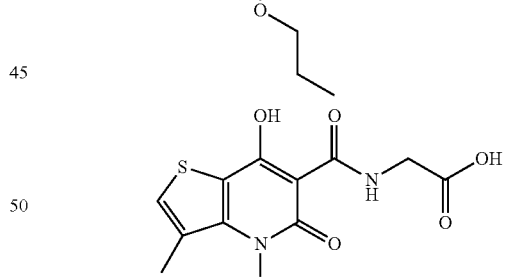
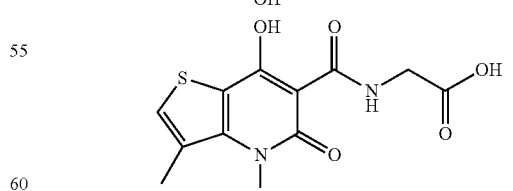
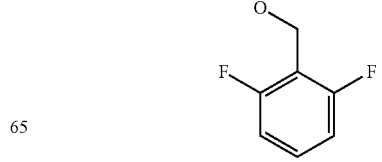

83
-continued
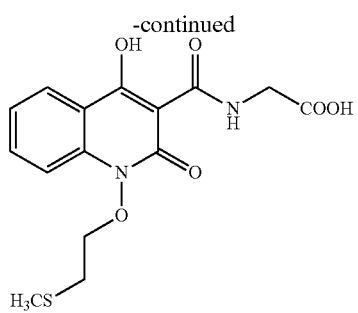
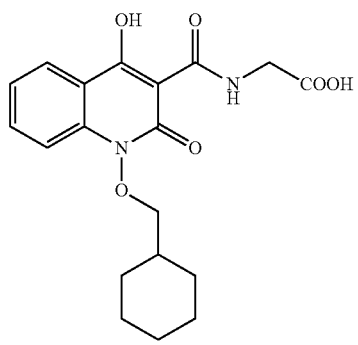
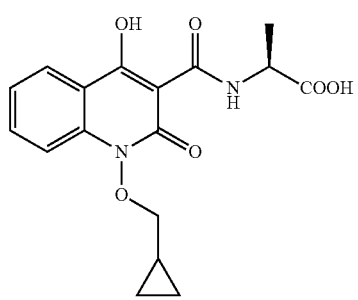
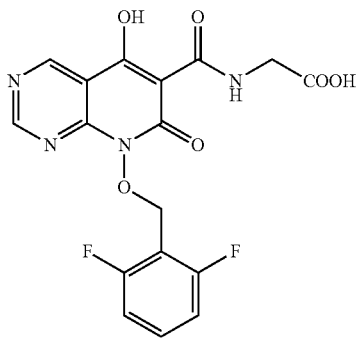
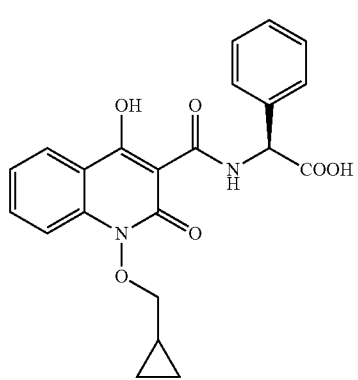
84
-continued
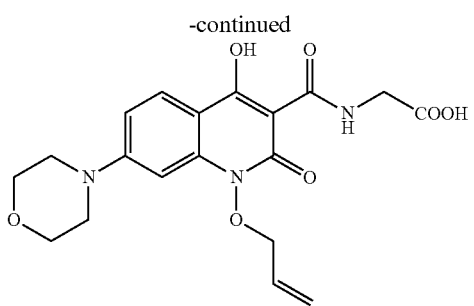
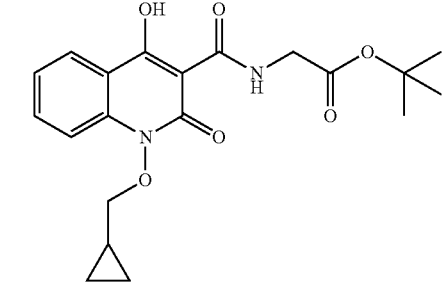
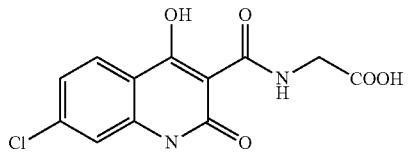
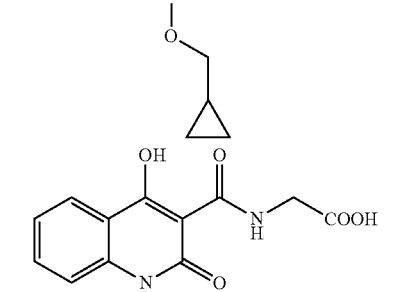
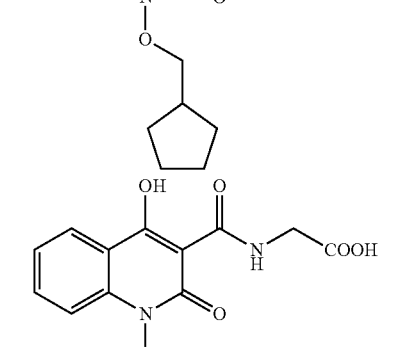
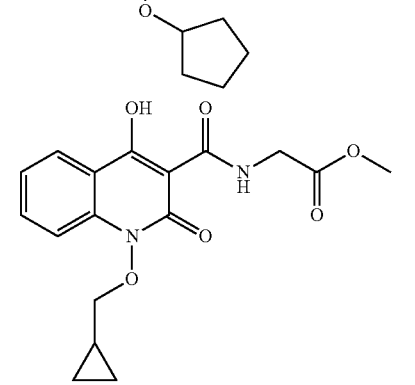

85
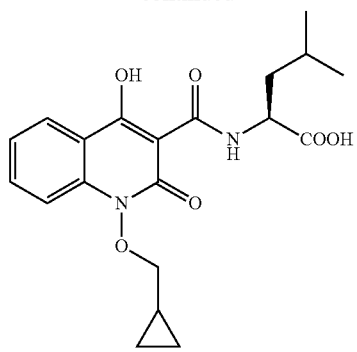
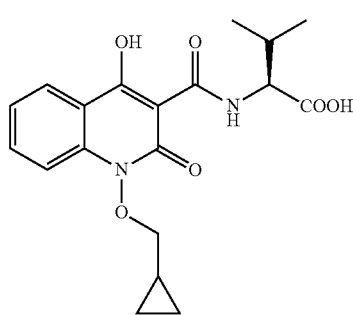
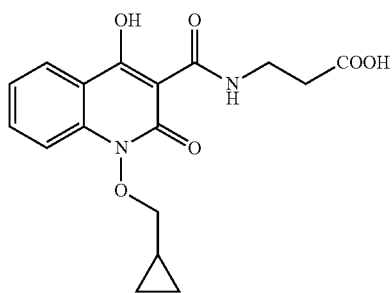
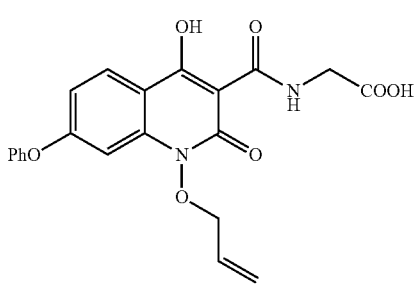
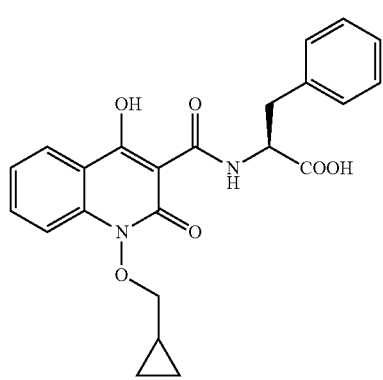
86
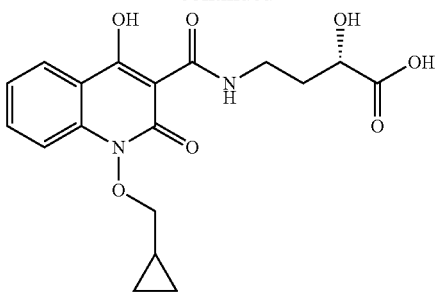
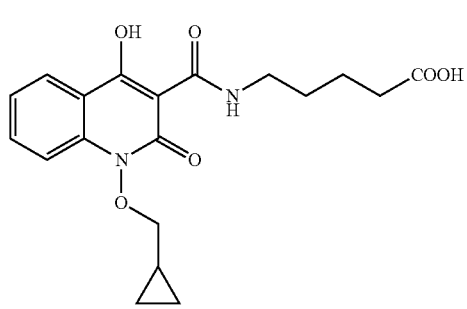
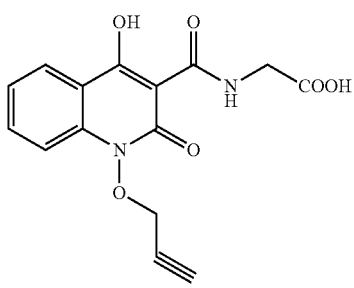
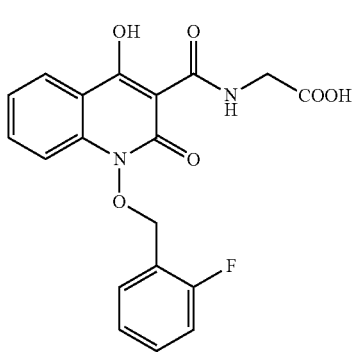
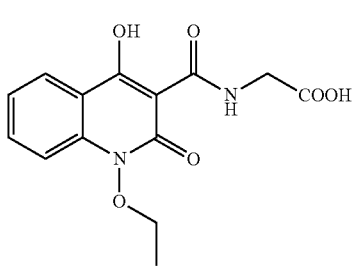

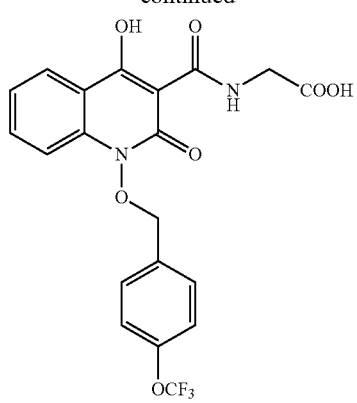
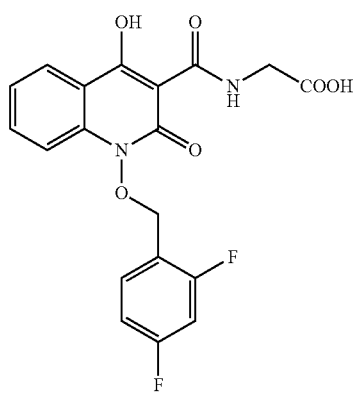
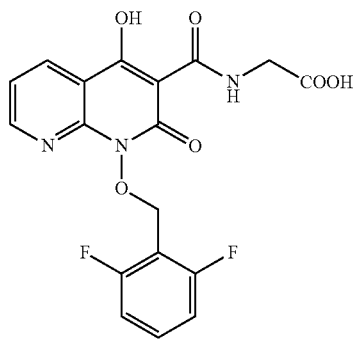
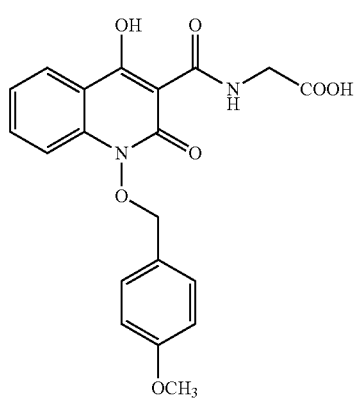
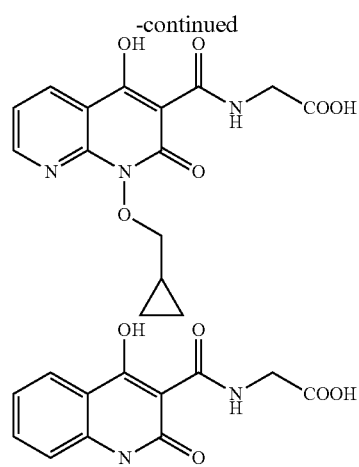
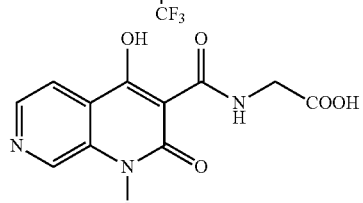
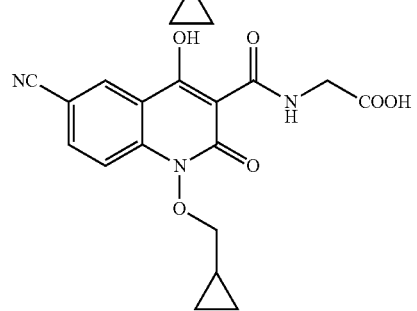
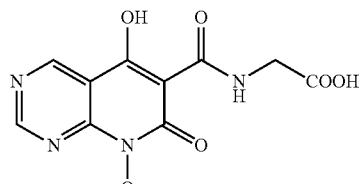
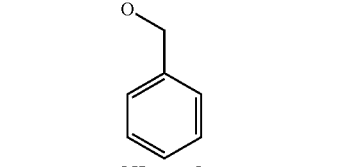
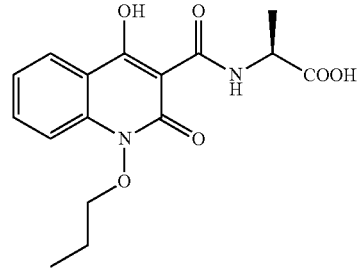

-continued
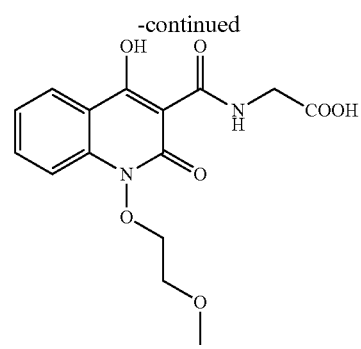
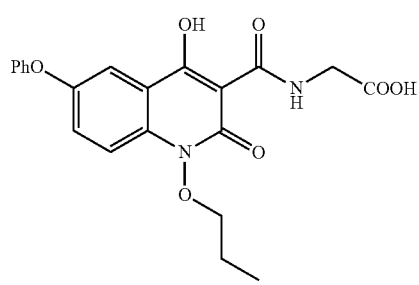
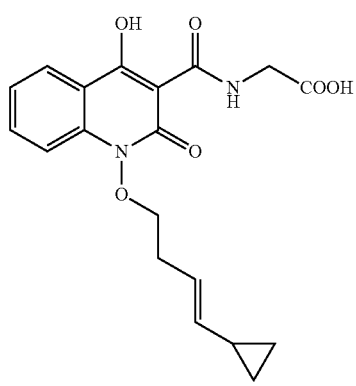
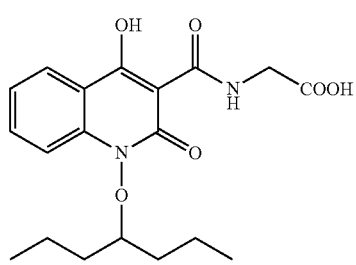
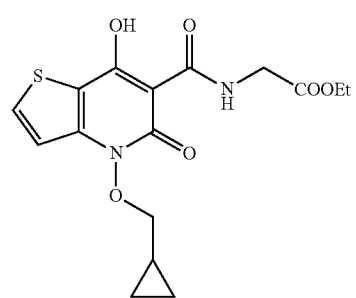
-continued
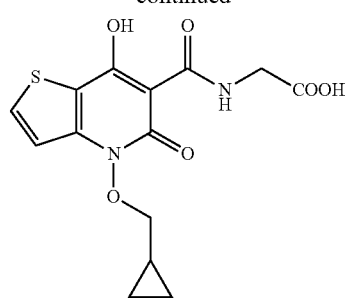
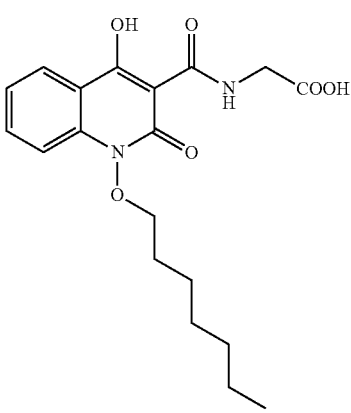
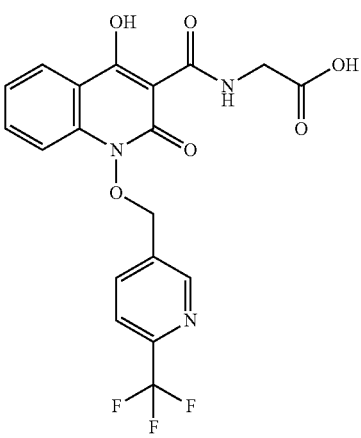
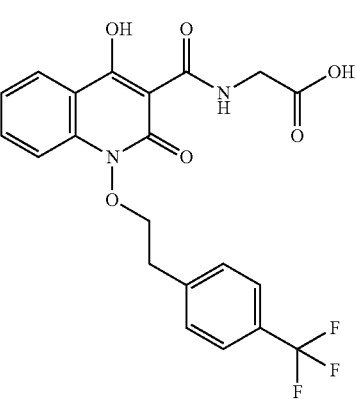

91
-continued
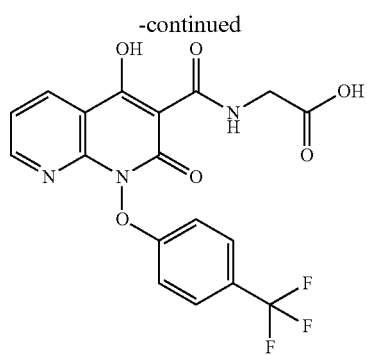
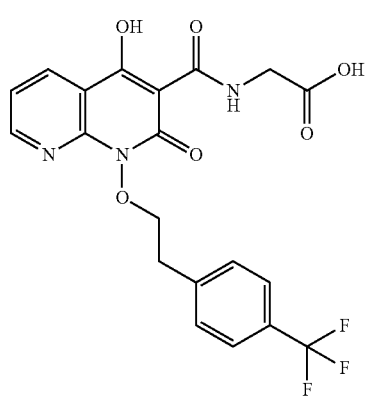
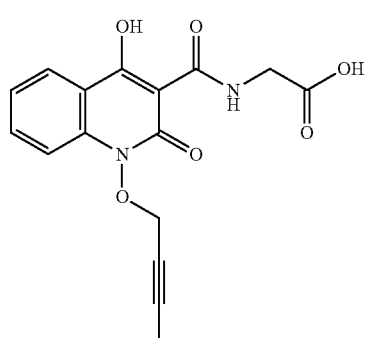
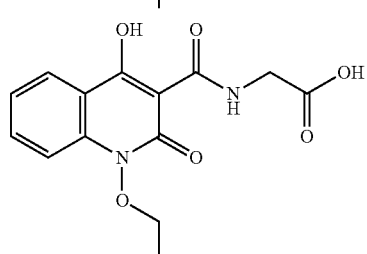
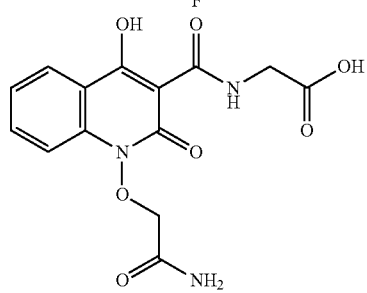
92
-continued
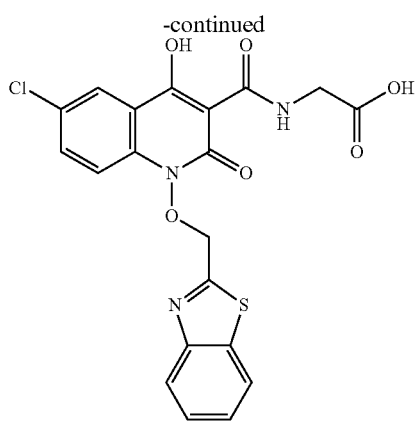
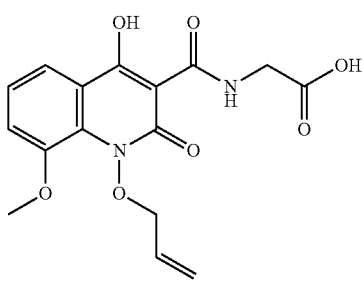
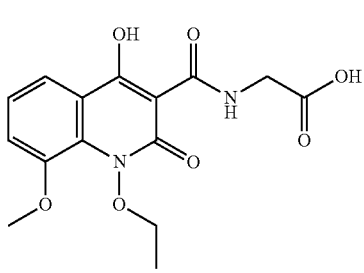
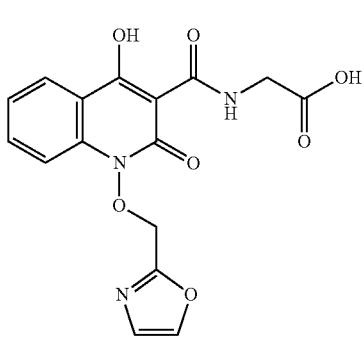
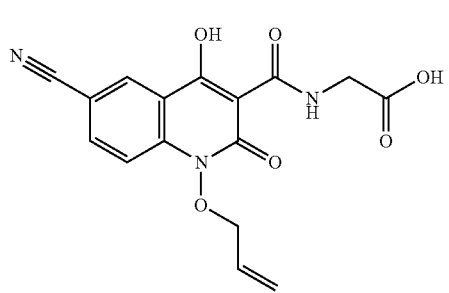

93
-continued
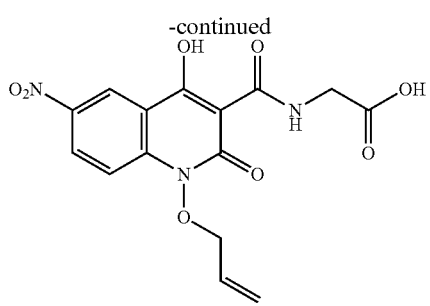
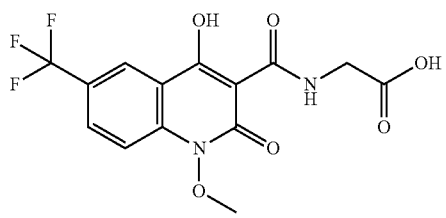
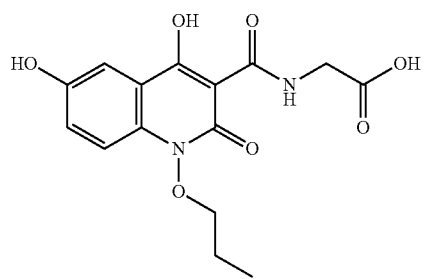
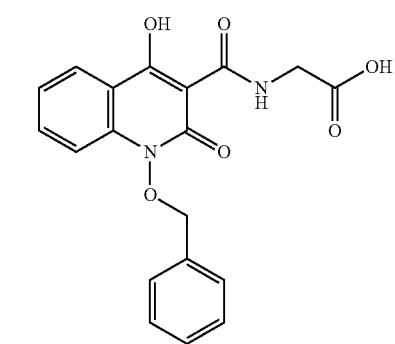
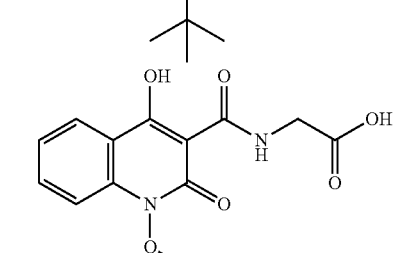
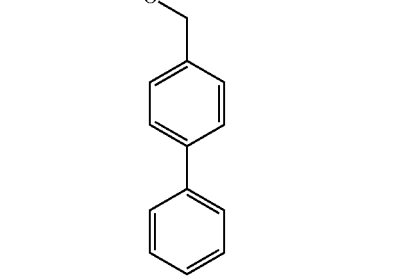
94
-continued
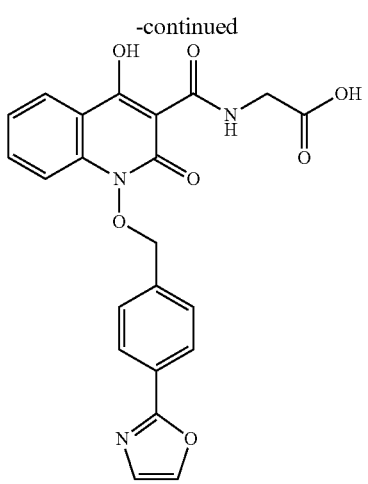
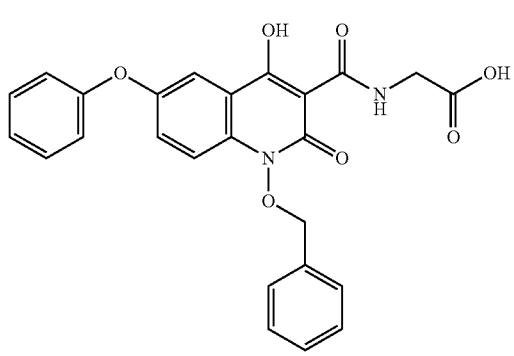
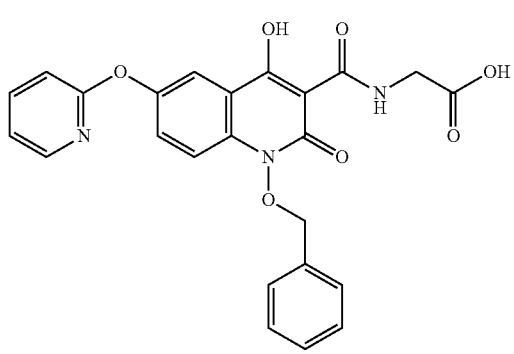
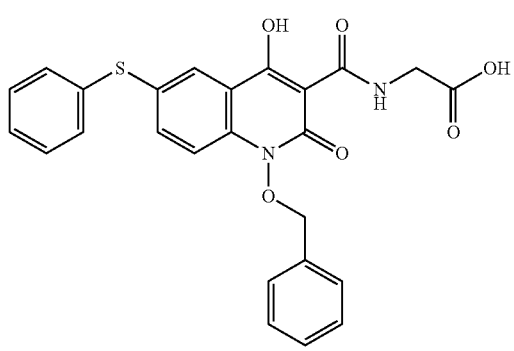

95
-continued
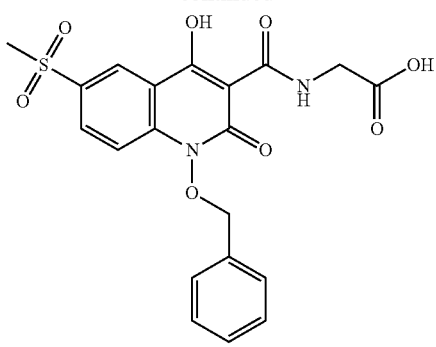
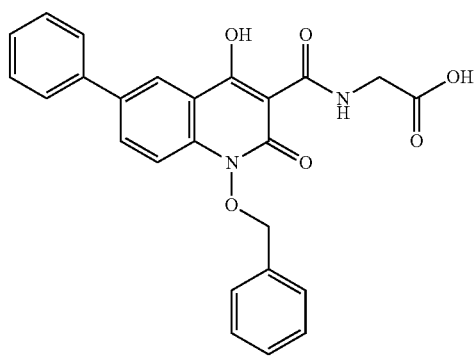
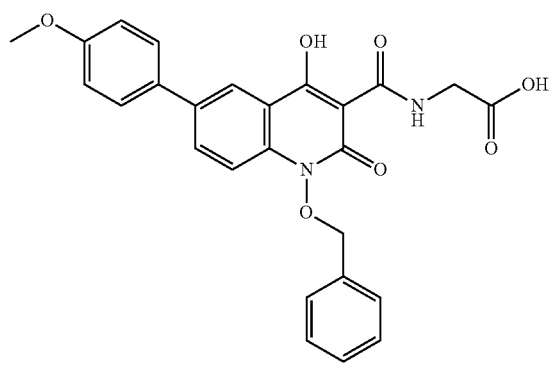
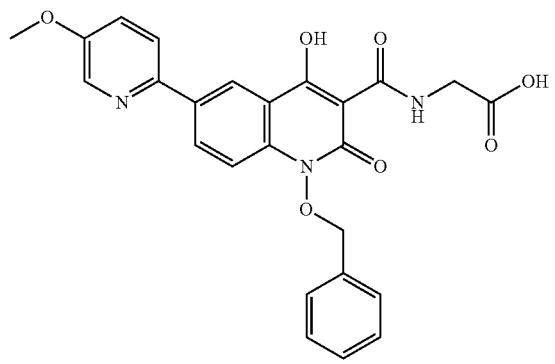
96
-continued
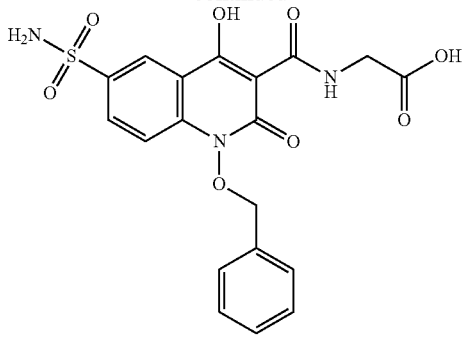
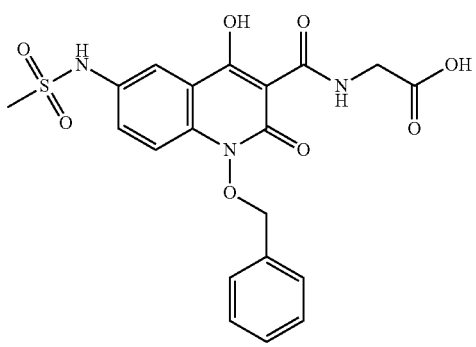
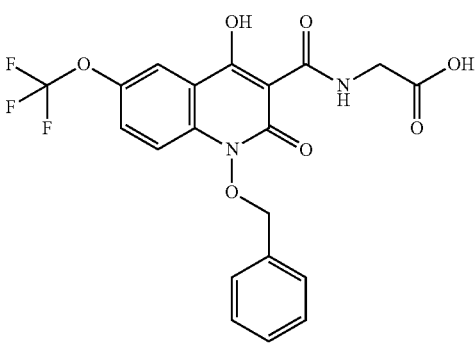
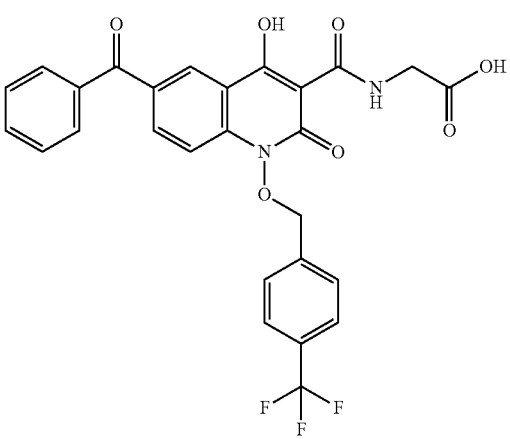

97
-continued
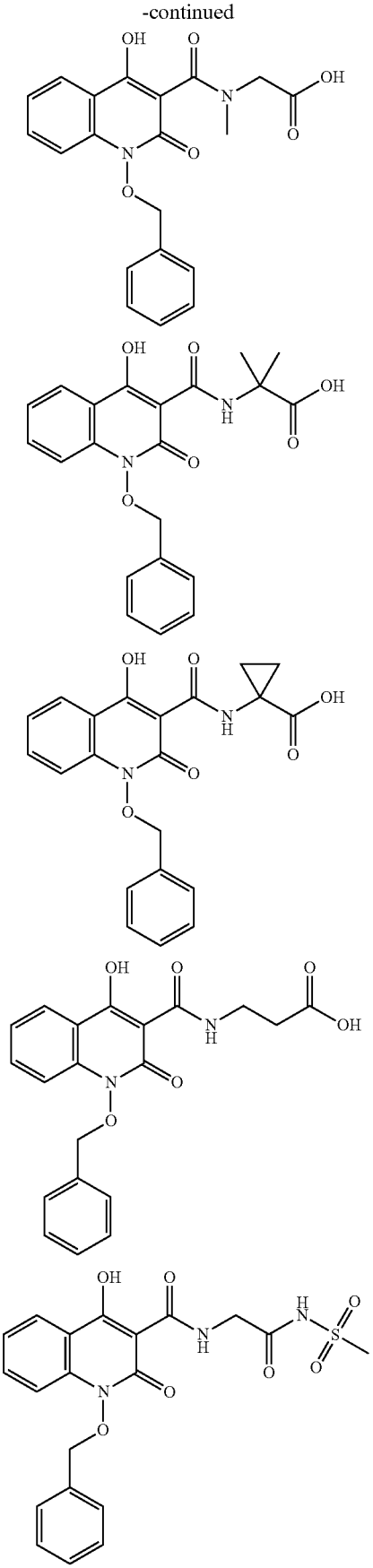
98
-continued
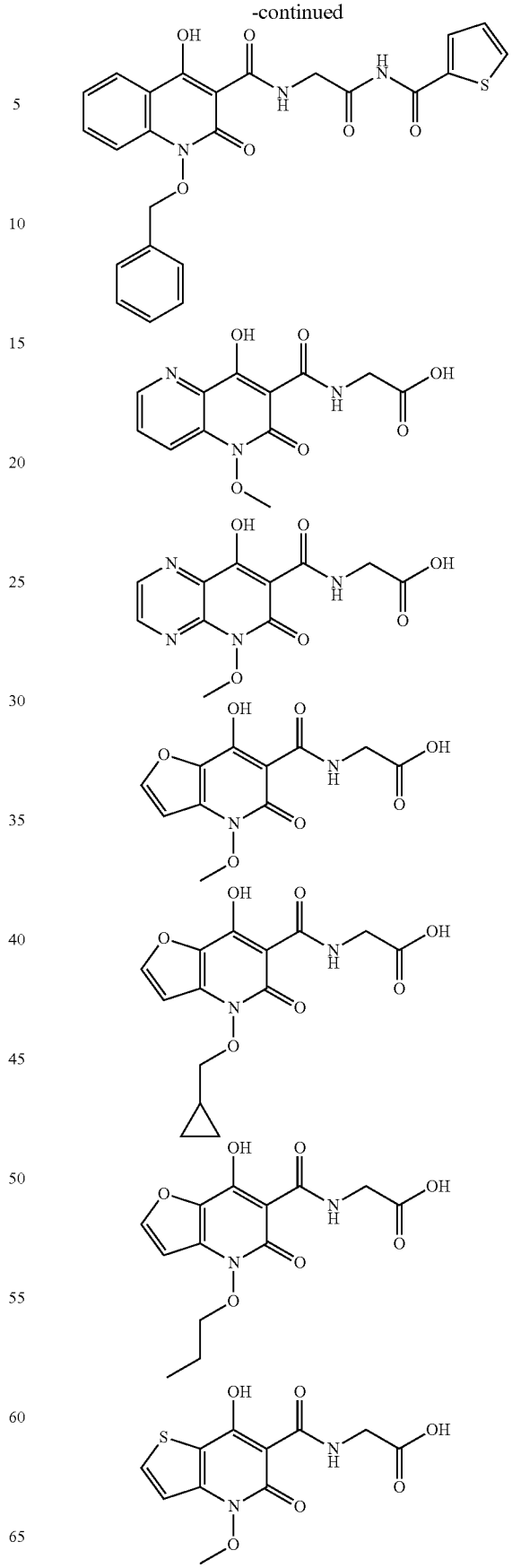

99
-continued
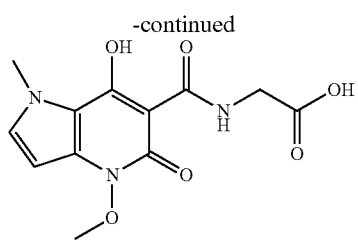
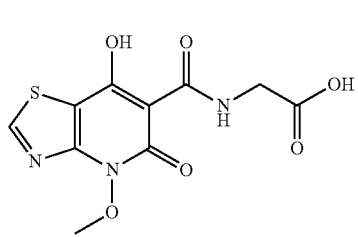
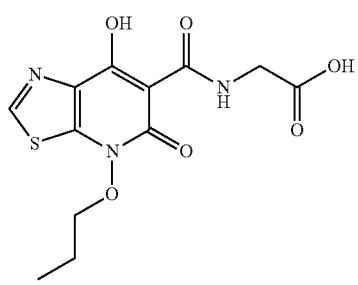
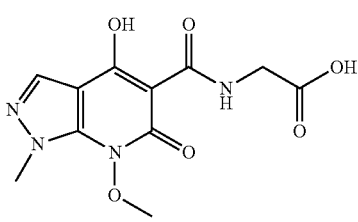
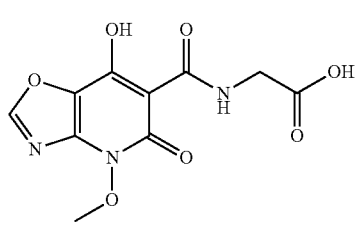
100
-continued
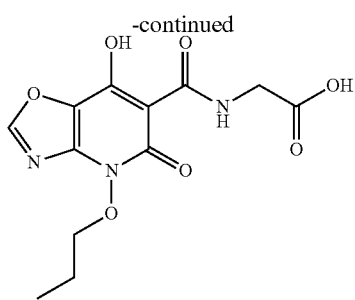
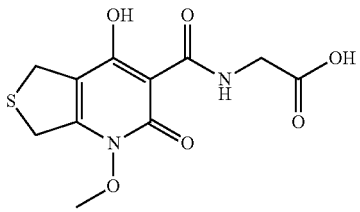
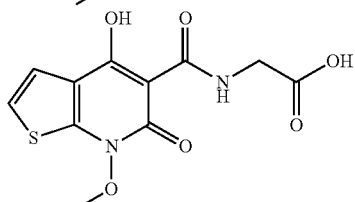
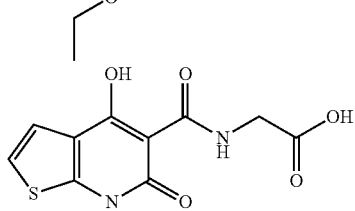
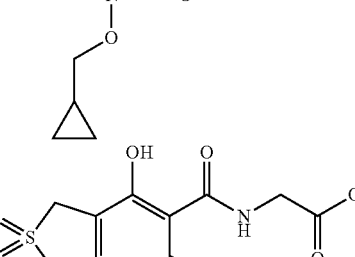
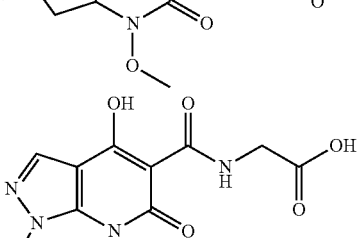
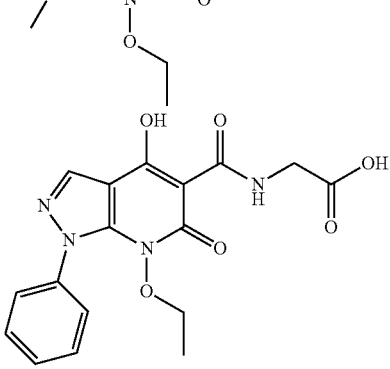

101

-continued

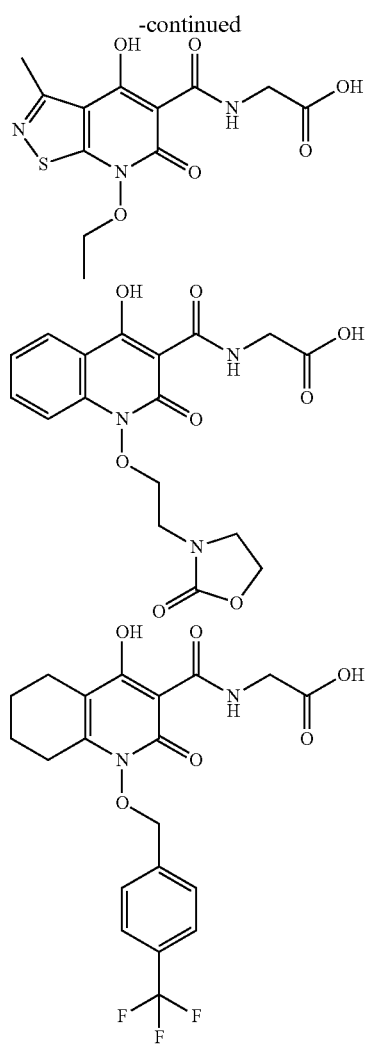

102

-continued

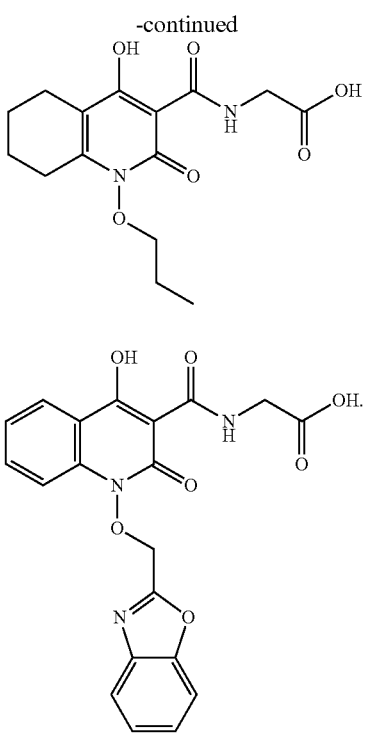

9. A pharmaceutical composition comprising a therapeutically effective amount of a compound of formula (I) as claimed in claim 1 and optionally one or more pharmaceutically acceptable carriers, diluents or excipients.

10. A method for the treatment of anemia in a patient which comprises administering to a patient in need thereof an effective amount a compound of formula (I) as claimed in claim 1 or its suitable pharmaceutical composition.

* * * * *